US005627270A

United States Patent [19]

Kahne et al.

[11] Patent Number: 5,627,270
[45] Date of Patent: May 6, 1997

[54] GLYCOSYLATED STEROID DERIVATIVES FOR TRANSPORT ACROSS BIOLOGICAL MEMBRANES AND PROCESS FOR MAKING AND USING SAME

[75] Inventors: Daniel E. Kahne; Suzanne W. Kahne, both of Princeton; Michael J. Sofia, Laurenceville; Nicole T. Hatzenbuhler, Kendall Park, all of N.J.

[73] Assignees: Trustees of Princeton University, Princeton; Transcell Technologies, Inc., Monmouth Junction, both of N.J.

[21] Appl. No.: 264,488

[22] Filed: Jun. 23, 1994

Related U.S. Application Data

[63] Continuation-in-part of Ser. No. 230,685, Apr. 20, 1994, which is a continuation-in-part of Ser. No. 989,667, Dec. 14, 1992, which is a continuation-in-part of Ser. No. 806,985, Dec. 13, 1991, Pat. No. 5,338,837.

[51] Int. Cl.$^6$ .......................... C07J 17/00; C07H 21/02; C07H 21/04
[52] U.S. Cl. .......................... 536/5; 536/23.1; 536/24.1; 536/24.3; 514/26; 514/44
[58] Field of Search .......................... 536/5, 23.1, 24.1, 536/24.3; 514/26, 44

*Primary Examiner*—John Kight
*Assistant Examiner*—Howard C. Lee
*Attorney, Agent, or Firm*—Lowe, Price, LeBlanc & Becker

[57] ABSTRACT

Novel glycosylated steroid derivatives for facilitating the transport of compounds across biological membranes, either in admixture or as conjugates, are disclosed. A novel process for efficient synthesis of these glycosylated steroid derivatives, using activated glycosyl sulfoxide intermediates is provided. Methods for the permeabilization of membranes and the enhancement of the activity of predetermined compounds are also provided.

7 Claims, 22 Drawing Sheets

Synthesis of an Endorphin Mimic

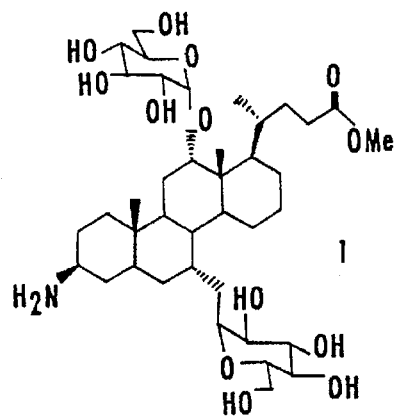
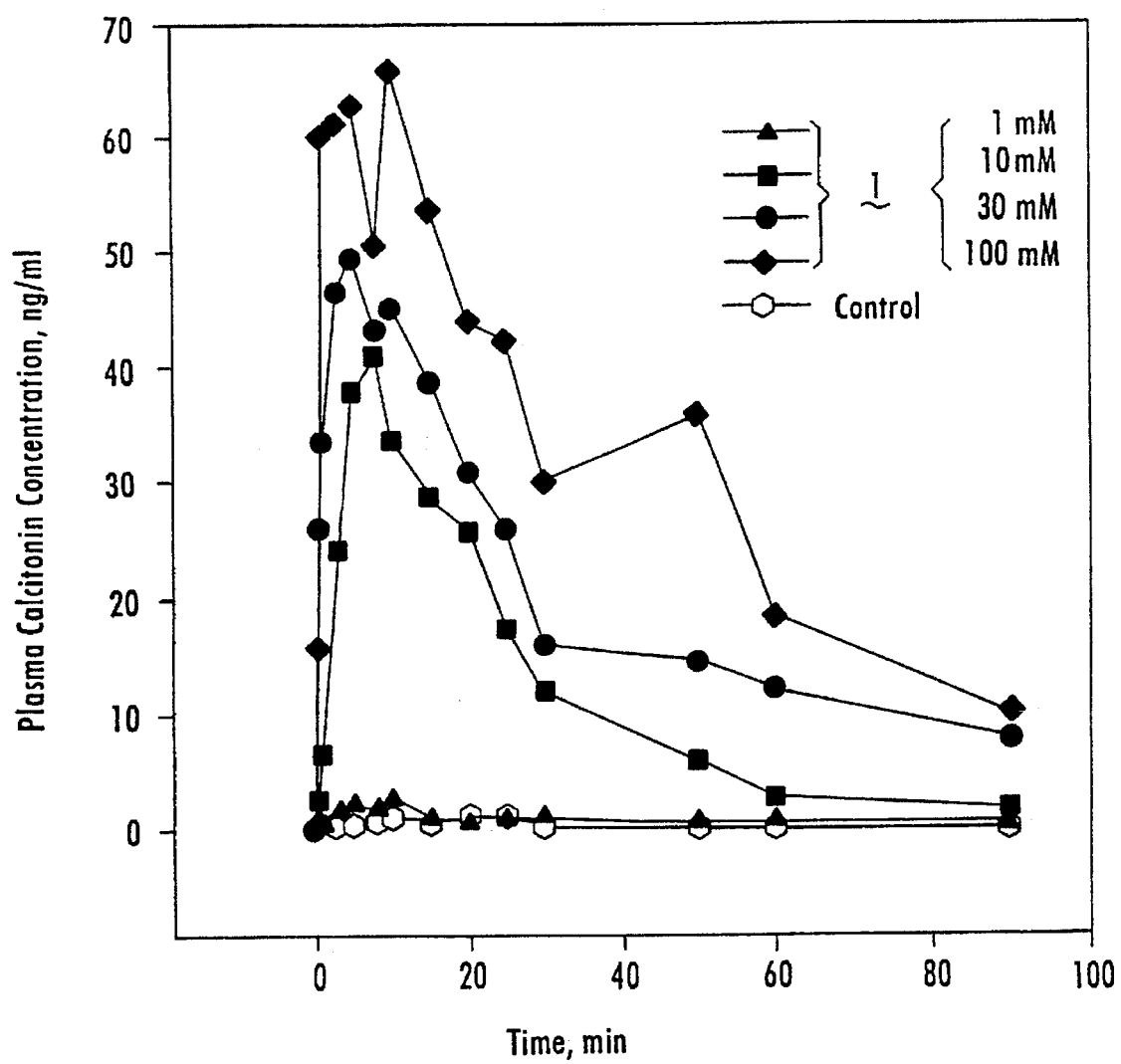
Fig. 19

ILEAL DELIVERY OF GENTAMICIN IN RATS

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: modified_base
        ( B ) LOCATION: 1
        ( D ) OTHER INFORMATION: /note= "5' position may be modified
            with: $H_2N(CH_2)_6OP(O)_2-$, which may be further
            modified at the amino group with cholic acid,
            7,12- bisglycosylcholic acid (BGCA), or 3-beta-amino-
            BGCA"

( x i ) SEQUENCE DESCRIPTION: SEQ ID NO:1:

ACACCCAATT CTGAAAATGG                                          2 0

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: unknown ( i i ) MOLECULE TYPE: DNA (genomic)

-continued

```
(ix) FEATURE:
    (A) NAME/KEY: modified_base
    (B) LOCATION: 1
    (D) OTHER INFORMATION: /note= "5' position may be modified
        with: H2N(CH2)6OP(O)2—, which may be further
        modified at the amino group with cholic acid,
        7,12- bisglycosylcholic acid (BGCA), or 3-beta-amino-
        BGCA"

(xi) SEQUENCE DESCRIPTION: SEQ ID NO:2:

AAGTCCCTGT TCGGGCGCCA                                          20
```

GLYCOSYLATED STEROID DERIVATIVES FOR TRANSPORT ACROSS BIOLOGICAL MEMBRANES AND PROCESS FOR MAKING AND USING SAME

This invention was made with Government support under ONR Grant No. N0014-91-J-1230. The Government has certain rights in this invention.

This application is a continuation-in-part (CIP) of co-pending application Ser. No. 08/230,685, filed Apr. 20, 1994, which is a CIP of co-pending Ser. No. 07/989,667, filed Dec. 14, 1992, which in turn is a CIP of Ser. No. 07/806,985, filed Dec. 13, 1991, now U.S. Pat. no. 5,338,837, the complete disclosures of which are incorporated by reference herein.

BACKGROUND OF THE INVENTION

The invention is generally directed to novel glycosylated steroid derivatives. These derivatives have a variety of uses, including but not limited to the general permeabilization of membranes, such as biological membranes (e.g., cellular, mucosal, gastrointestinal, blood-brain barrier, and the like). In particular, the present derivatives are useful in facilitating the transport of molecules across biological membranes. The facilitation is achieved by combining the present derivatives with the molecules of interest, either as a conjugate comprising the present derivative covalently linked directly or indirectly with the molecule of interest or as an admixture comprising the two main components. In this manner, the molecule of interest, especially those of a therapeutic significance (more, below) can better exhibit its activity, whether of a biological, physical or chemical nature. The invention is further directed to novel methods for the efficient synthesis of these derivatives, including their combinations with representative molecules of interest.

To elicit the desired biological response, a molecule of therapeutic significance, i.e., those having a diagnostic, prophylactic or therapeutic use (and termed herein "therapeutically-significant-molecule" or "therapeutically-significant-compound"), must be made available in an effective-concentration at its site of action. Many factors determine the concentration of a therapeutically-significant-compound, which ultimately reaches the site of action, including the amount administered, and the extent and rate of the compound's absorption, distribution, biotransformation, and excretion. (Goodman and Gilman, *The Pharmacological Basis of Therapeutics*, 6th Edition, MacMillan Publishing Co., Inc., New York, 1980, pp. 1–39.) The foregoing factors may, in turn, be influenced by the chosen route of administration of the therapeutically-significant-compound.

The most common routes of administration of therapeutically-significant-compounds are parenteral (e.g., intravenous, subcutaneous, and intramuscular) and enteral (oral ingestion), although methods to administer therapeutically-significant-compounds across the skin (e.g., transdermal) or mucosa (e.g., oral, nasal, rectal, vaginal, and the like) also are known. Parenteral methods are considered to be extremely effective, in general, allowing for rapid increases in blood levels of a wide range of therapeutically-significant-compounds. Parenteral methods are advantageous in that they circumvent first-passage hepatic metabolism. However, parenteral administration of a therapeutically-significant-compound can cause pain, irritation, possible tissue damage over the long term, and carries a potential risk of infection. In addition, parenteral methods frequently are inconvenient, particularly those that are restricted to trained medical personnel (e.g., intravenous methods).

Enteral methods are more convenient than parenteral methods, and generally are more economical and acceptable to the recipients. However, orally administered, therapeutically-significant-compounds may be inefficiently absorbed (for example, they may decompose within the gastrointestinal tract or may simply pass through without absorption). Moreover, the time from ingestion to absorption may prohibit effective use in emergency situations. As stated above, certain therapeutically-significant-compounds cannot be orally administered as they are destroyed, prior to reaching their site of action, by the digestive enzymes, acid, and surface-active lipids in the gut. Other therapeutically-significant-compounds are subject to extensive, first-passage hepatic metabolism, rendering them ineffective following oral administration.

Non-parenteral methods which circumvent problems associated with instability of drug preparations in the gut and first-passage hepatic metabolism long have been sought. Administration via transdermal, oral mucosal, rectal, and nasal routes are among the alternatives which have been explored. Such alternatives further include administering the therapeutically-significant-compound orally, but encapsulated in a protective delivery system designed to extrude the contents at a predetermined point in the lower gastrointestinal tract. However, the efficacy of these alternative drug delivery methods often is limited by poor absorption of the therapeutically-significant-compounds at the site of delivery or application.

Effective strategies to enhance absorption of therapeutically-significant-molecules across membranes, such as mucosal membranes, cellular membranes, nuclear membranes, and the like, could enhance the efficacy of many known drug preparations that are poorly absorbed regardless of the method of administration. Such strategies to enhance trans-membrane absorption or penetration could be particularly useful for therapeutically-significant-compounds that are administered across the skin and mucosal tissues, including mucosal tissues of the gastrointestinal, genitourinary, and respiratory tracts.

The basic structural unit of biological membranes is a phospholipid bilayer, in which are embedded proteins of various size and composition. The surfaces of the phospholipid bilayer, which project into the aqueous cellular environment, are formed by the hydrophilic heads of the phospholipids; the interior of the bilayer is comprised of the fatty acyl hydrophobic tails. The membrane proteins may be involved in transport processes and also may serve as receptors in cellular regulatory mechanisms or signal transduction.

Natural mechanisms for traversal of biological membranes include passive diffusion, facilitated diffusion, active transport, receptor-mediated endocytosis and pinocytosis. Passive diffusion works best for small molecules that are lipid-soluble. However, biological membranes are essentially impermeable to most water-soluble molecules, such as nucleosides, amino acids, proteins, and other hydrophilic, therapeutically-significant-molecules. Such molecules enter cells via some type of carrier-mediated transport system in which specific entities facilitate traversal of the membrane. Natural carriers for facilitating traversal of the membrane are of limited utility, however, as such carriers will accept substrates of only a predetermined molecular configuration. Many therapeutically-significant-compounds are not efficiently absorbed because they are neither lipophilic enough to diffuse passively across cell membranes nor possess the structural features recognized by the natural transport systems.

Strategies to enhance the uptake of therapeutically-significant-molecules across biological membranes have been investigated previously and fall into two broad categories. The first category includes all strategies in which the structure of the therapeutically-significant-compound is changed, either by making the compound itself more lipophilic or by conjugating the compound to other entities known to interact with phospholipid membranes. The common goal has been to increase passive diffusion across the membrane by lowering the energy barrier to diffusion and/or by increasing the local concentration of the compound at the membrane surface.

As mentioned above, the first category includes the strategy of taking advantage of the cellular transport mechanism (either active or facilitated transport or receptor-mediated endocytosis) by conjugating the therapeutically-significant-compound to entities known to interact with the cellular transport machinery. Among the reported techniques to conjugate molecules of therapeutic significance to other entities is the work of Letsinger and others on oligonucleotidecholesterol conjugates. (See, Letsinger R. L. et al. "Cholesteryl-conjugated oligonucleotides: Synthesis, properties, and activity as inhibitors of replication of human immunodeficiency virus in cell culture." *Proc. Natl. Acad. Sci. USA* (September 1989) 86:6553–6556; Stein C. A. et al. "Mode of Action of 5'-Linked Cholesteryl Phosphorothioate Oligodeoxynucleotides in Inhibiting Syncytia Formation and Infection by HIV-1 and HIV-2 in Vitro." *Biochemistry* (1991) 30:2439–2444.)

Targeting molecules to the brain requires traversal of the blood-brain barrier, a capillary including system with unique morphological characteristics, which acts as a system-wide cellular membrane separating the brain interstitial space from the blood. Like other biological membranes, the blood-brain barrier is relatively impermeable to many hydrophilic, therapeutically-significant-compounds. The strategies which have been developed for targeting compounds to the brain include direct delivery by invasive procedures, intra-arterial infusion of hypertonic substances, and conversion of hydrophilic compounds to lipid-soluble entities.

U.S. Pat. No. 4,902,505 describes a recent attempt to facilitate transport by coupling a hydrophilic peptide of interest to a peptide carrier which itself is capable of traversing the barrier via receptor-mediated transcytosis.

The second broad category to enhance uptake includes those strategies in which the therapeutically-significant-compound is administered to specific body surfaces as an admixture with other molecules that are known to permeabilize membranes. For example, several investigators have attempted to mix insulin with adjuvants, such as bile salts, which might enhance nasal insulin absorption. (See, Hirai et al. *Int. J. Pharmaceutics* (1981) 9:165–184; Hirai et al. *Diabetes* (1978) 27:296–199; British Patent No. 1,527,506; U.S. Pat. No. 4,153,689; and Pontiroli et al. *Br. Med. J.* (1982) 284:303–386.) EP 0 444 778 describes the use of alkyl saccharides to enhance the penetration of topically applied drugs across mucus-covered epithelial tissues, in general, and the corneal epithelium, in particular. U.S. Pat. No. 4,865,848 to Cheng et al., issued Sep. 12, 1989, discloses the use of sucrose esters, particularly sucrose monolaurate, for enhancing the transdermal flux of transdermally-delivered drugs. U.S. Pat. No. 4,746,508 to Carey et al., issued May 24, 1988, reports the use of fusidic acid and cephalosporin derivatives to increase the permeability of human and animal body surfaces to drugs.

The glycosylated steroid derivatives of the present invention may be used effectively in a strategy for enhancing the uptake of a second compound through a particular membrane, including the two broad categories discussed above. Indeed, it has been discovered that the instant derivatives can interact with a wide variety of membranes, including biological phospholipid membranes, thereby possessing the potential to enhance the penetration of therapeutically-significant-compounds through such membranes.

Like some of the previously used adjuvants and "enhancers" (e.g., cholic acid and fusidic acid derivatives), the novel derivatives of the present invention are amphiphilic in a facial sense; that is, one side or face of the molecule is hydrophobic while the opposite side or face is hydrophilic. However, the novel derivatives of the present invention have structural features which differ significantly from those of the previously known "enhancers". That is, the instant derivatives are glycosylated on the hydrophilic face of the molecule in a manner that is not shared by any previously known, facially-amphiphilic steroid.

The present inventors have discovered that glycosylation on the hydrophilic surfaces significantly changes both the solubility properties of the steroids and the manner in which they associate. Many of the instant glycosylated steroids have been shown by the inventors to be more effective than the parent, nonglycosylated steroids in permeabilizing both artificial and biological membranes. The novel, glycosylated steroid derivatives of the present invention, therefore, have been found to increase the delivery of therapeutically-significant-compounds across a variety of membranes. The enhanced transport is facilitated by combining the instant derivatives with the therapeutically-significant-compounds, either as admixtures or as conjugates therewith.

Prior to the present invention, no method existed for efficiently synthesizing all of the glycosylated steroid derivatives of the present invention. Many glycosylation reactions using thioglycosides have been reported. (See, Ferrier R. J. et al. "A Potentially Versatile Synthesis of Glycosides." *Carbohydrate Research* (1973) 27:55–61; Garegg P. J. et al. "A reinvestigation of glycosidation reactions using 1-thioglycosides as glycosyl donors and thiophilic cations as promoters," *Carbohydrate Research* (1983) 116:162–5; Nicolaou K. C. et al. "A Mild and General Method for the Synthesis of O-Glycosides," *J. Am. Chem. Soc.* (1983) 105:2430–2434; Lonn H. "Synthesis of a tri- and a hepta-saccharide which contain α-L-fucopyranosyl groups and are part of the complex type of carbohydrate moiety of glycoproteins," Research (1985) 139:105–113; Andersson F. et al. "Synthesis of 1,2-cis-linked glycosides using dimethyl(methylthio) sulfonium triflate as promoter and thioglycosides as glycosyl donors," *Tetrahedron Letters* (1986) 3919–3922; Brown D. S. et al. "Preparation of cyclic ether acetals from 2-benzenesulphonyl derivatives: a new mild glycosidation procedure." *Tetrahedron Letters* (1988) 29/38:4873–4876; Ito Y. et al. "Benzeneselenenyl triflate as a promoter of thioglycosides: a new method for O-glycosylation using thioglycosides," *Tetrahedron Letters* (1988) 10614; Dasgupta F. et al. "Alkyl sulfonyl triflate as activator in the thioglycoside-mediated formation of β-glycosidic linkages during oligosaccharide synthesis," *Carbohydrate Research* (1988) 177:c13–c17.) However, none of these reported methods teach the use of a glycosyl sulfoxide as a glycosylating agent.

Utilization of an activated glycosyl sulfoxide intermediate in a process for glycosylating steroids, has been reported previously by the inventors in an article that appeared in the *J. Am. Chem. Soc.* (1989) 111:6881–2, the entire contents of which are incorporated by reference herein. However, the reported method represents only preliminary results on the glycosylation of steroids of the Formula (I). More specifically, further experimentation in the series has revealed unique reaction conditions that are necessary to achieve the efficient and stereoselective synthesis of glycosylated compounds of the Formula (I). In particular, it has been discovered that the reaction solvent plays a critical role in the stereoselectivity of glycosylation. Using a non-polar, aprotic solvent increases selectivity for alpha ($\alpha$) glycosidic bond formation while the use of a polar, aprotic solvent such as propionitrile increases selectivity for beta ($\beta$) glycosidic bond formation.

The type of sulfoxide used in the glycosylation reaction also affects the outcome of the reaction. For example, it is vital to use the para-methoxy phenyl sulfoxide as the leaving group in the novel process described herein to obtain good yields of beta ($\beta$) selectivity in the glycosidic bond formation. The yield of the glycosylation reaction yielding alpha ($\alpha$) or beta ($\beta$) glycosidic linkages also may be increased by using less than one equivalent of triflic anhydride in the glycosylation process.

Finally, the identity of the protecting groups present on the glycosyl donor also have an impact on the stereochemical course of the glycosylation reaction. When the protecting group used is pivaloyl, only beta ($\beta$) glycosidic bonds are formed in the glycosylation process, regardless of whether an aprotic, non-polar solvent or an aprotic, polar solvent is used for the reaction. The above-recited factors taken together indicate that one skilled in the art could not have practiced the invention without the detailed further experimentation provided herein.

SUMMARY OF THE INVENTION

The present invention is generally directed to novel, facially-amphiphilic, glycosylated steroid derivatives which have been found to be soluble in both hydrophilic aqueous media and hydrophobic membrane-like environments. These unique solubility properties permit the glycosylated steroid derivatives to facilitate the transport of other molecules across biological membranes, including the blood brain barrier. It is, therefore, contemplated that the glycosylated steroid derivatives of the present invention can be used, either in admixture with the therapeutically-significant-molecules or by being conjugated to such molecules, to enhance delivery of the molecules across body surfaces including, but not limited to, the buccal, sublingual, conjunctival, rectal, gastric, intestinal, endometrial, cervical, vaginal or colonic epithelium; the oropharynx, ear canal, respiratory tract, nasopharynx, urethra, urinary bladder, and tympanic membrane. Alternatively, the glycosylated steroid derivatives of the present invention may be administered in admixture with the glycosylated steroid derivative/therapeutically-significant-molecule conjugate (hereinafter referred to as the "derivative-compound-conjugate" or simply "conjugate") to further enhance facilitation of trans-surface and trans-membrane transport.

It is further contemplated that the novel glycosylated steroids of the present invention may be used for the delivery of antiviral agents, systemic insecticides, and herbicides, across plant surfaces; and, for the delivery of contact insecticides and miticides, across arthropod surfaces.

A novel process for obtaining these novel, facially amphiphilic, glycosylated steroid derivatives and other glycosylated steroids is also disclosed.

Of particular interest are the steroid derivatives of the general Formula (I):

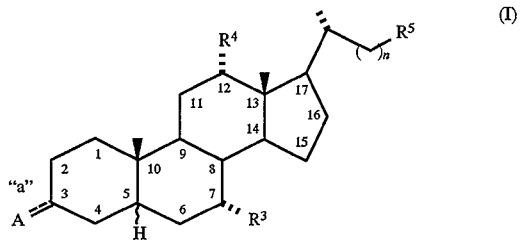

wherein

A is H, O, OH, OR$^6$, NR$^7$R$^8$, N$_3$, NHCOR$^7$, OCOAr, O—CO—OR$^9$, O—CO—R$^9$, NCH$_2$C$_6$H$_5$, and in which Ar is phenyl or phenyl substituted with 1–3 groups selected from the group consisting of halogen, C1–C$_{12}$ alkyl or C$_1$–C$_3$ alkoxy;

"a" is a single bond in the alpha or beta configuration with the proviso that when A=O, a is a double bond;

R$^3$ is H, OH or OR$^6$;

R$^4$ is H, OH or OR$^6$;

R$^5$ is CO$_2$R$^{10}$, CH$_2$OR$^9$, CONH$_2$, CONHR$^7$, CONR$^7$R$^8$, CO—S—R$^{10}$, CH$_2$S(O)$_p$—S—R$^{10}$, CH$_2$NH$_2$, CH$_2$NHR$^7$, CH$_2$NR$^7$R$^8$, CH2—S(O)$_p$—S—R$^{10}$;

R$^6$ is glycosyl moiety comprising 1–10 monosaccharide units in which the glycosidic linkage at the anomeric carbon atom of each monosaccharide unit is independently alpha or beta;

R$^7$ and R$^8$, independently are H, C$_1$–C$_4$ alkyl, C$_3$–C$_7$ cycloalkyl, C4–C$_{10}$ alkylcycloalkyl, phenyl, benzyl, or, taken together are (CH$_2$)$_f$, where f=3–6;

R$^9$ is H or C$_1$–C$_3$ alkyl;

R$^{10}$ is H, C$_1$–C$_{10}$ alkyl, C$_1$–C$_{10}$ alkenyl, C$_1$–C$_{10}$ alkynyl, C$_6$H$_5$ or CH$_2$C$_6$H$_5$;

p is 0, 1 or 2;

n is 0, 1 or 2;

or a pharmaceutically-suitable salt thereof. In specific embodiments of the present invention, particular compounds of the Formula (I), in which at least one, preferably two, and most preferably all three of A, R$^3$, and R$^4$ cannot be H, are preferred.

In the instant invention, the monosaccharide is a protected or deprotected sugar residue. For example, the monosaccharide may be a hexose or deoxyhexose selected from the group consisting of D- or L-allose, D- or L-altrose, D- or L-glucose, D- or L-mannose, D- or Lgulose, D- or L-idose, D- or L-galactose, and D- or L-talose. The monosaccharide may further be a protected or deprotected furanose or deoxyfuranose selected from the group consisting of D- or L-ribose, D- or Larabinose, D- or L-xylose and D- or L-lyxose. The protecting groups for the hydroxy groups of the hexoses or furanoses may be any appropriate for the conditions of the contemplated reactions or other use but are preferably selected from the group consisting of benzyl, pivaloyl, trimethylsilyl, tertbutyldimethylsilyl, tertbutyldiphenylsilyl, tri-isopropylsilyl, acetyl, tetrahydropyranyl, benzoyl, C$_1$–C$_3$alkyl, isopropylidene, benzylidene, (2-methoxyethoxy)methyl, orthoester, paramethoxybenzyl and allyl.

Of further interest are conjugates comprising the compound of Formula (I) covalently linked to a second compound. For example, the second compound can be a therapeutically-significant-compound that is linked directly or indirectly to a compound of Formula (I) via any of the appropriate functional groups present in the compound of Formula (I) which can accommodate a covalent bond, including but not limited to the substituent at C3 (e.g., through any of groups contemplated for or equivalent to "A"), C7 (e.g., through any of groups contemplated for or equivalent to $R_3$), C12 (e.g., through any of groups contemplated for or equivalent to $R^4$) or C17 (e.g., through any of groups contemplated for or equivalent to the side-chain substituent $R^5$). While the identity of the compound of therapeutic significance is limited only by its chemical compatibility with the glycosylated steroid derivatives of the present invention, the following therapeutically-significant-compounds are representative: anti-bacterials such as polyene antibiotics (erythromycin), beta-lactam antibiotics (cefadroxil), and peptide-based or steroidal antibiotics; anti-fungal agents such as 10-thiastearic acid and 24-thiacholestanol; peptides, polypeptides or proteins, such as regulatory factors, enzymes, antibodies, hormones, and toxins; nucleotides, nucleosides and nucleic acids; and saccharides.

Even though the present invention is not limited by the nature or identity of the second compound that is covalently linked to the compound of Formula (I), certain compounds of Formula (I) are preferred, especially those that contain at least one, preferably two, most preferably three hydroxyl groups. In the conjugates of the present invention, such hydroxyl groups are preferably in an alpha stereochemical configuration. In addition, the hydroxyl groups may bear one or more, preferably two, glycosyl moieties.

It is pointed out that the A and B rings of the steroidal skeleton of the compounds of Formula (I) may be cis or trans to one another, and that the O glycosidic linkage at C7 and C12 may be in the alpha or beta configuration, each independently of the other. Hence, the present invention provides methods for facilitating the transport of any therapeutically-significant-compound across a biological membrane, either in admixture with a glycosylated steroid derivative of the present invention or in the form of a derivative-compound-conjugate. Alternatively, a method is provided for further enhancing trans-membrane transport of the derivative-compound-conjugate by administering the derivative-compound-conjugate in admixture with a glycosylated steroid derivative of the present invention, which may be either the same as, or different from, the derivative of the conjugate.

Also provided are pharmaceutical compositions containing (1) an effective amount of a compound of the Formula (I) and a pharmaceutically-acceptable carrier; (2) an effective amount of a compound of Formula (I), an effective amount of a therapeutically-significant-compound, and a pharmaceutically-acceptable carrier; (3) an effective amount of derivative-compound-conjugate and a pharmaceutically-acceptable carrier; or (4) an effective amount of a compound of Formula (I), an effective amount of derivative-compound-conjugate, and a pharmaceutically-acceptable carrier.

The invention is further directed to a novel process for the efficient synthesis of glycosylated steroid derivatives of the Formula (I) which comprises: allowing a protected glycoside, which is prepared by standard methods well known to those of ordinary skill in the art in which the oxygen atoms at all positions of the sugar, except the anomeric position, are protected with the same or different protecting groups, to react with an —S—R entity under standard conditions, in which R is $C_1$–$C_{10}$ alkyl, pyridyl, furyl, thienyl, phenyl or phenyl substituted with 1–3 groups selected from the group comprising halogen, $C_1$–$C_3$ alkyl, $NO_2$, $C_1$–$C_3$ alkoxy, to yield a protected thio-glycoside; the protected thioglycoside is then allowed to react with meta-chloroperoxybenzoic acid to yield the corresponding sulfoxide derivative; the sulfoxide derivative is then converted to an "activated" intermediate (capable of donating a glycosyl group) using an activating agent, preferably a triflate-containing compound, such as triflic anhydride, methyl triflate or trimethylsilyl triflate; the "activated" intermediate is then contacted with asteroid containing a free hydroxyl group (any other steroid hydroxyl groups which are not to be glycosylated are protected by standard methods) in the presence of 2,6-di-tert-butyl4-methylpyridine in toluene solvent (for formation of alpha,alpha glycosidic linkages) or in propionitrile solvent (for the formation of beta,beta glycosidic linkages), thereby yielding a protected glycosylated steroid, which is then deprotected by standard procedures to yield the glycosylated steroids of the Formula (I).

The oxygen(hydroxyl)-protecting groups utilized may be either electron-withdrawing groups such as esters; or electron-donating groups, such as ethers, including alkyl, silyl, phenyl or benzyl ethers. However, if a pivaloyl ester is used as the protecting group, the resulting glycosidic linkage that is formed is always $\beta,\beta$ regardless of the solvent used for the reaction. The resulting compounds of the invention may be characterized by proton NMR, C-13 NMR, high resolution mass spectroscopy, X-ray crystallography, thin layer chromatography, and the like.

It is also an object of the present invention to provide compounds, compositions, and methods for the transformation of cells, both prokaryotic and eukaryotic. Indeed, by contacting cells with nucleic acids (in any form, including, but not limited to, single-stranded, double-stranded, linear, closed circular, plastmids, vectors, phages, constructs, chromosomes or their fragments) in the presence of selected compounds or conjugates of the present invention, transformed cells can be obtained in which the nucleic acid has been introduced to or incorporated in the cell.

Also provided are methods for the synthesis of the novel derivative-compound-conjugates of the present invention.

Preferred for their ability to permeabilize biological membranes are those compounds of Formula (I) in which A is OH, $OR^6$, O—CO—$R^9$, $OCOC_6H_5$, $OCOC_6H_5$—pOMe, $NH_2$; "a" is a single bond; $R^3$ is $OR^6$; $R^4$ is $OR^6$; $R^5$ is $CO_2R^{10}$, $CONR^7R^8$; $R^6$ is a monosaccharide in which the glycosidic linkage at the anomeric carbon atom in the monosaccharide is alpha or beta; $R^7$, $R^8$, and $R^9$ are as defined above; $R^{10}$ is H or $C1$–$C_{10}$ alkyl; and the monosaccharide is a protected or deprotected hexose, such as D- or L-glucose, and further, where the protecting groups are benzyl or pivaloyl.

Preferred for their ability to permeabilize biological membranes are:

(i) 3α-O-benzoyl-trans-5,10-bis-β,β-7,12-glucosyl cholic acid methyl ester;

(ii) 3α-hydroxy-cis-5,10-bis-α,α-7,12-glucosyl cholic acid;

(iii) 3α-hydroxy-cis-5,10-bis-α,α-7,12-glucosyl cholic acid methyl ester;

(iv) 3α-hydroxy-cis-5,10-bis-α,α-7,12-glucosyl-25-tryptophanyl cholic acid;

(v) 3α-ethylcarbonate-cis-5,10-bis-α,α-7,12-glucosyl cholic acid methyl ester;

(vi) 3α-O-benzoyl-cis-5,10-bis-α,α-7,12-glucosyl cholic acid methyl ester;

(vii) 3α-O-p-methoxybenzoyl-cis-5,10-bis-α,α-7,12-glucosyl cholic acid methyl ester;

(viii) 3α-O-benzoyl-cis-5,10-bis-β,β-7,12-glucosyl cholic acid methyl ester;

(ix) 3α-hydroxy-cis-5,10-bis-β,β-7,12-glucosyl cholic acid;

(x) 3α-O-benzoyl-trans-5,10-bis-α,α-7,12-glucosyl cholic acid methyl ester;

(xi) 3α-hydroxy-trans-5,10-bis-β,β-7,12-glucosyl cholic acid; and (xii) 3β-amino-7α,12α-di-(1'-α-glucosyl)-5β-cholic acid methyl ester, its free acid or acid salt forms.

Particularly preferred is compound (g), 3α-O-p-methoxybenzoyl-cis-5,10-bis-α,α-7,12-glucosyl cholic acid methyl ester (CME) and its acid form, 3α-O-p-methoxybenzoyl-cis-5,10-bis-α,α-7,12-glucosyl cholic acid and compound (1), 3β-amino-7α,12α-di-(1'-α-glucosyl)-5β-cholic acid methyl ester, its free acid or acid salt forms. According to the present invention, a cationic metal salt derivative of the steroid acid is an alkali or alkaline earth metal salt of the acid, including but not limited to sodium, potassium, magnesium, calcium salts, and the like. The ester or amide derivative may be an aliphatic or aromatic ester or amide, although the amide may be a simple amide, i.e., —CONH$_2$. Preferably, the ester or amide is an aliphatic, most preferably a lower alkyl ($C_1$–$C_4$) ester or amide.

DESCRIPTION OF THE DRAWINGS

FIG. 19. Plot of plasma calcitonin concentration over time obtained from rats ileally administered with calcitonin in the presence of varying amounts of compound 1, as illustrated in the Figure.

DETAILED DESCRIPTION OF THE INVENTION

Figure 1:
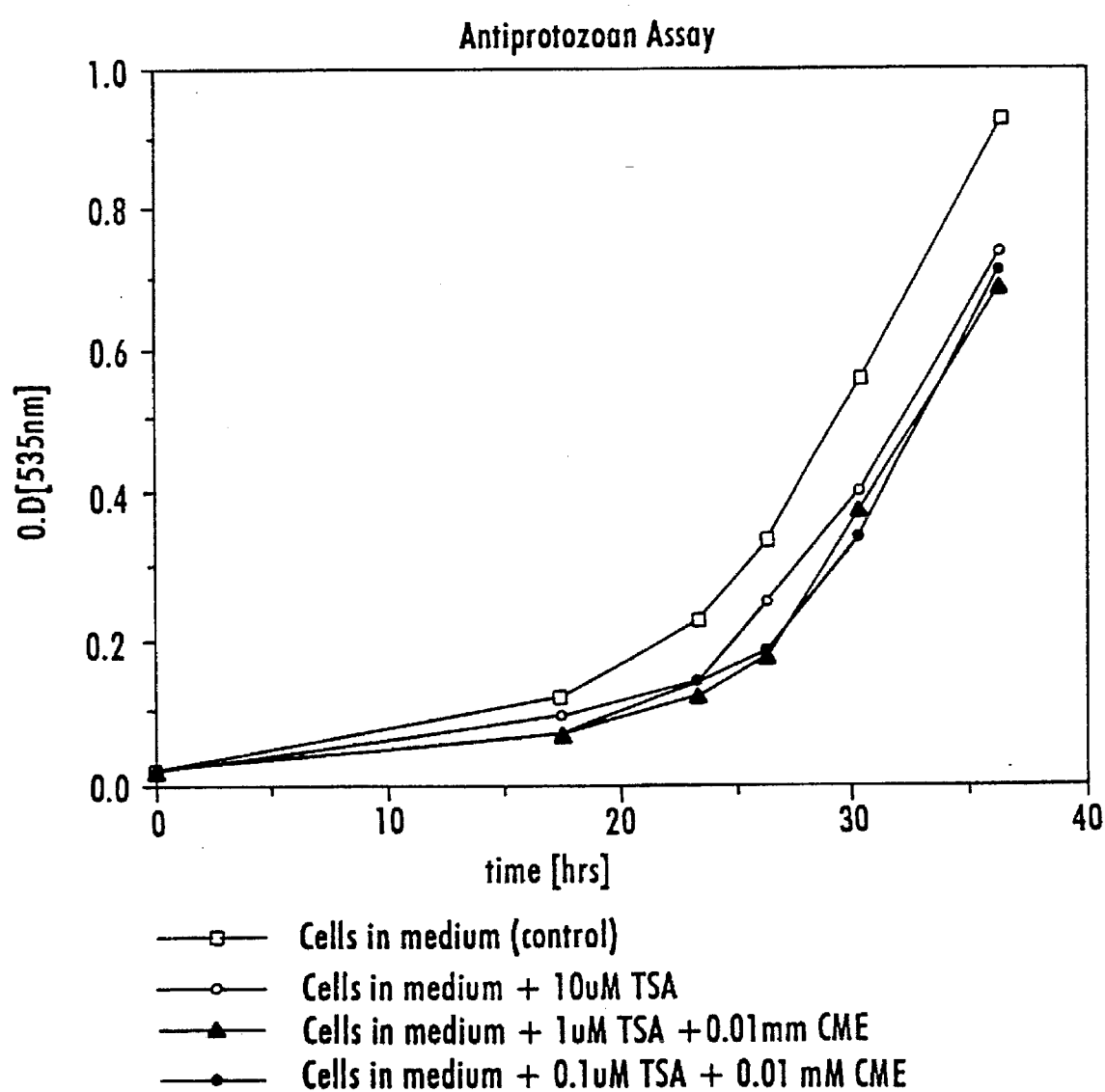
FIG. 1. A graph depicting the enhancing effect of CME, a novel glycosylated steroid derivative of the present invention, on the efficacy of thiastearic acid (TSA), an antifungal agent.

The introduction of molecules of diagnostic, prophylactic or therapeutic interest across body surfaces and/or into cells requires the traversal of one or more semipermeable biological membranes. The compounds of this invention are useful in permeabilizing biological membranes, thereby assisting body surface and/or membrane transversal of therapeutically-significant-compounds. In one embodiment, the therapeutically-significant-compound is administered in admixture with a glycosylated steroid derivative of the present invention. In another embodiment, trans-surface and/or trans-membrane transport is facilitated by administering the therapeutically-significant-compound in the form of a derivative-compound-conjugate in which the compound of interest is conjugated to the glycosylated steroid, e.g., by linking the therapeutically-significant-compound via the group $R^5$ or by any suitable manner that would be apparent to one of ordinary skill in the art. Further, the derivative-compound-conjugate may be administered in admixture with a novel glycosylated steroid derivative of the present invention, which may be either the same as, or different from, the derivative of the conjugate. The novel glycosylated steroid derivatives of the present invention may be expected to enhance the therapeutic efficacy of a wide variety of compounds. As a result, many therapeutic applications for the compounds of the present invention may be contemplated. Membrane permeable therapeutic agents could be used in the treatment of a wide variety of illnesses including AIDS and other chronic viral infections, cancer, bacterial and fungal infections, and metabolic diseases such as lupus, diabetes and rheumatoid arthritis. The ability of the novel glycosylated steroid derivatives of the present invention to interact with, and/or permeabilize, biological membranes, is believed to result from the compounds' facial amphiphilicity. The glycosylated surface of the derivatives is hydrophilic; the non-glycosylated surface is hydrophobic. This facially amphiphilic structure confers unusual properties on the molecules, including an ability to self-associate in both hydrophobic and hydrophilic environments, and to organize at amphiphilic interfaces. Some of the glycosylated steroid derivatives of the present invention have now been shown, by the inventors, to crystallize in layers, with alternating hydrophobic and hydrophilic layers. The non-glycosylated, parent steroid compounds, although possessing some facial amphiphilicity, do not crystallize in register and in organized layers like the glycosylated steroids. In addition, the solubility properties of the glycosylated steroid derivatives of the present invention differ substantially from those of the parent compounds. More particularly, the novel glycosylated steroid derivatives of the present invention, while more soluble than the parent compounds in an aqueous environment are, unexpectedly, not significantly less soluble than the parent compounds in an organic environment.

Based on these observations, the inventors believe (although not wishing to be limited by theory) that the novel glycosylated steroid derivatives of the present invention permeabilize membranes by self-associating to form small, reverse micelles, with their hydrophobic surfaces exposed to the lipids within the membranes. These reverse micelles may function as water-filled pores, allowing therapeutically-significant-compounds to pass through. Alternatively, the presence of these reverse micelles in the membrane may perturb membrane order enough to permit passage of the compounds of therapeutic significance.

Additionally, the compounds of the present invention facilitate the transport of protons or other ions such as $Ca^{2+}$, $Na^+$ or $K^+$ across biological membranes, indicating their use as potential antifungal or antibiotic agents.

The derivative-compound-conjugates of the present invention can be used in vivo, as a component of a pharmaceutical composition in a manner similar to that used for more conventional therapeutic agents. Administration to an individual with a chronic viral infection of the derivative-compound-conjugate comprising an antiviral agent and the glycosylated steroid derivative of the present invention may inactivate the virus by, for example, taking advantage of the antiviral agent's ability to inhibit an enzyme necessary for viral replication. Alternatively, the derivative-compound-conjugate may contain an antisense oligonucleotide sequence such as one known to be effective in inhibiting viral gene function or oncogenic activity. For the individual with a genetic defect, the therapeutically-significant-compound can be a protein that supplements a missing or defective protein or in a gene-therapy approach, introduces a nucleic acid that can supply the missing or defective indigenous gene.

The derivative-compound-conjugate may be administered as a pharmaceutical composition via a variety of routes, including subcutaneous, intravenous, intramuscular, intrasternal, intranasal, intraperitoneal, and intracranial injection or infusion. The pharmaceutical composition also may be administered topically or via inhalation.

More specifically, the compounds of this invention in combination with known therapeutically-significant-compounds, including the derivative-compound-conjugates comprising the compounds of Formula (I), can be administered to prevent, diagnose or treat a whole host of human, veterinary and even plant ailments. Thus, in combination with zidovudine or AZT, currently approved for the treatment of AIDS (or others, such as DDI, which are under development or awaiting regulatory approval) or 1-(2'-deoxy-2'-fluoro-β-D-arabinofuranosyl)-5-iodocytosine (FIAC), 1-(2'-deoxy-2'-fluoro-β-D-arabinofuranosyl)-5-iodouracil (FIAU) or 1-(2'-deoxy-2'-fluoro-β-D-arabinofuranosyl)-5-methyluracil (FMAU), nucleoside analogs useful for inhibiting or arresting a wide range of viral infections (as disclosed, for example, in U.S. Pat. No. 4,594,339, the complete disclosure of which is incorporated by reference herein), the present invention is useful for the treatment of AIDS and other chronic viral infections, including hepatitis, herpes simplex, and the like.

By judicious choice of therapeutically-significant compound, other medical conditions or ailments can likewise be prevented, diagnosed or treated. Such conditions or diseases include, but are not limited to, autoimmune diseases, such as lupus, rheumatoid arthritis, and diabetes. Other potential indications include cystic fibrosis, cancer and genetic deficiencies, such as growth hormone deficiencies. The compositions of the present invention can be administered by any conventional means available for use in conjunction with pharmaceuticals, either as individual preparations of therapeutic agents or in a combination of more than one therapeutic agent. The compositions can be administered alone, but are generally administered with a pharmaceutically acceptable carrier selected on the basis of the chosen route of administration and standard pharmaceutical practice.

In a preferred embodiment of the present invention, conjugates comprising compounds of the Formula (I) covalently linked to antisense oligonucleotides are contemplated.

Thus, a drug therapy method is contemplated which utilizes glycosteroid-oligonucleotide conjugates for the effective delivery of antisense oligonucleotides across biological membranes. Most preferably bis-glycosylated steroid membrane permeation enhancers are conjugated to antisense oligonucleotide sequences known to inhibit viral (e.g., HIV) replication to provide an effective anti-viral drug therapy. This conjugation is accomplished, for example, by attaching to the oligonucleotide, either by its 5'- or 3'-terminus, to a glycosylated steroid, preferably, via a linker to the steroid C-17 side chain. The new conjugates are found to exhibit an enhanced efficacy to bind to predetermined target sense sequences in a cell as will be shown by both in vitro and in vivo studies. The development of this technology which provides the reliable deliver of antisense oligonucleotides both across cellular and mucosal membranes promises to fulfill the long-awaited anticipated benefits of antisense oligonucleotide drug and gene therapy.

EXPERIMENTAL DESIGN AND METHOD:

Conjugation of Oligonucleotides to Glycosylated Steroids

Several linkers can be introduced at both the 5'- and 3'-ends of the oligonucleotide. Preferably, the chemical synthesis of the oligonucleotide is carried out on a polymer support (e.g., controlled pore glass) in a 3'- to 5'-direction. Hence, it is convenient, in this case, to modify the 5'-end. The 3'-end can be modified, of course, but a controlled pore glass support will need to be derivatized accordingly.

The preferred method involves the introduction of an amino linker at either end of the oligonucleotide for subsequent conjugation to the carboxylic acid functionality on the side chain of a glycosylated steroid as shown in scheme 1. Presently, derivatization of the glycosylated steriod is preferably carried out on the C17 side chain because it is suspected that the 3-position (or A ring) of the steroid might be playing a major role in the cell penetration enhancer properties of the glycosylated steroid. It is apparent, however, that conjugation can be accomplished through any substituent that can accommodate a covalent bond (e.g., a substituent on C3, C7, C12, or the side chain substituent on

SCHEME 1

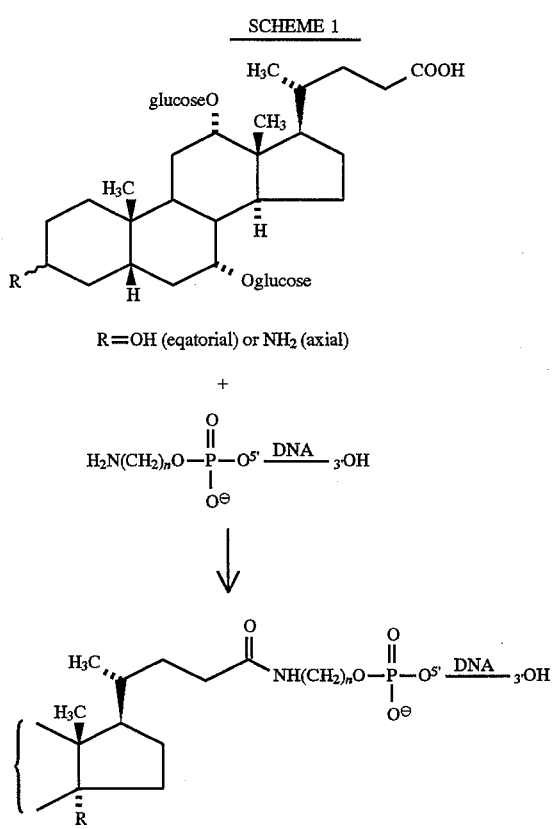

R = OH (eqatorial) or NH₂ (axial)

Design and Synthesis of an Oligonucleotide Sequence

In view of the results obtained by Zamecnik, Letsinger and Caruthers (See, for example, Goodchild, J. et al. *Proc. Nat'l. Acad. Sci. USA* (1988) 85:5507–5511; Letsinger, R. L. et al. *Ibid.* (1989) 86:6553–6556; Marshall, W. S. and Caruthers, M. H. *Science* (1993) 259:1564–1570, the disclosures of which are incorporated by reference herein) in the use of selective antisense oligonucleotide sequences for inhibition of HIV replication, the following preferred sequences were identified, one corresponding to the primer binding site ("PBS") and the other to the splice acceptor site (5349–5368) of the HIV genome:

5' ACA CCC AAT TCT GAA AAT GG 3'
splice acceptor (SAS)                    (SEQ. ID NO:1)

3' TGT GGG TTA AGA CTT TTA CC 5' complement

5' AAG TCC CTG TTC GGG CGC CA 3'
primer binding site (PBS)                (SEQ. ID NO:2)

3' TTC AGG GAC AAG CCC GCG GT 5' complement

The splice acceptor sequence (SEQ. ID NO:1) and the primer binding site sequence (SEQ. ID NO:2) are synthesized with linkers at either the 3'- or 5'-termini. The complements are synthesized without linkers. The complement is synthesized for melting temperature experiments to determine the stability of the duplex before and after conjugation with the glycosylated steroid. The duplex is also desirable for NMR studies to confirm the presence of the amide linkage between the oligonucleotide and the steroid. The syntheses are carried out on an ABI DNA synthesizer using the solid-phase cyanoethylphosphoramidite triester coupling approach developed by Beaucage and Caruthers (S. L. Beaucage, M. H. Caruthers, *Tet. Lett.*, 22, 1859–1862 (1981).) The final dimethoxytrityl ("DMTr") protecting group is left on. The oligonucleotides are then cleaved from the polymer support in NH₄OH at room temperature and fully deprotected after incubation at 55° C. overnight. The hydrophobicity of the dimethoxytrityl protecting group allows easy purification of the desired oligonucleotide by reverse-phase HPLC. The purified oligomer is detritylated and isolated by ethanol precipitation.

An amino linker can be introduced either at the 5'- or 3'-terminus of the oligonucleotide. As stated earlier, because the synthesis of DNA is carried out in a 3'- to 5'-direction (the 3'-end is linked to a polymer support), it is more convenient to introduce an amino linker at the 5'-end of the oligonucleotide. Furthermore, the introduction of the linker can best be carried out using the phosphoramidite chemistry where the commercially available reagents 1 and 2 are used:

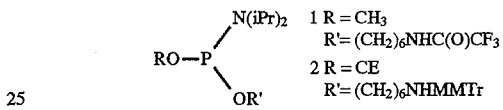

The aminolink 2 reagent (B. J. Bruce, *J. Pharm. Sci.*, 82, 979–987 (1993).) from ABI lacks a protecting group on the amine for easy monitoring of the extent of coupling as well as for purification by RP HPLC. The trifluoroacetyl protecting group is cleaved under the basic conditions required for cleavage of the oligomer from the polymer support. The selective cleavage of the MMTr group while the oligonucleotide is still attached to the polymer support allows conjugation of the glycosylated steroid using solid-phase chemistry.

Several other reagents have been used by different researchers over the years. The length of the linker between the amino functionality and the glycosylated steroid may be varied. Reagent 3 might be of interest for that purpose. It is synthesized using the chemistry summarized in Scheme 2.

SCHEME 2

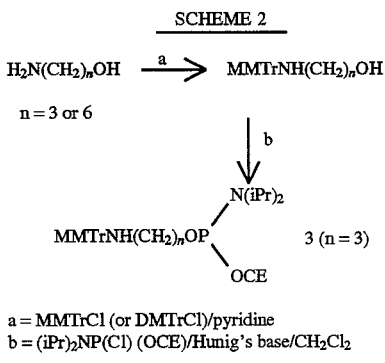

a = MMTrCl (or DMTrCl)/pyridine
b = (iPr)₂NP(Cl) (OCE)/Hunig's base/CH₂Cl₂

The introduction of an amino functionality at the 3'-terminus of an oligonucleotide requires the functionalization of the controlled pore glass (CPG) polymer support. Suitable procedures are known (See, for example, U. Asseline, N. T. Thuong, *Tet. Lett.*, 31, 81–84 (1990) and U. Asseline, E. Bonfils, R. Kurfurst, M. Chassignol, V. Roig, N. T. Thuong, *Tetrahedron*, 48, 1233–1254 (1992)) for functionalization of the support allowing introduction of an amine functionality. The functionalization of the support can be carried out as summarized in Scheme 3.

SCHEME 3

DMTrOCH$_2$CH$_2$SSCH$_2$CH$_2$OH  4

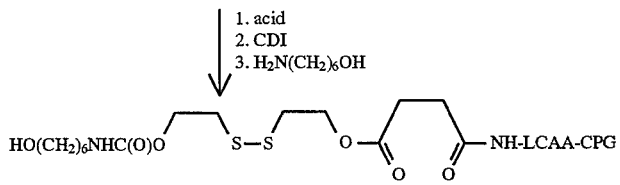

DMTrOCH$_2$CH$_2$SSCH$_2$CH$_2$OC(O)CH$_2$CH$_2$C(O)NH-LCAA-CPG

| 1. acid
| 2. CDI
| 3. H$_2$N(CH$_2$)$_6$OH
↓

HO(CH$_2$)$_6$NHC(O)O~~~S—S~~~O—[succinate]—NH-LCAA-CPG

The functionalization of the support can also be accomplished using a modified procedure developed by Damha and co-workers (M. J. Damha, P. A. Giannaris, S. V. Zabarylo, *Nucl. Acids Res.*, 18, 3813–3821 (1990)) which involves reaction of succinic anhydride with the polymer support and subsequent reaction with compound 4 in the presence of DEC. After functionalization of the support, the oligonucleotide is then synthesized using the cyanoethylphosphoramidite triester coupling approach.

It is found that upon treatment with DTT-NH$_4$OH at the end of the synthesis, both the cleavage of the disulfide bridge and elimination of ethylenesulfide and carbon dioxide occurs (See Scheme 4) to afford the free amino group together with the removal of the cyanoethyl group from the internucleotide phosphate and the acyl groups from the nucleic base. This method for introduction of an amino functionality at the 3'-terminus of an oligonucleotide will generate the same type of linkage that was introduced earlier at the 5'-end of an oligonucleotide. This similarity allows us to directly compare the permeation enhancer properties of conjugated glycosylated steroid-oligonucleotide whether the linkage is at the 3'- or 5'-terminus of the oligomer.

SCHEME 4

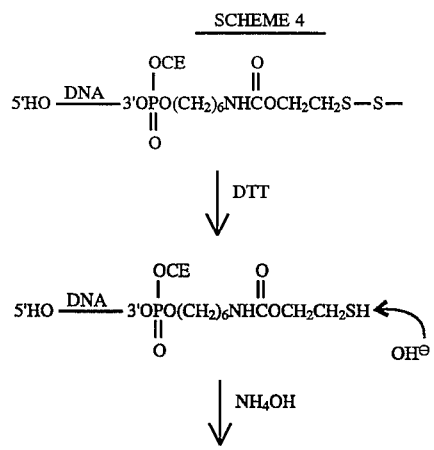

-continued
SCHEME 4

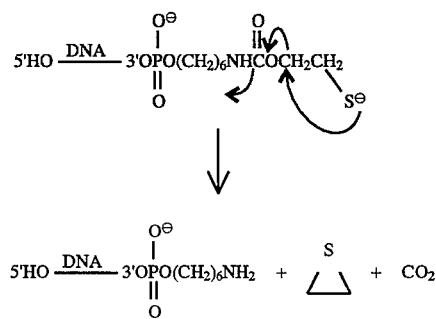

5'HO—DNA—3'OPO(CH$_2$)$_6$NH$_2$  +  [ethylene sulfide]  +  CO$_2$

The conjugation of a glycosylated steroid to an amino-linked oligonucleotide can be carried out two ways: conjugation in solution or on a polymer support. Several reports have been published in the literature regarding the conjugation of biotin to oligonucleotides in solution (S. Agrawal, C. Christodoulou, M. J. Gait, *Nucl. Acids Res.*, 14, 6227–6245 (1986); L. Wachter, J-A. Jablonski, K. L. Ramachandran, *Nucl. Acids Res.*, 14, 7985–7994 (1986); J. M. Coull, H. L. Weith, R. Bischoff, *Tet. Lett.*, 27, 3991–3995 (1986); R. K. Gaur, *Nucleosides and Nucleotides*, 10, 895–909 (1991).) Thus, the N-hydroxysuccinimide derivative of biotin dissolved in DMF and the oligonucleotide dissolved in HEPES or Tris-HCl buffer are mixed together and stirred at room temperature from 1 to 24 hours. The resulting product is purified by RP (i.e., reverse phase) HPLC. One report has also been published on the conjugation reaction carried out on a polymer support (B. D. Gildea, J. M. Coull, H. Koster, *Tet. Lett.*, 31, 7095–7098 (1990)).

To achieve conjugation on a polymer support, the amino-linked oligonucleotide is prepared preferably using the Peninsula Labs reagent in which a MMTr group is present on the amino functionality. The oligonucleotide (still linked to CPG) is detritylated and treated with the N-hydroxysuccinimide derivative of the steroid of interest in CH$_3$CN/DIEA/H$_2$O (8/1/1, v/v/v) (Scheme 5). The resulting product is cleaved off of the support and deprotected in NH$_4$OH at 55° C. overnight.

To achieve conjugation in solution, the amino-linked oligonucleotide is synthesized using either the aminolink 2 reagent or the Peninsula Labs reagent. Using the aminolink 2 reagent, one needs to be able to achieve conjugation on the reaction mixture generated from the final deprotection of the synthesized oligonucleotide since the purification of that amino-linked oligonucleotide can only be achieved by anion-exchange HPLC with difficult separation from the failure sequences. Using the Peninsula Labs reagent, one can use the MMTr group for purification of the amino-linked oligonucleotide by RP HPLC prior to conjugation to the desired steroid. Using this solution phase method, one removes excess DMF, followed by desalting prior to purification by RP HPLC, especially on a large scale.

If one carries out conjugation on a polymer support, filtration of the reagents followed by deprotection in $NH_4OH$, only requires concentration of the ammonium hydroxide solution prior to purification. Thus, the solid-phase conjugation results in a much easier work-up.

The N-hydroxysuccinimide derivative of the steroids of interest are synthesized as shown in Scheme 6. Cholic acid methylester, its analogs and their glycosylated derivatives are treated with NaOH in order to generate the acid. The acid is then treated with N-hydroxysuccinimide in DMF in the presence of DCC to yield the desired activated acid (J. M. Becker, M. Wilchek, *Biochim. Biophys. Acta*, 264, 165–170 (1972).) The N-hydroxysuccinimide derivatives are then conjugated to the 5'-amino-linked oligonucleotide, preferably using solid-phase chemistry. If the $NH_2$ group of analog (xii) is a problem during coupling, it can be protected with a BOC group which can be cleaved under acidic conditions at the end of the synthesis. The same protocol can be used for any other cell penetration enhancers of the present invention.

SCHEME 5

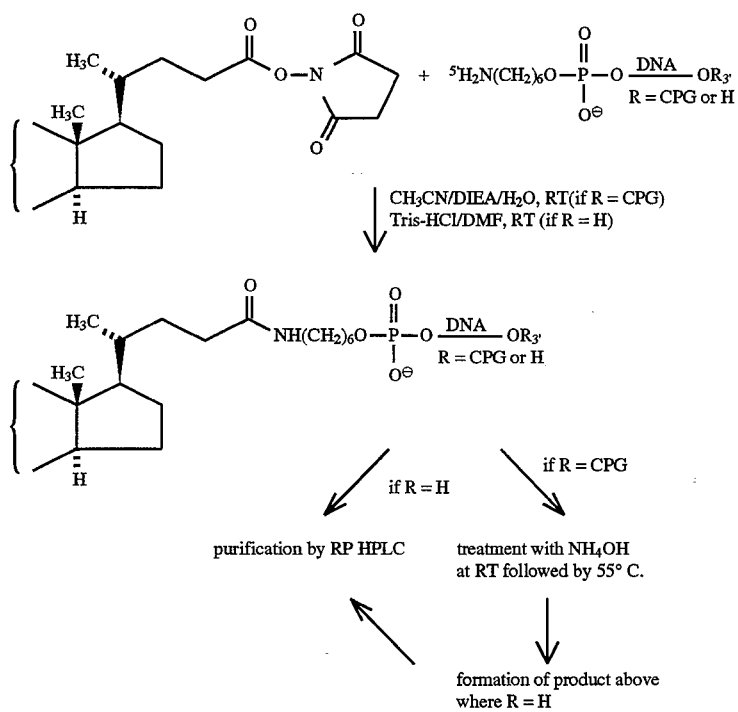

SCHEME 6

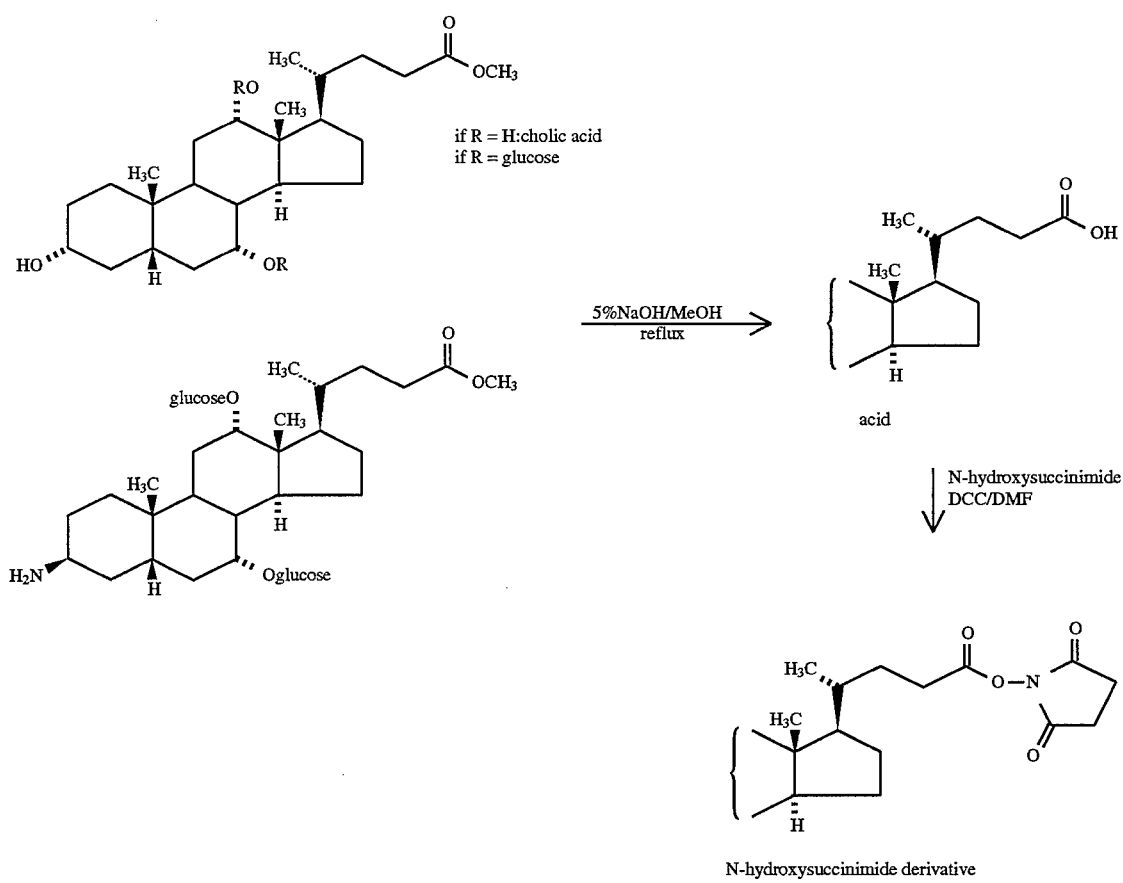

N-hydroxysuccinimide derivative

The conjugation of the 3'-amino linked oligonucleotide with the glycosylated steroids can only be accomplished in solution. However, the desired amino-linked oligonucleotide can easily purified by RP HPLC because of the presence of the DMTr group at the 5'-end. The conjugation reaction can then be carried out in solution and the desired conjugated species purified by RP HPLC. Since the amino linker is present in all failure sequences, purification prior to conjugation will be advisable.

Melting Temperature Experiments and Stability Studies

The stability of the duplex can be studied via melting temperature experiments to determine what effect the conjugated glycosylated steroid has on antisense-sense oligonucleotide recognition (See, for example, R. L. Letsinger, G. Zhang, D. K. Sun, T. Ikeuchi, P. S. Sarin, Proc. Natl. Acad. Sci. (USA), 86, 6553–6556 (1989).) The following compounds are presently of interest:

Compound 1: SAS sequence (SEQ ID. NO:1)+complement (duplex)
  5' ACA CCC AAT TCT GAA AAT GG 3'
  3' TGT GGG TTA AGA CTT TTA CC 5'
Compound 2: 5'-amino linked SAS sequence (SEQ. ID. NO:2)+complement (duplex)
  5' $H_2N(CH_2)_6OP(O)_2$ ACA CCC AAT TCT GAA AAT GG 3'
  3' TGT GGG TTA AGA CTT TTA CC 5'
Compound 3: cholic acid-SAS (SEQ. ID NO:1) conjugated species
Compound 4: Analog iii-SAS (SEQ ID NO:1) conjugated species
Compound 5: Analog xii-SAS (SEQ ID NO:1) conjugated species
Compound 6: PBS sequence (SEQ ID NO:2)+complement (duplex)
  5' AAG TCC CTG TTC GGG CGC CA 3'
  3' TTC AGG GAC AAG CCC GCG GT 5'
Compound 7: 5'-amino linked PBS sequence (SEQ ID NO:2)+complement (duplex)
  5' $H_2N(CH_2)_6OP(O)_2$AAG TCC CTG TTC GGG CGC CA 3'
  3' TTC AGG GAC AAG CCC GCG GT 5'
Compound 8: cholic acid-PBS (SEQ ID NO:2) conjugated species
Compound 9: Analog iii-PBS (SEQ ID NO:2) conjugated species
Compound 10: Analog xii-PBS (SEQ ID NO:2) conjugated species Compounds 3, 4, 5, 8, 9, and 10, above, are used in the duplex form for melting temperature experiments. The presence of the glycosylated steroid on the oligonucleotide does not significantly affect the stability of the duplex as indicated by the absence of significant changes in melting temperature. Compounds 3, 4, 5, 8, 9, and 10, all single-stranded, are further tested in an antiviral assay and in their enhanced ability to cross cell membranes.

Using several commercially available nucleases, the stability imparted by the conjugate to the oligonucleotide is tested.

Dosage and Dosage Forms

The dosage administered will, of course, vary depending upon known factors such as the pharmacodynamic characteristics of the particular prophylactic, diagnostic or therapeutic agent; its mode and route of administration; age, health, and weight of the recipient; nature and extent of symptoms; kind of concurrent treatment; the frequency thereof; and the effect desired. Typically, however, a daily dosage of therapeutically-significant-compound can be about 0.1 to 100 milligrams per kilogram of body weight. Ordinarily 0.5 to 50, and preferably 1 to 10 milligrams per kilogram per day given in divided doses 1 to 6 times a day or in sustained release form is effective to obtain desired results. Still in other situations, a low dose of about 0.1 to about 5 mg, preferably about 0.25 to about 0.75 mg, administered once or twice a day regardless of the weight of the subject may be more appropriate.

Dosage forms (compositions) suitable for internal administration contain from about 1 milligram to about 500 milligrams of therapeutically-significant-compound per unit. In these pharmaceutical compositions the therapeutically-significant-compound ordinarily will be present in an amount of about 0.5–95% by weight based on the total weight of the composition. In the low dosage use, single dose units containing about 0.1 to about 1 mg, preferably about 0.25 to about 0.5 mg, of active ingredient are also provided.

The compositions can be administered orally in solid dosage forms, such as capsules, tablets, and powders, or in liquid dosage forms, such as elixirs, syrups, and suspensions. The compositions also can be administered parenterally, in sterile liquid dosage forms, by inhalation in the form of a nasal spray or lung inhaler, or topically as an ointment, cream or lotion.

Gelatin capsules additionally may contain powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of therapeutically-significant compound over a period of hours. Compressed tablets can be sugar-coated or film-coated to mask any unpleasant taste and protect the tablet from the atmosphere, or enteric-coated for selective disintegration in the gastrointestinal tract and, preferably, within a predetermined section thereof.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration additionally may contain suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl or propyl-paraben, and chlorobutanol.

EXAMPLES

The compounds of Formula (I) can be prepared according to the process shown in Scheme A.

SCHEME A

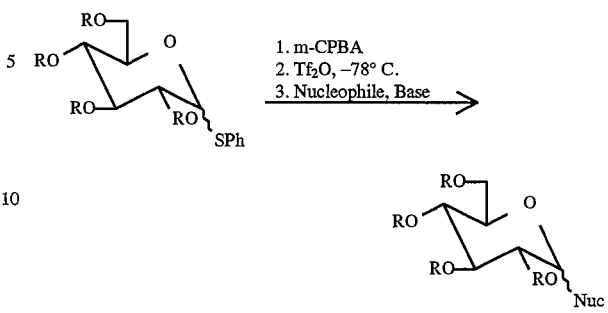

A protected thioglycoside is oxidized with m-chloroperoxybenzoic acid under standard conditions to yield the corresponding sulfoxide. Triflic anhydride (Aldrich) is then added to a solution of the protected glycosyl sulfoxide in toluene at −78° C. followed by the addition of an acid scavenger such as 2,6-di-tert-butyl-4-methyl pyridine (Aldrich Chemical Co.) in toluene and the nucleophile dissolved in toluene at −78° C. After stirring for 15–30 minutes, the reaction was removed from the cold bath and stirred for an additional 10 minutes and quenched by pouring the mixture into aqueous sodium bicarbonate and the protected adduct was isolated by chromatography. Deprotection of the adduct under standard conditions yields compounds of the Formula (I). The appropriate thioglycoside is obtained via standard protection of a selected sugar followed by thioglycoside formation according to methods described above. Via this method, bis-glycosylation of asteroid derivative of the Formula (I) where $R^3$ and $R^4$ are OH selectively produces $\alpha,\alpha$ glycosidic linkages with the glycosyl donor, except where the protecting group used is pivaloyl, in which case only $\beta,\beta$ glycosidic linkages are formed regardless of the solvent used for the reaction. Alternatively, the protected glycosyl sulfoxide, nucleophile and pyridine base are dissolved in propionitrile at −78° C., followed by the addition of triflic anhydride at −78° C. and the product is isolated as described above. Via this method, glycosylation of asteroid derivative of the Formula (I) where $R^3$ and $R^4$ are OH selectively produces $\beta,\beta$ glycosidic linkages with the glycosyl donor. It is vital to use the p-methoxy phenyl sulfoxide as the leaving group in the above process to obtain the $\beta,\beta$ selectivity in the glycosylation.

The compounds of this invention and their preparation are illustrated further in the following examples. All temperatures are in degrees Centigrade and parts and percentages by weight. In these Examples, unless otherwise indicated, the reactions were performed under an atmosphere of dry argon; "isolation by extraction" refers to the liquid-liquid extraction of a water containing mixture with an indicated solvent, followed by drying the organic phase over sodium sulfate, filtering, and evaporating the solvent under reduced pressure; chromatography refers to the method of medium pressure column chromatography described by W. C. Still, et al. *J. Org. Chem.* (1978) 43:2923.

Example 1

Part A

Perbenzylated-3α-ethylcarbonatecis-5,10-bis-α,α-glucosyl cholic acid methyl ester A 100 ml round bottom flask containing a Teflon® stir bar is flame dried and cooled to −78° C. (acetone/dry ice bath)

under argon. 2,3,4,6-tetra-Obenzyl glucose sulfoxide (2.97 g, 4.57 mmol, 4.0 eq.), C3-ethylcarbonate cholic acid (0.563 g, 1.14 mmol, 1.0 eq.) and 2,6-di-tert-butyl-4-methylpyridine (0.936 g, 4.57 mmol, 4.0 eq.) are each dried by azeotroping each separately three times with toluene (15.0 ml). Triflic anhydride (824 µl, 4.57 mmol, 4.0 eq.) is added to the glycosyl sulfoxide dissolved in toluene (5.0 ml) at −78° C. To this mixture is then added the pyridine base in toluene (5.0 ml). After five minutes, the cholic acid derivative, dissolved in methylene chloride (1.0 ml) and toluene (5.0 ml) is added. The reaction is allowed to stir at −78° C. for thirty minutes and then removed from the dry ice bath. After ten minutes, the reaction is quenched by the addition of saturated sodium bicarbonate and the product is isolated by extraction with methylene chloride and purified by flash chromatography on silica gel to provide the title compound (60%) as an oil. $R_F$=0.3 (20% ether/$CH_2Cl_2$).

Example 1

Part B

3α-ethylcarbonate-cis-5,10-bis-α,α-glucosyl cholic acid methyl ester

Palladium hydroxide (0.030 g, 15% by weight) is added to a mixture of the product of Part A (0.220 g, 0.014 mmol, 1.0 eq.) dissolved in benzene (4.0 ml) and methanol (32.0 ml) at room temperature. The mixture is hydrogenated at 50 psi for 48 hours. The product is filtered through Celite® (diatomaceous silica, Johns-Manville Corp.) under nitrogen. The solvent is evaporated, and the oil is flash chromatographed with 10% methanol/methylene chloride. To remove the silica gel that dissolves under elution conditions, the product is run through on a reverse phase LH-20 column using methanol as an eluent. The solvent is evaporated to yield the title compound (65%) as a white powder. $R_F$=0.3 (15% MeOH/$CH_2Cl_2$). NMR ($CDCl_3$ 500 MHz) δ: 5.04 (m, 1H, anomeric β-H), 4.82 (m, 1H, anomeric β-H).

Example 2

3α-benzoyl-cis-5,10-bis-α,α-glucosyl cholic acid methyl ester 2,3,4,6-tetra-O-benzyl p-methoxy glucose sulfoxide (1.012 g, 1.45 mmol, 4.0 eq.), C3-O-benzoyl cholic acid methylester (0.191 g, 0.364 mmol, 1.0 eq.) and 2,6-di-tert-butyl-4 methyl pyridine (0.179 g, 0.874 mmol, 2.4 eq.) are azeotroped together three times from toluene (20 ml). After removing the toluene under reduced pressure for the last time, the mixture is dissolved in freshly distilled propionitrile and cooled under argon in a dry ice/acetone bath at −78° C. Triflic anhydride (244 µl, 1.45 mmol, 4.0 eq.) is added and the reaction mixture is stirred at −78° C. for 40 minutes. The reaction vessel is removed from the ice bath and stirred for an additional 10 minutes. The reaction is quenched by pouring it into saturated sodium bicarbonate and the product is isolated by extraction with methylene chloride and purified by flash chromatography on silica gel. Catalytic hydrogenation to remove the benzyl protecting groups is accomplished as described above to yield the title compound (60%) as an oil. $R_F$=0.3 (15% MeOH/$CH_2Cl_2$). NMR ($CDCl_3$ 500 MHz) δ: 4.36 (d, 1H, J=7.92Hz, anomeric-α-H), 4.37 (d, 1H, J=7.92Hz, anomeric-α-H).

Example 3

2,3,4,6-Tetra-O-benzyl-α-D-glucopyranose (2)

Methyl-α-D-glucopyranose (100 g, 0.516 mol) is suspended in benzyl chloride (400 mL, 3.5 mol) with KOH pellets (336 g, 6 mol), and the mixture is stirred using a mechanical stirrer at 120°–130° C. for 3 h, as shown in Scheme B. The reaction mixture is cooled and water (800 mL) is added to dissolve the crystalline mass, which is extracted with ether (2×200 mL). The combined organic layer is washed with water (2×500 mL) and dried ($Na_2SO_4$). The solvents are removed by vacuum distillation to give the crude methyl 2,3,4,6-tetra-O-benzyl-α-D-glucopyranoside for the next reaction.

SCHEME B

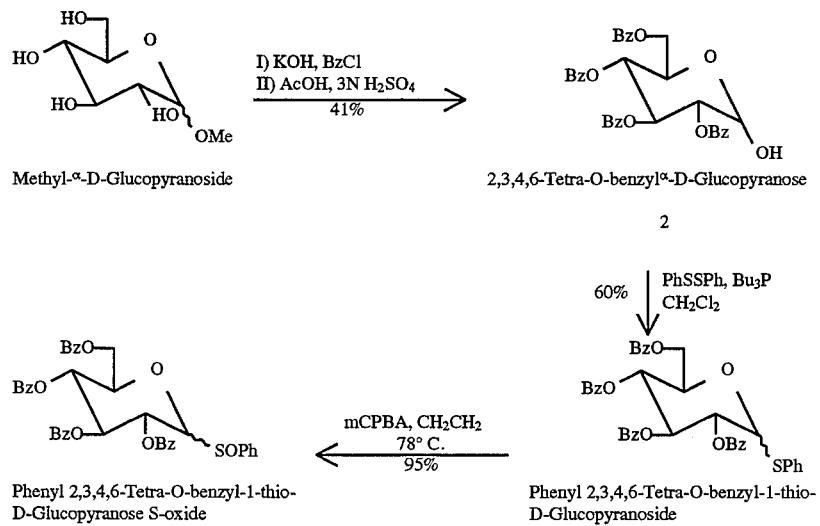

-continued
SCHEME B

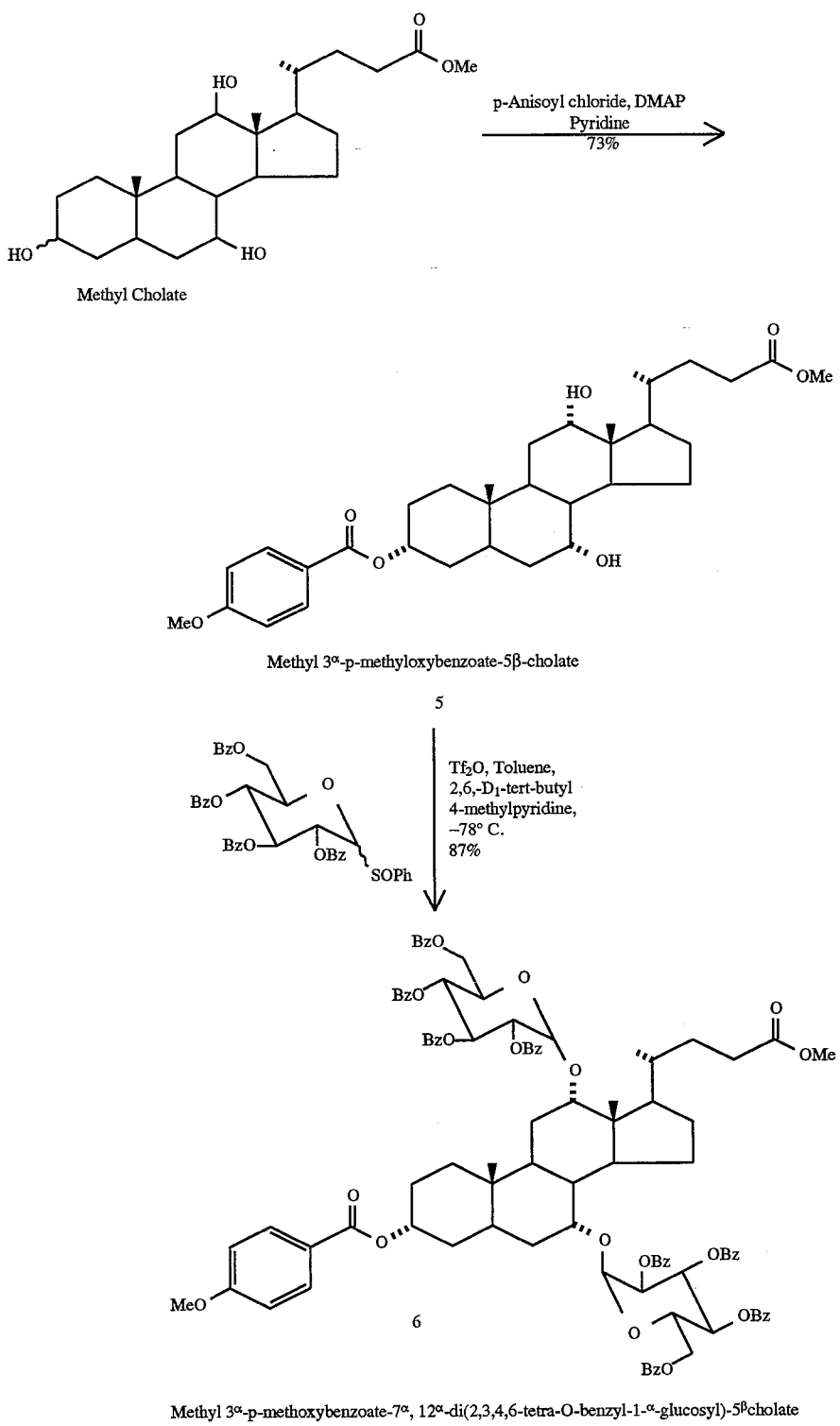

To a stirred solution of above crude compound in glacial acetic acid (700 mL) at 110° C. is added 3N sulfuric acid (120 mL) dropwise during 15 min. After 3 h the reaction mixture is cooled to room temperature and left over night for crystalization of product. The crystals are filtered, washed consecutively with water (4×500 mL) and methanol (2×250 mL), and air dried to afford 2 (115 g, 41% overall two steps) as a white powder (mp 150°–51° C., Lit. 151°–152° C.; See, Perrine, T. D. et al. *J. Org. Chem.* (1967) 32:664). TLC $R_f$=0.2 (solvent—EtOAC: Hexane=3:7). IR (KBr): 3362, 3030, 2911, 2863, 1454, 1357, 1146, 1088 cm$^{-1}$. $^1$H NMR (300 MHz, CDCl$_3$): 7.38–7.10 (m, 20H), 5.21 (d, J=3.3 Hz, 1H), 4.98–4.44 (m, 9H), 4.25 (m, 1H), 3.72–3.50 (m, 4H).

Anal. Calc. for $C_{34}H_{36}O_6$: C, 75.53; H, 6.71. Found: C, 75.68; H, 6.80.

Example 4

Phenyl 2,3,4,6-tetra-O-benzyl-1-thio-D-glucopyranoside (3)

To a stirred solution of 2 (108 g, 0.2 mol) and phenyl disulfide (53 g, 0.24 mol) in dichloromethane (500 mL) is added tri-n-butylphosphine (60 mL, 90%, 0.22 mol). After allowing the reaction mixture to stir at room temperature for 15 h, it is poured into a solution of saturated aqueous sodium bicarbonate (600 mL) and stirred for 10 min. The organic layer is separated, washed with water (2×500 mL), dried ($Na_2SO_4$) and concentrated. The oily residue is dissolved in hexane (500 mL) and chilled to 0° C. to give compound 3 (75 g, 60%) as a white solid (mp 85°–86° C., Lit. 84°–85° C. for β-thio compound; See, Ferrier, R. J. et al. *Carbohyd. Res.* (1973) 27:55). TLC $R_f$=0.6 (solvent—EtOAC:Hexane= 1:3). IR (KBr): 3061, 3030, 2900, 2865, 1584, 1494, 1453, 1358, 1125, 1085, 1070, 1029 $cm^{-1}$. $^1H$ NMR (300 MHz, $CDCl_3$): 7.70–7.00 (m, 25H), 4.90–4.40 (m, 9H), 3.80–3.40 (m, 6H). Anal. Calc. for $C_{40}H_{40}O_5S$: C, 75.92; H, 6.38, S, 5.06. Found: C, 75.99; H, 6.39; S, 5.12.

Example 5

Phenyl 2,3,4,6-tetra-O-benzyl-1-thio-D-glucopyranoside S-oxide (4)

To a stirred cooled (−78° C.) solution of 3 (130 g, 0.2 mol) in dichloromethane (400 mL) is added dropwise over a period of 20 min a solution of mCPBA (74%, 58.31 g, 0.25 mol) in dichloromethane (300 mL). The mixture is stirred and allowed to warm up to −30° C. The mixture is then filtered. The filtrate is washed with saturated aqueous sodium bisulfite (2×300 mL), sodium bicarbonate (2×400 mL), brine (400 mL) and water (2×400 mL). The organic layer is dried ($Na_2SO_4$) and concentrated. Flash chromatography ($CH_2Cl_2$:EtOAC=9:1) of the residue furnishes sulfoxide mixture 4 (127 g, 95%) as a white solid (mp 120°–122° C.). TLC $R_f$=0.3 (solvent—EtOH:$CH_2Cl_2$=1:9). IR (KBr): 3060, 3030, 2910, 2867, 1495, 1450, 1360, 1210, 1136, 1092, 1049 $cm^{-1}$. $^1H$ NMR ($CDCl_3$): 7.72–7.14 (m, 25H), 5.12–4.42 (m, 9H), 4.40–3.30 (m, 6H). Anal. Calc. for $C_{40}H_{40}O_6S$: C, 74.04; H, 6.22; S, 4.93. Found: C, 74.10; H, 6.26; S, 4.99.

Example 6

Methyl 3α-p-methoxybenzoate-5β-cholate (5)

A solution of methyl cholate (42.2 g, 0.1 mol), p-anisoyl chloride (20 mL, 0.133 mol) and DMAP (1 g) in pyridine (500 mL) is stirred and refluxed for 8 h. Additional p-anisoyl chloride (10 mL, 0.67 mol) is addded and stirred 12 h. The reaction mixture is concentrated, and the residue is dissolved in dichloromethane (600 mL). The solution is washed consecutively with 1N HCl (2×500 mL) and water (3×500 mL), dried ($Na_2SO_4$) and the solvent allowed to evaporate. Crystallization of the residue from EtOAC/hexane (1:1) furnishes 5 (40 g, 72%) as a white solid (mp 179°–180° C.). TLC $R_f$=0.7 (solvent—EtOAC:Hexane=7:3).

Example 7

Methyl 3α-p-methoxybenzoate-7α,12α-di-(2',3',4', 6'-tetra-O-benzyl (1'-α-glucosyl)-5β-cholate (6)

Triflic anhydride (30 mL, 0.178 mol) is added to cooled toluene (300 mL, −78° C.) and stirred for 5 min. To this solution, a dried (by azeotropic distillation from toluene) sulfoxide 5 (97 g, 0.1495 mol) dissolved in toluene (300 mL) is added dropwise. After 15 min of stirring, a solution of dried (by azeotropic distillation with toluene) 2,6-di-ter-butyl-4-methyl-pyridine (30.8 g, 0.150 mol) in toluene (100 mL) is added to the reaction mixture and stirred for 10 min at −78° C. To this reaction mixture, dried (by azeotropic distillation with toluene) methyl cholate derivative 5 (33.36 g, 0.06 mol) in $CH_2Cl_2$ and toluene (1:1, 200 mL) is added dropwise. The reaction progress is monitored by TLC. The temperature of the reaction mixture is slowly brought to −50° C. (during 45 min) and during this time the spot of 5 on the TLC disappears completely. The reaction mixture is poured into a saturated aqueous solution of sodium bicarbonate (1000 mL) and stirred for 10 min. The organic layer is separated, and the aqueous layer is extracted with dichloromethane (2×100 mL). The combined organic layers is washed with water (3×500 mL), dried ($Na_2SO_4$) and concentrated. The residue purified by flash chromatography (EtOAC:Hexane=1:9 to 1:4) to furnish 6 (84 g, 87%) as a white foam (mp 46°–48° C.). TLC $R_f$=0.3 (solvent—EtOAC:Hexane=1:3). IR (KBr): 3084, 3062, 3028, 2936, 2867, 1735, 1707, 1605, 1496, 1453, 1360, 1321, 1275, 1254, 1210, 1165, 1097, 1073, 1030 $cm^{-1}$. $^1H$ NMR ($CDCl_3$): 7.60–6.70 (m, 43H), 5.95 (d, 1H, J=9Hz), 4.99 (d, 1H, J=3.6 Hz), 4.93 (d, 1H, 6 Hz), 4.88–3.29 (m, 31H), 2.68–0.65 (m, 37H). Fab MS: 1624 (M+Na)$^+$. Anal. Calc. for $C_{101}H_{116}O_{17}$: C, 75.71; H, 7.30. Found, C, 75.59; H, 7.31.

Example 8

7α,12α-Di-(2',3',4',6'-tetra-O-benzyl-1'α-glucosyl)-5β-cholan-24-oic acid (7)

To a stirred solution of 6 (24 g, 15 mmol) in THF (150 mL), NaOH (10 g, 250 mmol) in 95% Ethanol (200 mL) is added and refluxed for 48 h, as shown in Scheme C. The reaction mixture is then concentrated, and the residue is dissolved in ethyl acetate (300 mL), washed with water (2×250 mL), saturated aqueous sodium bicarbonate (2×300 mL), brine (300 mL) and dried ($Na_2SO_4$). Solvent is evaporated and the resulting compound 7 (18.5 g, 85%) is used for the next step without further purification. TLC $R_f$=0.4 (solvent—EtOAC:Hexane=1:3) 0.4.

SCHEME C
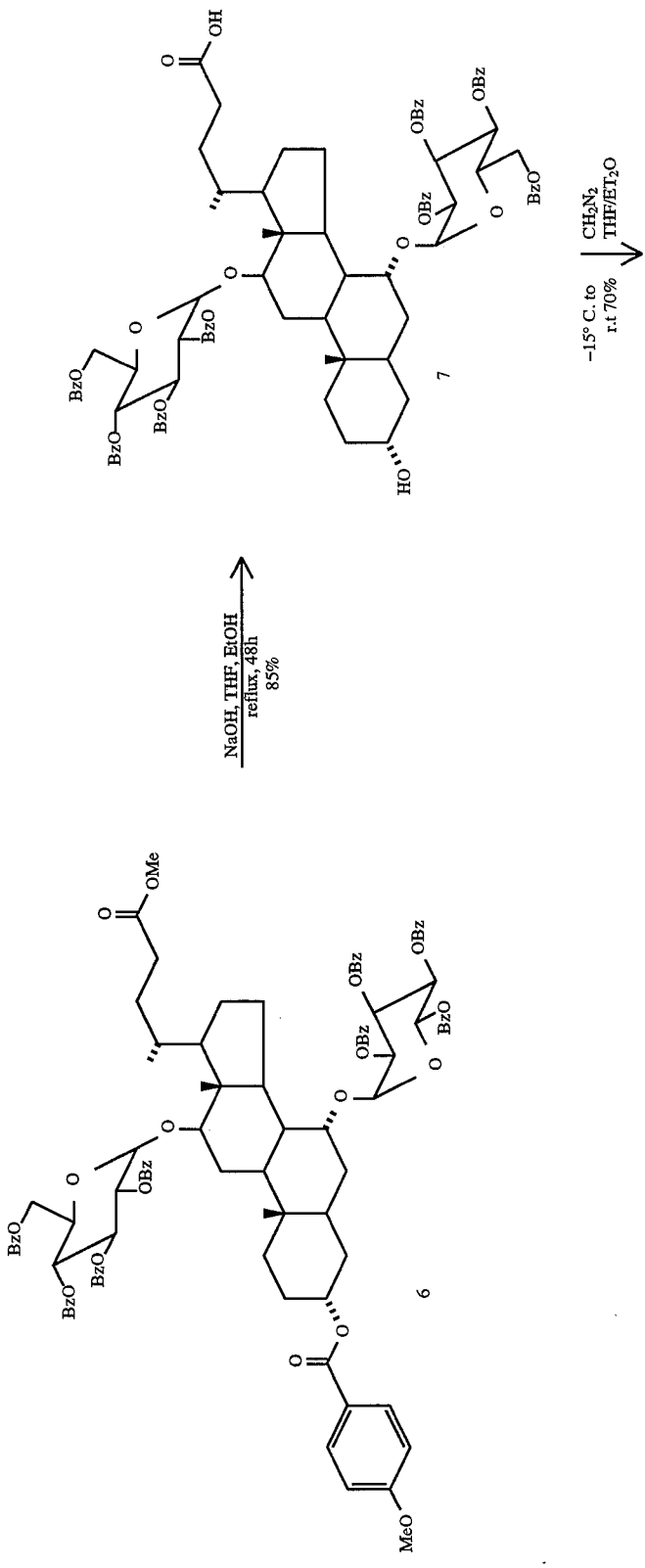

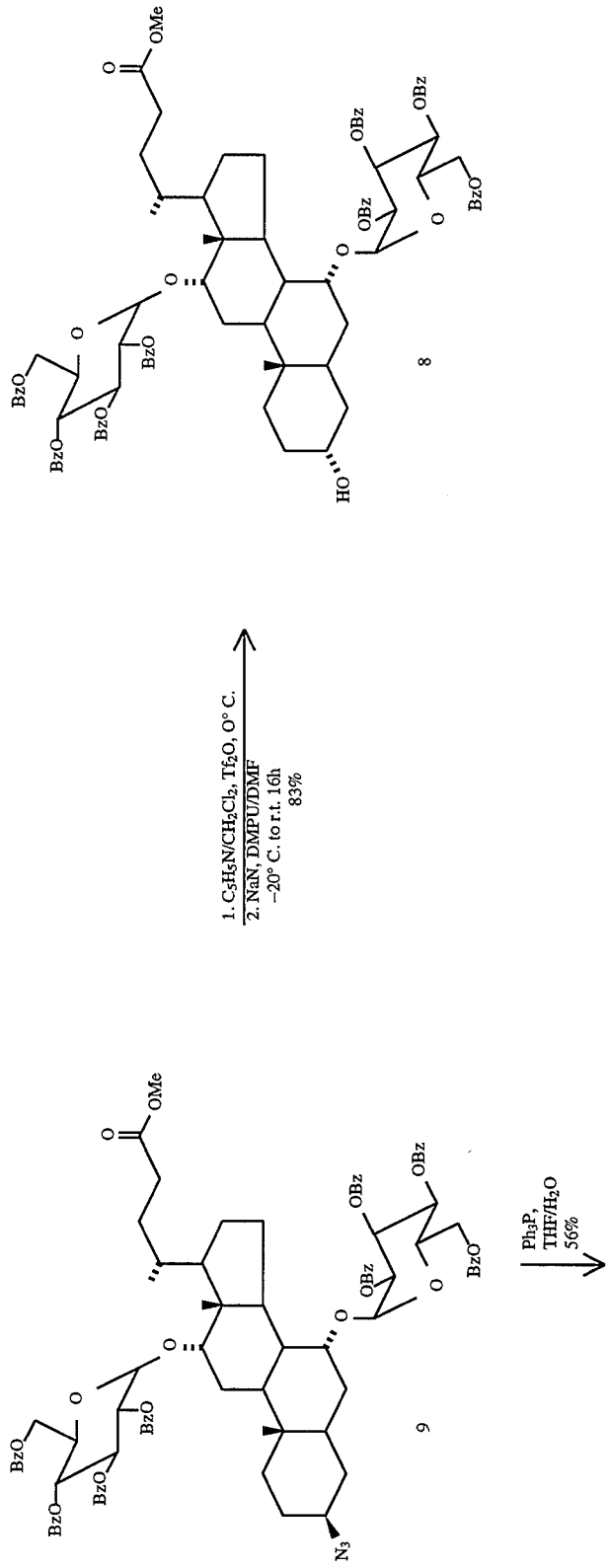

-continued
SCHEME C
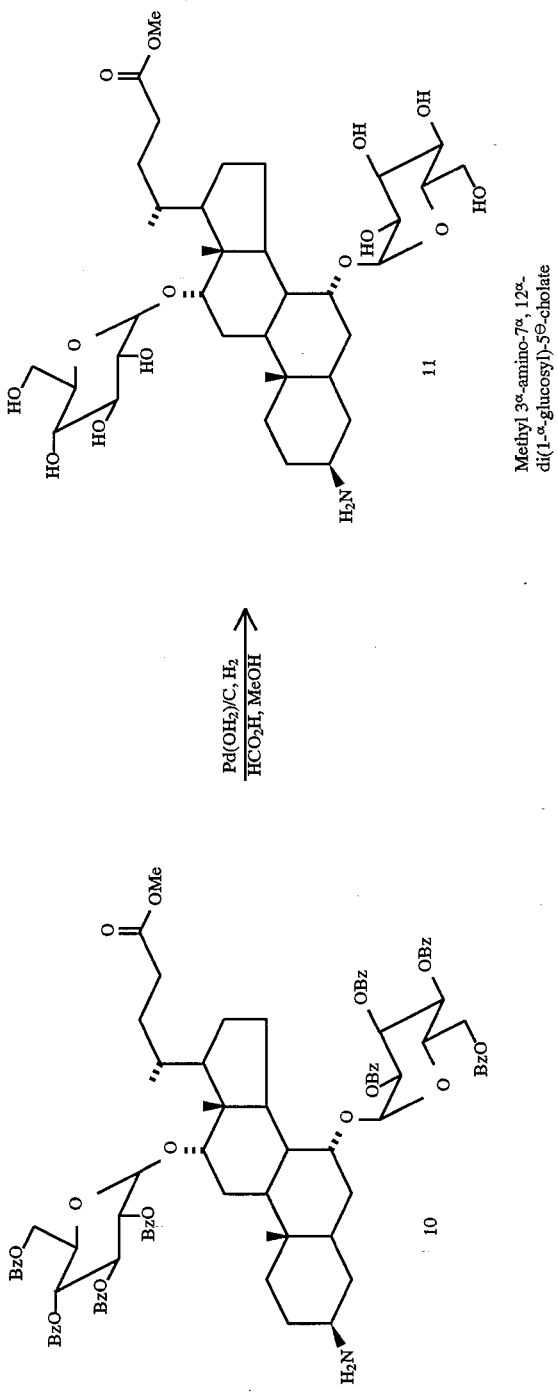

Example 9

Methyl 7α,12α-di-(2',3',4',6'-tetra-O-benzyl-1'-α-glucosyl)-5β-cholate (8)

A cooled (−10° C.) solution of diazomethane in ether (100 mL, generated from 5.35 g of diazalid, 25 mmol) is added to a cooled (−10° C.) solution of 7 (18.5 g, 12.74 mmol) in ether (100 mL). After 1 h, excess diazomethane is destroyed by adding glacial acetic acid (2 mL). The reaction mixture is washed consecutively with saturated aqueous sodium bicarbonate (2×400 mL), brine (300 mL), and water (300 mL), dried ($Na_2SO_4$), and concentrated. The residue is purified by flash chromatography (EtOAC:Hexane=3:17) to furnish 8 (13 g, 70%) as a gum. TLC $R_f$=0.6 (solvent—EtOAC:Hexane=1:3). IR (Neat): 3450, 2925, 2866, 1736, 1453, 1362, 1158, 1071, 1030 $cm^{-1}$. $^1H$ NMR ($CDCl_3$): 7.40–6.50 (m, 40H), 5.10–3.40 (m, 33H), 2.40–0.71 (m, 38H). Anal. Calc. for $C_{93}H_{110}O_{15}$: C, 76.08; H, 7.56. Found: C, 74.79; H, 7.50.

Example 10

Methyl 3β-azido-7α,12α-di-(2',3',4',6'-tetra-O-benzyl-1'-α-glucosyl)-5β-cholate (9)

To a cooled (0° C.) solution of methyl cholate derivative 8 (13 g, 8.87 mmol) and pyridine (2.5 mL, 31 mmol) in dichloromethane (50 mL), triflic anhydride is added and allowed to stir for 20 min. To this mixture, a solution of sodium azide (2.6 g, 40 m/nol) in DMF/DMPU (1:1, 250 mL) is then added at −20° C. The reaction mixture is allowed to warm up to room temperature, where it is stirred overnight. The solvents are evaporated, and the residue is dissolved in dichloromethane (200 mL), washed with water (3×200 mL), dried ($Na_2SO_4$), and concentrated. Flash Chromatography of the residue on silica (EtOAC:Hexane=3:17) furnishes 10g (75%) of 9 as a white solid (mp 112°–114° C.). TLC $R_f$=0.6 (solvent—EtOAC:Hexane=1:4). IR (KBr): 3085, 3061, 3029, 2921, 2867, 2097, 1735, 1603, 1495, 1452, 1360, 1256, 1207, 1160, 1091, 1071, 1031 $cm^{-1}$. $^1H$ NMR ($CDCl_3$): 7.37–6.84 (m, 40H), 5.15 (d, 1H, J=4Hz), 4.95 (d, 1H, 4Hz), 4.86–4.26 (m, 15H), 4.08–3.40 (m, 16H), 2.60–0.71 (m, 37H). Fab MS: 1515 (M+Na)$^+$. Anal. Calc. for $C_{93}H_{110}O_4N_3$: C, 74.76; H, 7.43; N, 2.81. Found: C, 74.84; H, 7.40; N, 2.79.

Example 11

Methyl 3β-amino-7α,12α-di-(2',3',4',6'-tetra-O-benzyl-1'α-glucosyl)-5β-cholate (10)

A solution of compound 9 (11 g, 7.38 mmol) and $Ph_3P$ (5.76 g, 22 mmol) in 90% aqueous THF (100 mL) is stirred and refluxed for 48 h. The reaction mixture is concentrated, and the residue is purified by flash chromatograph ($CH_2Cl_2$ and then $CH_2Cl_2$:EtOH=98:2 to 9:1) to give the 3-amino compound 10 (6 g, 56%) as a white solid (mp 43°–45° C.). TLC $R_f$=0.15 (solvent—EtOH:$CH_2Cl_2$=1:19. IR (KBr): 3418, 2922, 2868, 1736, 1496, 1453, 1362, 1161, 1071, 1032 $cm^{-1}$. $^1H$ NMR ($CDCl_3$): 7.38–6.84 (m, 40H), 5.10–3.48 (m, 33H), 2.62–0.70 (m, 37H). Anal. Calc. for $C_{93}H_{112}O_{14}N$: C, 76.08; H, 7.70; N, 0.95. Found: C, 75.82; H, 7.71; N, 0.89.

Example 12

Methyl 3β-amino-7α,12α-di-(1'-α-glucosyl)-5β-cholate (1)

To a solution of 10 (14.65g, 10 mmol) in toluene (50 mL) and ethanol (200 mL) is added formic acid (15 mL) and palladium hydroxide (20%) on carbon (15 g). The resulting mixture is stirred for 24 h under a hydrogen atmosphere at 40 psi. TLC indicated incomplete hydrogenolysis. Additional formic acid (4 mL) and catalyst (4 g) is then added, and the hydrogenation reaction allowed to proceed for another 24 h. The reaction mixture is then filtered through sand over a membrane filter and concentrated. The filtrate is then mixed with ethyl acetate to form a precipitate. (Some of the methanol solvent from the hydrogenation reaction may need to be removed.) The filtered precipitate is then dissolved in 25 mL deionized water and freezedried. Flash Chromatography gives 2.82 g (38%) of I as white foam (mp 170°–172° C., decomp.). TLC $R_f$=0.15 (solvent—MeOH:$CH_2Cl_2$:Isopropylamine=2:2:1). IR (KBr): 3450, 2932, 1736, 1595, 1451, 1381, 1151, 1023 cm–1. $^1H$ NMR ($CDCl_3$): 5.05 (d, 1H), 4.80 (d, 1H), 3.91–3.10 (m, 15H), 2.50–0.58 (m, 37H). MS (Fab): 746 (M+H)$^+$. Anal. Calc. for $C_{37}H_{63}O_{14}N$: C, 59.56; H, 8.52; N, 1.88. Found: C, 54.60; H, 8.47; N, 2.49.

Example 13

Methyl 3-p-methoxybenzoate-7α,12α-di-(1'-α-glucosyl)-5β-cholate (Entry No. 8$^h$, Table I, Below)

To a solution of 6 (10 mmol; See, Example 7, above) in toluene (50 mL) and ethanol (200 mL) is added formic acid (15 mL) and palladium hydroxide (20%) on carbon (15 g). The resulting mixture is stirred for 24 h under a hydrogen atmosphere at 40 psi. (Additional formic acid and catalyst can be added, if desired, if TLC analysis reveals that the reaction is incomplete after the initial 24 h reaction period. A second 24 h reaction period can then be initiated.) The reaction mixture is then filtered through sand over a membrane filter and concentrated. The filtrate is then mixed with ethyl acetate to form a precipitate. (Some of the methanol solvent from the hydrogenation reaction may need to be removed.) The filtered precipitate is then dissolved in 25 mL deionized water and freeze-dried. Subjecting the residue to flash column chromatography gives the title compound in ca. 38% yield.

$^1H$ NMR ($CD_3OD$): δ0.71 (s, 3H, 18-H), 0.90 (d,J=6.6Hz, 3H, 21-H), 0.93 (s, 3H, 19-H), 1.0–2.6(m), 3.2–3.4 (m, 2H), 3.55 (s, 3H, $CO_2CH_3$), 365(m), 376(s, 3H, anisoyl-4-methyl), 4.83 (d, 1H, anomeric), 5.02 (d, 1H, anomeric), 6.87 (d, J=9Hz, 2H, anisoyl aromatic), 7.92 (d,J=9Hz, 2H, anisoyl aromatic).

Additional compounds that can be prepared following procedures analogous to those outlined above are shown in Table I, including selected mass spectral and proton nmr data.

TABLE I

| Entry No. | A | a* | R¹* | R² | R³** | R⁴** | R⁵ | n |
|---|---|---|---|---|---|---|---|---|
| 1[b] | O=C-OCOEt | s(α) | H(β) | CH₃ | O-glucose(α) | O-glucose(α) | CO₂Me | 2 |
| 2[c] | OCOPh | s(α) | H(β) | CH₃ | O-glucose(β) | O-glucose(β) | CO₂Me | 2 |
| 3[d] | OH | s(α) | H(β) | CH₃ | O-glucose(α) | O-glucose(α) | CO₂H | 2 |
| 4[e] | OH | s(α) | H(β) | CH₃ | O-glucose(α) | O-glucose(α) | CO₂Me | 2 |
| 5[f] | OH | s(α) | H(β) | CH₃ | O-glucose(α) | O-glucose(α) | CONH-Tryptophan | 2 |
| 6 | O=C-OCOEt | s(α) | H(α) | CH₃ | O-glucose(α) | O-glucose(α) | CO₂Me | 2 |
| 7[g] | OCOPh | s(α) | H(β) | CH₃ | O-glucose(α) | O-glucose(α) | CO₂Me | 2 |
| 8[h] | OCOPh—OMe | s(α) | H(β) | CH₃ | O-glucose(α) | O-glucose(α) | CO₂Me | 2 |
| 9[i] | OCOPh | s(α) | H(α) | CH₃ | O-glucose(β) | O-glucose(β) | CO₂Me | 2 |
| 10[j] | OH | s(α) | H(β) | CH₃ | O-glucose(β) | O-glucose(β) | CO₂H | 2 |
| 11[k] | OCOPh | s(α) | H(α) | CH₃ | O-glucose(α) | O-glucose(α) | CO₂Me | 2 |
| 12 | OH | s(α) | H(α) | CH₃ | O-glucose(α) | O-glucose(α) | CO₂H | 2 |
| 13[l] | OH | s(α) | H(α) | CH₃ | O-glucose(β) | O-glucose(β) | CO₂H | 2 |
| 14 | NH₂ | s(α) | H(β) | CH₃ | O-glucose(α) | O-glucose(α) | CO₂H | 2 |
| 15 | O=C-OCOEt | s(α) | H(β) | CH₃ | O-glucose(β) | O-glucose(β) | CO₂Me | 2 |
| 16 | O=C-OCOEt | s(α) | H(α) | CH₃ | O-glucose(β) | O-glucose(β) | CO₂Me | 2 |
| 17 | O | d | H(α) | CH₃ | O-glucose(α) | O-glucose(α) | CO₂H | 2 |
| 18 | O | d | H(α) | CH₃ | O-glucose(β) | O-glucose(β) | CO₂H | 2 |
| 19 | O | d | H(β) | CH₃ | O-glucose(α) | O-glucose(α) | CO₂H | 2 |
| 20 | O | d | H(β) | CH₃ | O-glucose(β) | O-glucose(β) | CO₂H | 2 |
| 21 | O | d | H(α) | CH₃ | O-glucose(α) | O-glucose(α) | CO₂Me | 2 |
| 22 | O | d | H(α) | CH₃ | O-glucose(β) | O-glucose(β) | CO₂Me | 2 |
| 23 | O | d | H(β) | CH₃ | O-glucose(α) | O-glucose(α) | CO₂Me | 2 |
| 24 | O | d | H(β) | CH₃ | O-glucose(β) | O-glucose(β) | CO₂Me | 2 |
| 25 | OCH₂Ph | s(α) | H(α) | CH₃ | O-glucose(α) | O-glucose(α) | CO₂H | 2 |
| 26 | OCH₂Ph | s(α) | H(α) | CH₃ | O-glucose(β) | O-glucose(β) | CO₂H | 2 |
| 27 | OCH₂Ph | s(α) | H(β) | CH₃ | O-glucose(α) | O-glucose(α) | CO₂H | 2 |
| 28 | OCH₂Ph | s(α) | H(β) | CH₃ | O-glucose(β) | O-glucose(β) | CO₂H | 2 |
| 29 | OCH₂Ph | s(α) | H(α) | CH₃ | O-glucose(α) | O-glucose(α) | CO₂Me | 2 |
| 30 | OCH₂Ph | s(α) | H(α) | CH₃ | O-glucose(β) | O-glucose(β) | CO₂Me | 2 |
| 31 | OCH₂Ph | s(α) | H(β) | CH₃ | O-glucose(α) | O-glucose(α) | CO₂Me | 2 |
| 32 | OCH₂Ph | s(α) | H(β) | CH₃ | O-glucose(β) | O-glucose(β) | CO₂Me | 2 |
| 33 | O=C-OCOEt | s(α) | H(α) | CH₃ | O-galactose(α) | O-galactose(α) | CO₂H | 2 |
| 34 | O=C-OCOEt | s(α) | H(α) | CH₃ | O-galactose(β) | O-galactose(β) | CO₂H | 2 |
| 35 | O=C-OCOEt | s(α) | H(β) | CH₃ | O-galactose(α) | O-galactose(α) | CO₂H | 2 |
| 36 | O=C-OCOEt | s(α) | H(β) | CH₃ | O-galactose(β) | O-galactose(β) | CO₂H | 2 |

TABLE I-continued

[steroid structure with substituents A, R¹, R², R³, R⁴, R⁵, n, a]

| Entry No. | A | a* | R¹* | R² | R³** | R⁴** | R⁵ | n |
|---|---|---|---|---|---|---|---|---|
| 37 | O‖OCOEt | s(α) | H(α) | CH₃ | O-galactose(α) | O-galactose(α) | CO₂Me | 2 |
| 38 | O‖OCOEt | s(α) | H(α) | CH₃ | O-galactose(β) | O-galactose(β) | CO₂Me | 2 |
| 39 | O‖OCOEt | s(β) | H(α) | CH₃ | O-galactose(α) | O-galactose(α) | CO₂Me | 2 |
| 40 | O‖OCOEt | s(α) | H(β) | CH₃ | O-galactose(β) | O-galactose(β) | CO₂Me | 2 |
| 41 | OCOPh | s(α) | H(α) | CH₃ | O-ribose(α) | O-ribose(α) | CO₂H | 2 |
| 42 | OCOPh | s(α) | H(α) | CH₃ | O-ribose(β) | O-ribose(β) | CO₂H | 2 |
| 43 | OCOPh | s(α) | H(β) | CH₃ | O-ribose(α) | O-ribose(α) | CO₂H | 2 |
| 44 | OCOPh | s(α) | H(β) | CH₃ | O-ribose(β) | O-ribose(β) | CO₂H | 2 |
| 45 | OCOPh | s(α) | H(α) | CH₃ | O-ribose(α) | O-ribose(α) | CO₂Me | 2 |
| 46 | OCOPh | s(α) | H(α) | CH₃ | O-ribose(β) | O-ribose(β) | CO₂Me | 2 |
| 47 | OCOPh | s(α) | H(β) | CH₃ | O-ribose(α) | O-ribose(α) | CO₂Me | 2 |
| 48 | OCOPh | s(α) | H(β) | CH₃ | O-ribose(β) | O-ribose(β) | CO₂Me | 2 |
| 49 | O‖OCOEt | s(α) | H(β) | CH₃ | O-glucose(α) | O-glucose(β) | CO₂Me | 2 |
| 50 | O‖OCOEt | s(α) | H(β) | CH₃ | O-glucose(β) | O-glucose(α) | CO₂Me | 2 |
| 51 | O‖OCOEt | s(α) | H(α) | CH₃ | O-glucose(α) | O-glucose(β) | CO₂Me | 2 |
| 52 | O‖OCOEt | s(α) | H(α) | CH₃ | O-glucose(β) | O-glucose(α) | CO₂Me | 2 |

*s = single bond
d = double bond
α = below the plane of the ring
β = above the plane of the ring
**α =

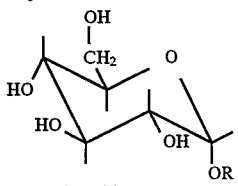

An α-glucoside,
β =

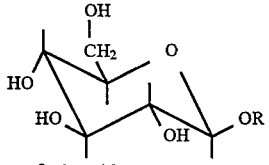

An β-glucoside
Mass Spectra

TABLE I-continued

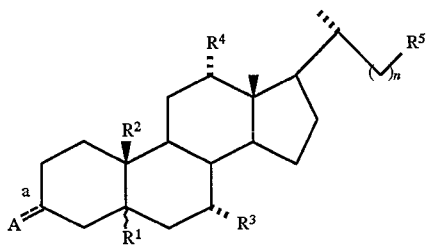

| Entry No. | A | a* | R¹* | R² | R³ | R⁴ | R⁵ | n |
|---|---|---|---|---|---|---|---|---| c m/e = 851
d m/e = 771
h m/e = 881
i m/e = 851
j m/e = 771
k m/e = 851
l m/e = 771

¹H NMR b: (CDCl₃, 500MH$_z$) δ: 5.04(m, 1H, anomeric β-H̲), 4.82(m, 1H, anomeric β-H̲)
e: (CDCl₃, 500MH$_z$) δ: 5.04(m, 1H, anomeric β-H̲), 4.82(m, 1H, anomeric β-H̲)
f: (CDCl₃, 500MH$_z$) δ: 5.056(m, 1H, anomeric β-H̲), 5.0414(m, 1H, anomeric β-H̲)
g: (CDCl₃, 500MH$_z$) δ: 5.0525(d, J=3.96H$_z$, 1H, anomeric β-H̲), 4.860(d, J=3.96Hz, 1H, anomeric β-H̲)

Example 14

Synthesis of the Activated Ester of Deoxycholate

Triethylamine (10 mL, 71.2 mmol) is added to a stirred solution of the sodium salt of deoxycholic acid (15 g, 34.7 mmol), N-hydroxysuccinimide (7.5 g, 65.2 mmol), 1-hydroxybenzotriazole hydrate (9.3 g, 68.8 mmol, HOBT) and 1-(3-dimethylaminopropyl)-3-ethylcarbodiimide (13.2 g, 69.3 mmol, EDC) in dichloromethane. The mixture is stirred for 12 h. The reaction mixture is then diluted with water (150 mL) and extracted twice with dichloromethane. The organic layers are combined, dried over MgSO₄, filtered, and concentrated under reduced pressure to provide a solid residue. The residue is recrystallized from ethyl acetate-petroleum ether to give 5.5 g (30%) of product. Selected ¹H resonances: (270 MHz, CDCl₃) 4.00 ppm, 1H, C12, bs; 3.6 ppm, 1H, C3, m; 1.03 ppm, 3H, C17, d; 0.9 ppm and 0.68, 3H each, angular methyls of steroid, s.

Example 15

Synthesis of the Deoxycholatespermine Conjugate

Spermine (0.3 g, 1.18 mmol) is added to a stirred solution of the activated ester of deoxycholate (0.15 g, 0.28 mmol) and triethylamine (0.1 mL, 0.71 mmol) in dichloro-methane. The mixture is stirred for 0.5 h and a precipitate is observed. The solids are filtered through a buchner funnel. The filtrate is washed with water (10 mL). The organic layer is concentrated to give a residue (0.18 g). The residue is acidified with methanolic trifluoroacetic acid. The resulting solution is purified by reverse phase chromatography to give 0.14 g (80%) of the steroid-polyamine conjugate. Selected ¹H resonances: (270 MHz, CD₃OD) 3.98 ppm, 1H, C12, bs; 3.55 ppm, 1H, C3, m; 3.4 ppm, 2H, spermine methylenes next to amide linkage, bt; 3.0 ppm, 10H spermine methylenes except those next to amide, bs; 1.03 ppm, 3H, C17, d; 0.9 ppm and 0.68, 3H each, angular methyls of steroid, s. High resolution mass spectrometry has confirmed the proper molecular weight.

In the same fashion, other non-glycosylated amphiphatic steroidal compounds, including but not limited to cholic acid or chenodeoxycholic acid, may be conjugated to a polyamine molecule, including but not limited to ethylene diamine, diethylene triamine, spermine, spermidine, other polyalkylene-polyamines, and the like.

Example 16

Coupling of Leu-enkephalin to the deoxycholate-spermine conjugate

To a solution of steroid-spermine conjugate (13 mg, 0.02 Mole) is added Na₂CO₃ (11 mg, 0.10 mmol). The mixture is stirred for 1 h. The solids are then filtered through a buchner funnel and concentrated under reduced pressure. This residue is dissolved in 10 mL of DMF. Diisopropylethyl amine (12 μL, 0.067 mmol, DIEA), 1-hydroxybenzotriazole hydrate (9 mg, 0.067 mmol), O-benzotriazol-1-yl-tetramethyluronium hexafluorophosphate (27 mg, 0.067 mmol, HBTU) and Leu-enkephalin (10 mg, 0.015 mmol) are added to the solution. The resulting mixture is stirred for three days.

The solvent is then removed under reduced pressure to give a residue. The residue is taken up in dichloromethane and triturated until a solid precipitated. The precipitate is purified by reverse phase chromatography to give 10 mg of a steroid peptide conjugate. Selected ¹H NMR resonances: (270 MHz, CD₃OD) 7.2 ppm, 5H, Phe aromatics, m; 6.95 ppm, 2H, Tyr aromatics 2 and 6, d; 6.65 ppm, 2H, Tyr aromatics 3 and 5, d; 0.9 ppm, 3H, C17 methyl of steroid, d. High resolution mass spectrometry has confirmed the proper molecular weight.

Example 17

3α-Hydroxy-7,12-di-(1'-α-glucosyl)-5β-cholic acid
(Entry No. 3$^d$, Table I, above)

To a stirred solution of the methylcholate product of Example 13, 1bove, (15 mmol) in THF (150 mL) is added NaOH (10 g, 250 mmol) in 95% ethanol (200 mL). The reaction mixture is refluxed for 48 h. The reaction mixture is then concentrated, and the residue is dissolved in ethyl acetate (300 mL), washed with water (2×250 mL), saturated aqueous sodium bicarbonate (2×300 mL), brine (300 mL) and dried (Na$_2$SO$_4$). Solvent is evaporated to provide the glycosteroid acid product in 80% yield. Activation of the carboxylic acid group is carried out as follows.

Example 18

Synthesis of the glycosteroidspermine conjugate via the activated acid

Triethylamine (120 µL, 0.8 mmol) is added to a stirred solution of the glycosteroid acid (0.3 g, 0.2 mmol; See, above), N-hydroxysuccinimide (72 mg, 0.6 mmol), 1-hydroxybenzotriazole hydrate (112 mg, 0.8 mmol) and 1-(3-dimethylaminopropyl)-3-ethylcarbodiimide (160 mg, 0.8 mmol) in dichloromethane. The mixture is stirred for 12 h. After this time, the reaction mixture is diluted with water (50 mL) and extracted twice with dichloromethane. The organic layers are combined, dried over MgSO$_4$, filtered, and concentrated under reduced pressure to provide a solid residue 0.33 g (96%) of the activated ester.

To a stirred solution of the activated ester (0.15 g, 0.089 mmol) and triethylamine (50 mL, 0.35 mmol) in dichloromethane is added spermine (0.3 g, 0.61 mmol). The mixture is stirred for 0.5 h and a precipitate is observed. The solids are filtered over a buchner funnel. The filtrate is washed with water (10 mL). The organic layer is concentrated to give a residue (0.18 g). The residue is acidified with methanolic trifluoroacetic acid. The resulting solution is purified by reverse phase chromatography to give 0.14 g (85%) of the glycosteroid-polyamine conjugate.

In the same fashion, other glycosylated amphiphatic steroidal compounds, including but not limited to the mono-, di-, or triglycosylated forms (as appropriate) of cholic acid, 7-deoxycholic acid, or chenodeoxycholic acid, may be conjugated to a polyamine molecule, including but not limited to ethylene diamine, diethylene triamine, spermine, spermidine, other polyalkylenepolyamines, and the like.

Example 19

Deprotection of the protected glycosteroid-polyamineconjugate

A hydrogenation flask is charged with a solution of the protected glycosteroid-spermine conjugate (0.11 g, 0.06 mmol; See, above) in a mixture of methanol (20 mL) and benzene (4 mL), followed by Pd(OH)$_2$ catalyst and formic acid (1 mL). The reaction mixture is shaken under a hydrogen atmosphere at 50 psi for 40 h. The catalyst is filtered off with Celite®, and the solvent is removed by evaporation under reduced pressure. The product is purified over Sephadex-LH-20 gel, eluting with MeOH, to give the desired glycosteroid-spermine conjugate.

Example 20

Leu-enkephalin conjugate of the deprotected glycosteroid with the spermine polyamine "linker"

Triethylamine (0.8 mmol) is added to a stirred solution of tert-butylcarbonyl (Boc)-protected Leu-enkephalin (0.2 mmol), N-hydroxysuccinimide (0.6 mmol), 1-hydroxybenzotriazole hydrate (0.8 mmol) and 1-(3-dimethylaminopropyl)-3-ethylcarbodiimide (0.8 mmol) in dichloromethane. The mixture is stirred for 12 h. After this time, the reaction mixture is diluted with water (50 mL) and extracted twice with dichloromethane. The organic layers are combined, dried over MgSO$_4$, filtered, and concentrated under reduced pressure to provide the activated Boc-Leu-enkephalin in good yield.

To a stirred solution of the activated Boc-Leu-enkephalin (0.089 mmol) and triethylamine (0.35 mmol) in dichloromethane is added the deprotected glycosteroidspermine conjugate described above (0.61 mmol). The mixture is stirred for 0.5 h and a precipitate is observed. The solids are filtered over a buchner funnel. The filterate is washed with water (10 mL). The organic layer is concentrated to give a residue, which is acidified with methanolic trifluoroacetic acid. The resulting solution is purified by reverse phase chromatography to give the desired Boc-Leu-enkephalin conjugate in good yield.

Example 21

Figure 7:
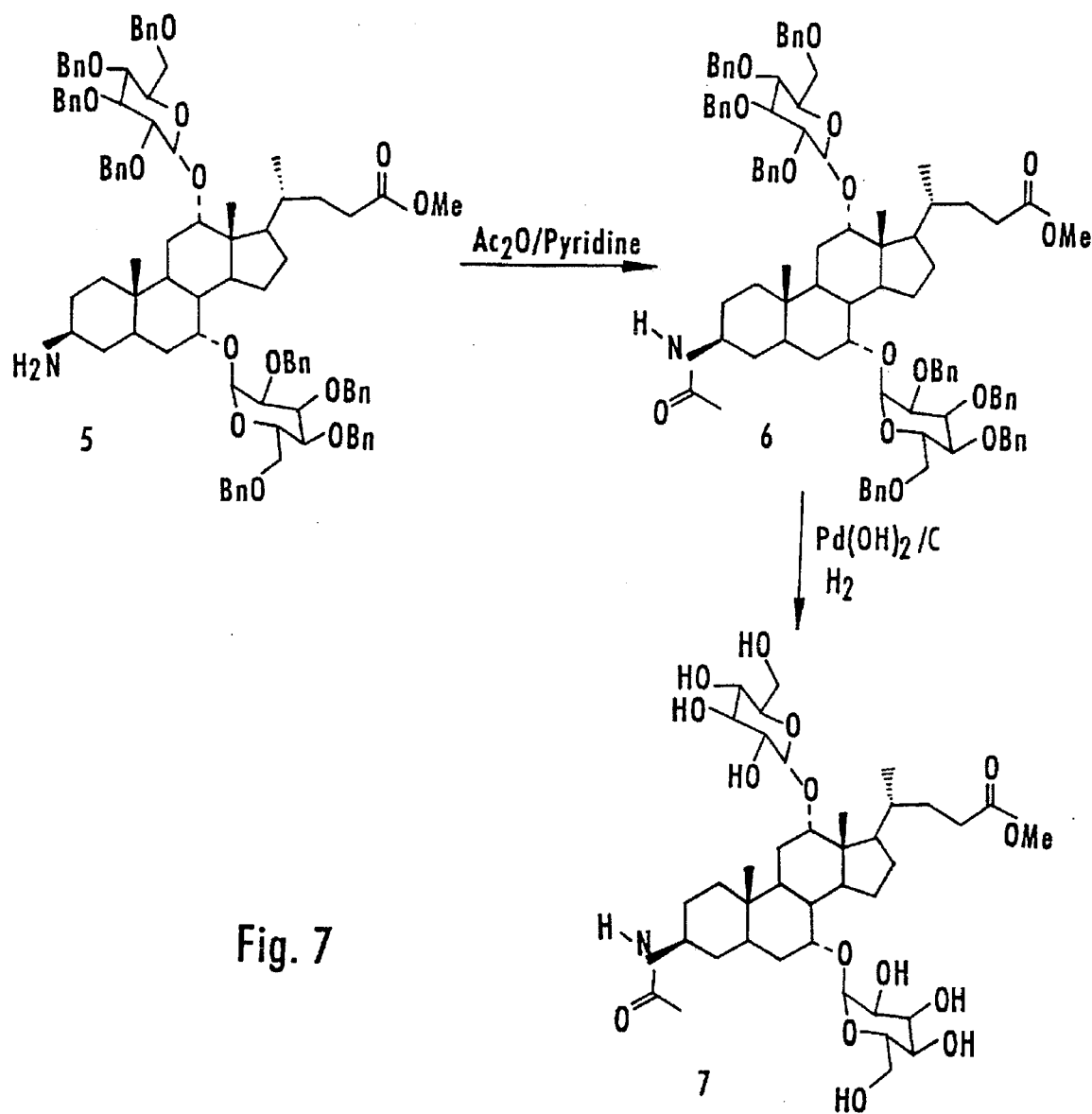
FIG. 7. Synthetic scheme for the preparation of methyl 3β-acetylamino-7α,12α-di-O-glucosyl-5β-cholate.

Synthesis of Methyl 3β-acetylamino-7α,12α-di-O-glucosyl-5β-cholate (See, FIG. 7)

21.1. Methyl 3β-acetylamino-7α,12α-di(2',3',4',6'-tetra-O-benzyl-1'α-glycosyl)-5β-cholate (6)

The amino compound 5 (340 mg, 0.23 mmol) is dissolved in pyridine (2 mL) and cooled to 0° C. in an ice-bath. To this solution is added acetic anhydride (0.5 mL). The reaction is then allowed to warm up gradually to room temperature overnight. TLC shows completion of the reaction. The reaction is then worked up by pouring the reaction mixture into ice-cold water (10 mL) and allowing the resulting mixture to stir for 15 minutes at room temperature. The reaction product is extracted with ethyl acetate. The organic extract is then washed with water, dried over MgSO$_4$, and filtered. The solvent is subsequently allowed to evaporate to dryness. The product (350 mg) is thus obtained (100% yield). TLC analysis reveals a single spot. IR (neat) 3310, 2927, 1730, 1461, 1082, 738 cm$^{-1}$. $^1$H NMR (CDCl$_3$) δ0.727 (s, 3H), 0.975 (d, 3H), 0.992 (s, 3H), 1.962 (s, 3H), 1.054–2.379 (m, 27n), 3.633 (s, 3H), 3.412–5.028 (m, 30H), 5.575 (d, 1H), 6.939–7.266 (m, 40H).

21.2. Methyl 3β-acetylamino-7α,12α-di-O-glucosyl-5β-cholate (7)

The tetra-benzylated compound 6 (350 mg, 0.23 mmol) is dissolved in 3 mL of toluene. Ethanol (15 mL) is then added, followed by Pd(OH)$_2$/C (350 mg) and formic acid (0.2 mL). The reaction mixture is then shaken on a Parr® Shaker for 48 hours. TLC analysis shows completion of reaction. The reaction mixture is then filtered through Celite®. The filtrate is concentrated to dryness under vacuum. Addition of ethyl acetate causes the product to crystallize. It is then filtered and dried. Yield: 170 mg (0.21 mmol, 91%). MS 810 (M+Na). IR (KBr) 3350, 2931, 1703, 1632, 1150, 1024 cm$^{-1}$. $^1$H NMR (D$_2$O) δ0.631 (s, 3H), 0.775 (d, 3H), 0.846 (s, 3H), 1.832 (s, 3H), 1.052–2.306 (m, 27H), 3.533 (s, 3H), 3.201–4.003 (m, 12H), 4.827 (d, 1H), 5.072 (d, 1H).

Example 22

Figure 8:
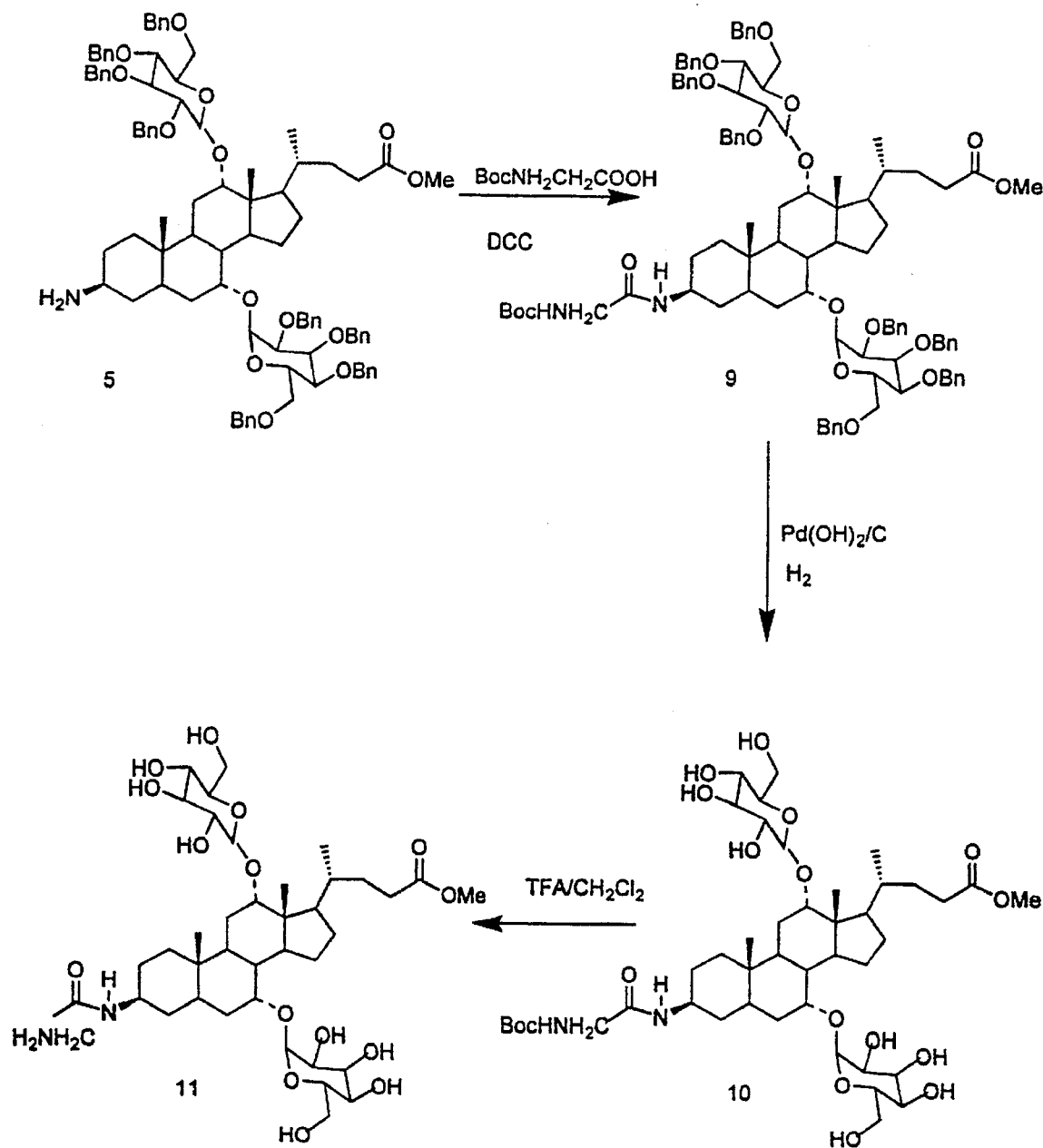
FIG. 8. Synthetic scheme for the preparation of methyl 3β-glycylamino-7α,12α-di-O-glucosyl-5β-cholate.

Synthesis of Methyl 3β-glycylamino-7α,12α-di-O-glucosyl-5β-cholate (See, FIG. 8)

22.1. Methyl 3β-(N-Boc-glycylamino)-7β,12β-di(2', 3',4',6'-tetra-O-benzyl-1'α-glycosyl)-5β-cholate (9)

The amino compound 5 (200 mg, 0.14 mmol) is dissolved in 5 mL of CH$_2$Cl$_2$ (distilled from CaH$_2$). Boc-glycine (37 mg, 0.21 mmol) and DCC (58 mg, 0.28 mmol) are then added. The reaction mixture is then allowed to stir overnight at room temperature. The precipitated DCU is filtered off and the filtrate is passed through a silica gel flash chromatography column packed in hexane. The product is eluted with increasing percentage of ethyl acetate in hexane (up to 40% of ethyl acetate in hexane). The fractions containing the product are pooled and the solvent allowed to evaporate to dryness. Product (154 mg) is obtained (0.095 mmol, 68% yield). MS 1646 (M+Na). IR (neat) 2926, 2866, 1734, 1678, 1497, 1452, 1364, 1163, 1071 $cm^{-1}$. $^1$H NMR (CDCl$_3$) $\delta$0.723 (s, 3H), 0.981 (m, 6H), 1.444 (s, 9H), 1.002–2.750 (m, 27H), 3.462–5.019 (m, 32H), 5.150 (br s, 1H), 6.251 (br s, 1H), 6.945–7.266 (m, 40H).

22.2. Methyl 3β-(N'-Boc-glycylamino)-7α,12α-di-O-glucosyl-5β-cholate (10)

The tetra-benzylated compound 9 (490 mg, 0.30 mmol) is dissolved in toluene (3 mL). Ethanol (17 mL) is added, followed by 20% Pd(OH)$_2$/C (490 mg) and formic acid (0.2 mL). The mixture is hydrogenated at 40 psi on a Parr® Shaker apparatus for 48 hours. TLC analysis shows completion of reaction. The catalyst is filtered off through a pad of Celite®, which is then washed several times with small amounts of ethanol. The filtrate is allowed to evaporate to dryness. The addition of ethyl acetate causes the formation of a precipitate, which is filtered and dried to provide 270 mg of product (quantitative yield). MS 926 (M+Na). IR (neat) 3355, 2928, 1625, 1588, 1023 $cm^{-1}$. $^1$H NMR (CD$_3$OD) $\delta$0.691 (s, 3H), 0.899 (d, 3H), 0.920 (s, 3H), 1.363 (s, 9H), 1.032–2.503 (m, 27H), 3.141–4.087 (m, 14H), 4.806 (d, 1H), 5.007 (d, 1H).

22.3. Methyl 3β-glycylamino-7α,12α-di-O-glucosyl-5β-cholate (11)

The Boc-amino compound 10 (150 mg, 0.17 mmol) is dissolved in 8 mL of CH$_2$Cl$_2$. To this solution is added 2 mL of trifluoroacetic acid with stirring for 0.5 hours at room temperature. The solvent and TFA is allowed to evaporate to dryness. The compound is taken up into water and filtered. The filtrate is lyophilized to a white powder. The compound is then isolated as the TFA salt: 95 mg (0.10 mmol, 59% yield). IR (KBr) 3399, 1679, 1556, 1440, 1269, 1200, 1141, 1024 $cm^{-1}$. MS 825 (M+Na). $^1$H NMR (D$_2$O) $\delta$0.592 (s, 3H), 0.738 (d, 3H), 0.807 (s, 3H), 1.025–2.666 (m, 27H), 3.497 (s, 3H), 3.176–3.900 (m, 14H), 4.787 (d, 1H), 5.028 (d, 1H).

Example 23

Figure 9:
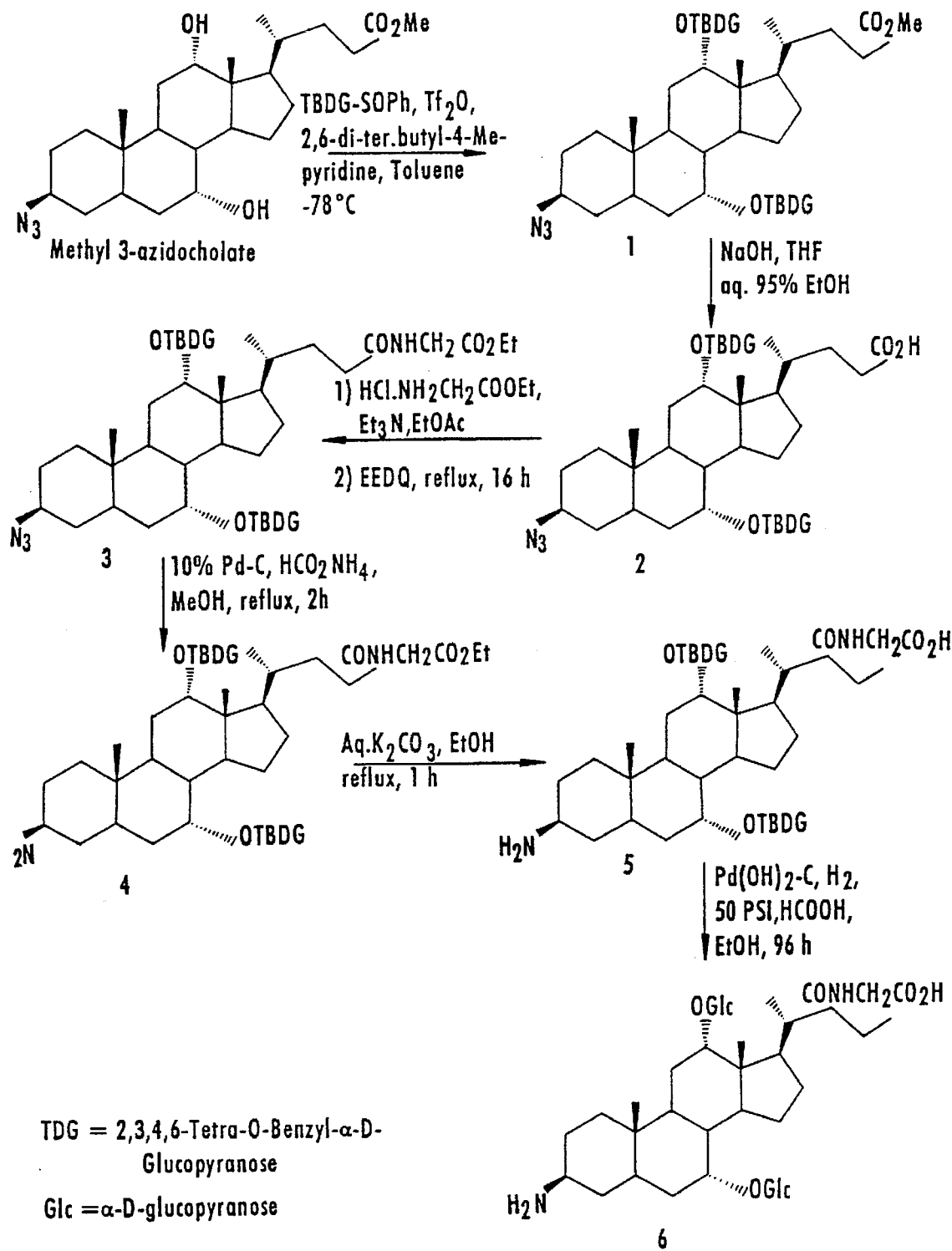
FIG. 9. Synthetic scheme for the preparation of 3β-amino-7α,12α-di(1'α-glucosyl)-5β-cholan-24-oic acid N-[carboxymethyl]amide.

Synthesis of 3β-Amino-7α,12α-di(1'α-glucosyl)-5β-cholan-24-oic acid N-[carboxymethyl]amide (6)
(See, FIG. 9)

Reactions are generally run under a positive pressure of dry nitrogen. Anhydrous solvents are used unless water is involved in the reaction. Flash chromatography employs Merck silica gel (Kieselgel 60, 200–400 mesh). TLC is performed with 0.2 mm coated commercial silica gel plates (E. Merck, Kieselgel 60 F$_{254}$). Melting points are determined using a Mel-Temp 11 (Laboratory Devices) capillary-melting-point apparatus in open capillary tubes and are uncorrected. Microanalysis are performed by Atlantic Microlab, Inc., Norcross, Ga. Infrared Spectra are recorded on Midac Prospect-IR (FT-IR) and reported in wavenumbers ($cm^{-1}$). Proton NMR spectra are measured at 300 MHz on a Varian instrument. Chemical shifts are reported in ppm downfield from TMS.

23.1. Methyl 3β-azido-5β-cholate

A mixture of methyl 3-O-mesylcholate (40 g, 80 mmol) and sodium azide (26 g, 400 mmol) in 2-methylpyrrolidone (200mL) is heated at 105° C. for 3 h. Afterward the reaction mixture is poured into ice-cold water and stirred for 15 min. After filtration, the solids are washed with water (1 L) and air dried. Recrystallization of the precipitate from methanol (125 mL) gives 32.18 g (90%) of methyl 3-azidocholate as white needles (mp 148°–149° C.). TLC (solvent—EtOAC: Hexane=3:2) R$_f$=0.5. IR (KBr): 3448, 2938, 2868, 2097, 1730 $cm^{-1}$. $^1$H NMR (CDCl$_3$): $\delta$4.05 (s, 1H), 3.95 (d, 1H), 3.67 (s, 3H), 2.62–0.70 (M, 36H). Fab MS: 470 (M+Na)$^+$.

23.2. Methyl 3β-azido-7α,12α-di-(2', 3', 4', 6'-tetra-O-benzyl-1'α-glucosyl)-5β-cholate (1)

Triflic anhydride (9.24 mL, 55 mmol) is added to cooled (−78° C.) toluene (100 mL) solvent with stirring for 5 min. To this solution, dried (by azeotropic distillation from toluene) phenyl 2,3,4,6-tetra-O-benzyl-D-glucopyranosyl-1-sulfoxide (32.43 g, 50 mmol), dissolved in toluene (100 mL), is added dropwise. After 15 min of stirring, a solution of dried (by azeotropic distillation from toluene) 2,6-di-ter-butyl-4-methyl-pyridine (8.21 g, 40 mmol) in toluene (20 mL) is added to the reaction mixture and stirred for 10 min at −78° C. To this reaction mixture, dried (by azeotropic distillation from toluene) methyl 3-azidocholate (8.94 g, 20 mmol) in CH$_2$Cl$_2$ and toluene (1:4, 50 mL) is added dropwise. The reaction progress is monitored by TLC. The temperature of the reaction mixture is slowly allowed to rise to −60° C. over 45 min. During this time, the TLC spot due to methyl 3-azidocholate completely disappears. The reaction mixture is then poured into saturated aqueous sodium bicarbonate (250 mL) and stirred for 10 min. The organic layer is separated, and the aqueous layer is extracted with dichloromethane (2×50 mL). The organic layers are combined and washed with water (3×250 mL), dried (Na$_2$SO$_4$), and concentrated. The residue is purified by flash chromatography (EtOAC:Hexane=1:9 to 1:4) to furnish 1 (12 g, 40%), which is immediately recrystallized (EtoAC:Hexane= 1:5) to give 9 g (30%) of product as needles (mp 112°–114° C.). TLC (solvent—EtOAC:Hexane=1:4) R$_f$=0.6. IR (KBr): 3085, 3061, 3029, 2921, 2867, 2097, 1735, 1603, 1495, 1452, 1360, 1256, 1207, 1160, 1091, 1071, 1031 $cm^{-1}$. $^1$H NMR (CDCl$_3$): $\delta$7.37–6.84 (m, 40H), 5.15 (d, 1H, J=4Hz), 4.95 (d, 1H, J=4Hz), 4.86–4.26 (m, 15H), 4.08–3.40 (m, 16H), 2.60–0.71 (m, 36H). Fab MS: 1515 (M+Na)$^+$. Anal. Calc. for C$_{93}$H$_{110}$O$_{14}$N$_3$: C, 74.76; H, 7.43; N, 2.81. Found: C, 74.84; H, 7.40; N, 2.79.

23.3. 3β-Azido-7α,12α-Di-(2', 3', 4', 6'-tetra-O-benzyl-1'α-glucosyl)-5β-cholan-24-oic acid (2)

To a stirred solution of 1 (4.1 g, 2.75 mmol) in THF (50 mL), is added NaOH (1.1 g, 27.5 mmol) in 95% aqueous ethanol (50 mL). The mixture is heated under reflux for 1.5 h. The mixture is then allowed to cool and is concentrated to provide a residue, which is dissolved in ethyl acetate (100 mL), washed consecutively with water (2×50 mL), saturated aqueous sodium bicarbonate (2×50 mL), and brine (100 mL). After drying (Na$_2$SO$_4$), the solvent is evaporated to afford pure 2 (3.86 g, 95%) as a white foam (top 60°–62° C.). TLC (solvent—EtOAC:Hexane=3:7) R$_f$=0.2. IR (KBr): 3420, 3080, 3057, 3030, 2922, 2868, 2097, 1735, 1725, 1707, 1496, 1451, 1362, 1273, 1147, 1070 $cm^{-1}$. $^1$H NMR (CDCl$_3$): $\delta$7.20–6.85 (m, 40H), 5.03 (d, 1H, J=3Hz), 5.02 (d, 1H, J=3Hz), 4.85–3.20 (m, 28H), 2.62–0.77 (m, 36H). Fab MS: 1502 (M+Na)$^+$. Anal. Calc. for C$_{92}$H$_{108}$O$_{14}$N$_3$: C, 74.66; H, 7.36; N, 2.84. Found: C, 74.68; H, 7.18; N, 2.79.

23.4. 3β-Azido-7α,12α-di-(2', 3', 4', 6'-tetra-O-benzyl-1'α-glucosyl)-5β-cholan-24-oic acid N-[ethyl methylcarboxylate]amide (3)

To a suspension of ethylglycine hydrochloride (420 mg, 3 mmol) in ethyl acetate (100 mL) is added triethylamine (3 mL) with stirring at 40° C. for 1 h. The compound 2 (2.986 g, 2 mmol) and ethyl 1,2-dihydro-2-ethoxy-1-quinolinecarboxylate (EEDQ) (988 mg, 4 mmol) in ethylacetate (100 mL) are then added to this mixture, which is then heated under reflux for 16 h. Afterward, the mixture is cooled, washed successively with 0.5N aqueous NaOH (100 mL), 0.5N aqueous HCl (100 mL), and water (2×200 mL). After drying ($Na_2SO_4$), the solvent is evaporated. The residue is purified by flash chromatography (EtOH:$CH_2Cl_2$= 1:19) to give 3 (2.66 g, 85%) as a white foam (top 46°–47° C.). TLC (solvent—EtOH:$CH_2Cl_2$=1:19) $R_f$=0.3. IR (KBr): 3410, 3351, 3088, 3060, 3032, 2924, 2098, 1746, 1674, 1503, 1454, 1366, 1262, 1050 $cm^{-1}$. $^1$H NMR ($CDCl_3$): δ7.25–6.85 (m, 40H), 5.82 (brs, 1H), 5.15 (m, 2H), 4.84–3.40 (m, 30H), 2.60–0.65 (m, 39H). Fab MS: 1586 $(M+Na)^+$. Anal. Calc. for $C_{96}H_{115}O_{15}N_4$: C, 73.67; H, 7.41; N, 3.88. Found: C, 73.45; H, 7.46; N, 3.60.

23.5. 3β-Amino-7α,12α-di-(2', 3', 4', 6'-tetra-O-benzyl-1'α-glucosyl)-5β-cholan-24-oic acid N-[ethyl methylcarboxylate]amide (4)

To a solution of compound 3 (2.35 g, 1.5 mmol) in ethylacetate (40 mL) and methanol (60 mL) is added ammonium formate (1.26 g, 20 mmol) and 10% palladium on carbon (anhydrous, 200 mg). The contents of the reaction vessel are heated under reflux for 6 h. After filtration through Celite® (15 g), the filtrate is concentrated, dissolved in methylene chloride (100 mL), and washed with water (200 mL). After drying ($Na_2SO_4$), the solution is concentrated. The residue is separated into its components by flash chromatography: starting material 3 (500 mg, using 5% ethanol in methylene chloride) and, with 10% ethanol in methylene chloride, product 4 (1.155 g, 50%) as a white foam (mp 64°–66° C.). TLC (solvent—EtOH:$CH_2Cl_2$=1:9) $R_f$=0.3. IR (KBr): 3426, 3358, 3090, 3065, 3045, 3012, 2925, 2869, 1741, 1670, 1613, 1520, 1454, 1363, 1321, 1211, 1157, 1085 $cm^{-1}$. $^1$H NMR ($CDCl_3$): δ7.27–6.90 (m, 40H), 5.81 (brs, 1H), 4.99 (brs, 2H), 4.85–3.40 (m, 25H), 3.24–3.18 (m, 1H), 3.10–3.02 (br s, 1H), 2.92–2.88 (m, 1H), 2.60–0.60 (m, 39H). Fab MS: 1559 $(M+Na)^+$. Anal. Calc. for $C_{96}H_{117}O_{15}N_2$: C, 74.91; H, 7.67; N, 1.82. Found: C, 74.74; H, 7.64; N, 1.86.

23.6. 3β-Amino-7α,12α-di-(2', 3', 4', 6'-tetra-O-benzyl-1'α-glucosyl)-5β-cholan-24-oic acid N-[carboxymethyl]amide (5)

To a refluxing solution of compound 4 (770 mg, 0.5 mmol) in ethanol (25 mL), 10% aqueous potassium carbonate (1 mL) is added. Heating under reflux is continued for an additional 1 h. The mixture is concentrated and diluted with methylene chloride (50 mL). The organic layer is washed with water (2×50 mL) and dried ($Na_2SO_4$). Evaporation of the solvent furnished 5 (683 mg, 90%) as a white powder (mp 150°–152° C.). TLC (solvent—EtOH:$CH_2Cl_2$=1:9) $R_f$=0.1. IR (KBr): 3414, 3086, 3061, 3030, 2923, 2868, 1659, 1640, 1628, 1601, 1497, 1452, 1387, 1159, 1088, 1070, 1028 $cm^{-1}$. $^1$H NMR ($CDCl_3$): δ7.35–6.85 (m, 40H), 6.20 (br s, 1H), 5.10–3.48 (m, 32H), 3.00–0.60 (m, 36H). Fab MS: 1531 $(M+Na)^+$. Anal. Calc. for $C_{94}H_{113}O_{15}N_2$: C, 74.71; H, 7.54; N, 1.85. Found: C, 74.58; H, 7.76; N, 1.90.

23.7. 3β-Amino-7α,12α-di-(-1'α-glucosyl)-5β-cholan-24-oic acid N-[carboxymethyl]amide (6)

To a solution of 5 (605 mg, 0.4 mmol) in ethanol (100 mL), formic acid (1.5 mL) and palladium hydroxide (20%) on carbon (600 mg) are added. The resulting mixture is hydrogenated at 50 psi for 24 h. TLC indicates incomplete hydrogenolysis. Additional formic acid (1.5 mL) is added and hydrogenation is allowed for another 24 h. Additional formic acid and further hydrogenation can be added and performed as warranted. The reaction mixture is then filtered through sand and a membrane filter and concentrated. The residue is precipitated with EtOAc and filtered. The precipitate is dissolved in 25 mL deionized water and freeze-dried. Reverse-phase column chromatography of the residue over CHP-20 (water followed by MeOH:Water=1:1) gives 189 mg (60%) of 6 as a white foam (mp>275° C., decomp.). TLC (solvent—MeOH:$CH_2Cl_2$:Isopropylamine=2:2:1) $R_f$=0.15. IR (KBr): 3394, 2932, 2878, 2870, 1640, 1630, 1619, 1598, 1389, 1150, 1023 $cm^{-1}$. $^1$HNMR ($D_2O$): δ5.35–5.33 (m, 1H), 5.08 (d, 1H, J=3Hz), 4.87 (d, 1H, J=3 Hz), 3.98 (br s, 1H), 3.80–3.24 (m, 14H), 2.60–0.65 (m, 37H). Fab MS: 781 $(M+Na)^+$. Anal. Calc. for $C_{38}H_{64}O_{15}N_2 \cdot 3H_2O$: C, 54.13; H, 8.37; N, 3.32. Found: C, 54.35; H, 8.43; N, 3.25.

Example 24

Figure 10:
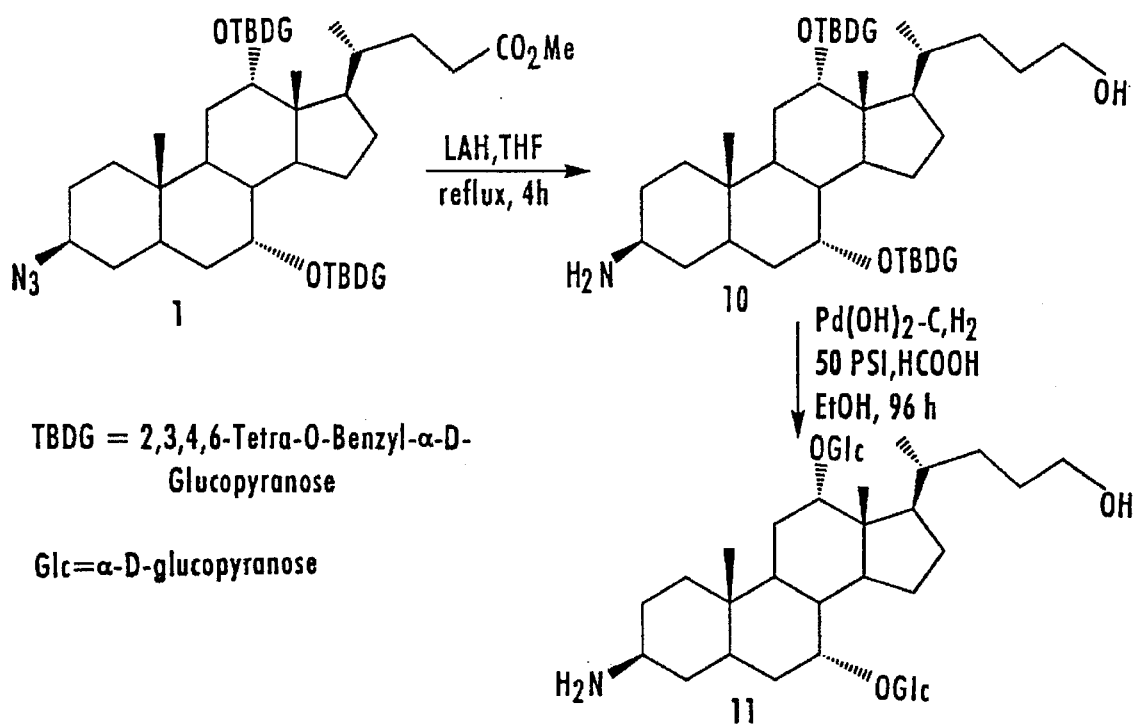
FIG. 10. Synthetic scheme for the preparation of 3β-amino-24-hydroxy-7α,12α-di(1'α-glucosyl)-5β-cholane.

Synthesis of 3β-Amino-24-hydroxy-7α,12α-di(1'α-glucosyl)-5β-cholane (11) (See, FIG. 10)

24.1. β-Amino-24-hydroxy-7α,12α-di(1'α-glucosyl)-5β-cholane (10)

To a mixture of lithium aluminum hydride (LAH, 0.19 g, 5 mmol) in anhydrous tetrahydrofuran (THF, 100 mL) is added dropwise at r.t. a solution of compound 1 (745 mg, 0.5 mmol) in THF (20 mL). The resulting reacting mixture is heated under reflux for 16 h, and then allowed to cool to r.t. Excess LAH is destroyed by the dropwise addition of aqueous sodium hydroxide (5 mL). The mixture is then acidified with 1N hydrochloric acid (7 mL) and extracted with methylene chloride (2×20 mL). The organic layer is washed with water (2×40 mL), dried ($Na_2SO_4$) and concentrated. The residue is purified by flash column chromatography (ethyl acetate:hexane=1:2) to provide 485 mg (70%) of 10 as a white foam (mp 54°–56° C.). TLC (solvent—EtOH:$CH_2Cl_2$=1:9) $R_f$=0.3. IR (KBr): 3087, 3063, 3030, 2921, 2865, 1454, 1160, 1070 $cm^{-1}$. $^1$H NMR ($CDCl_3$): δ7.38–6.85 (m, 40H), 5.06 (br d, 2H), 4.95–3.40 (m, 28H), 3.11 (br s, 1H), 2.62–0.72 (m, 39H). Fab MS: 1438 $(M+H)^+$. Anal. Calc. for $C_{92}H_{112}O_{13}N$: C, 76.73; H, 7.85; N, 0.97. Found: C, 76.28; H, 7.90; N, 0.97.

24.2 3β-Amino-24-hydroxy-7α, 12α-di(1'α-glucosyl)-5β-cholane (11)

Compound 10 (431 mg, 0.3 mmol) is hydrogenated by methods similar to those described above to give 129 mg (60%) of 11 as a white foam (mp 196°–198° C.). TLC (solvent—MeOH: $CH_2Cl_2$:Isopropylamine=2:2:1) $R_f$=0.15. IR (KBr): 3399, 2936, 2878, 2869, 1630, 1597, 1590, 1045, 1022 $cm^{-1}$. $^1$H NMR ($D_2O$): δ5.04 (d, 1H, J=3.6Hz), 4.82 (d, 1H, J=3Hz), 3.94 (br s, 1H), 3.74–3.22 (m, 12H), 2.47 (dd, 1H, J=12Hz and 4Hz), 2.20 (m, 2H), 1.95–0.90 (m, 36H). Fab MS: 719 $(M+H)^+$. Anal. Calc. for $C_{36}H_{63}O_{13}N \cdot 4H_2O$: C, 54.72; H, 9.06; N, 1.77. Found: C, 54.52; H, 8.75, N, 1.67.

Example 25

Figure 11:
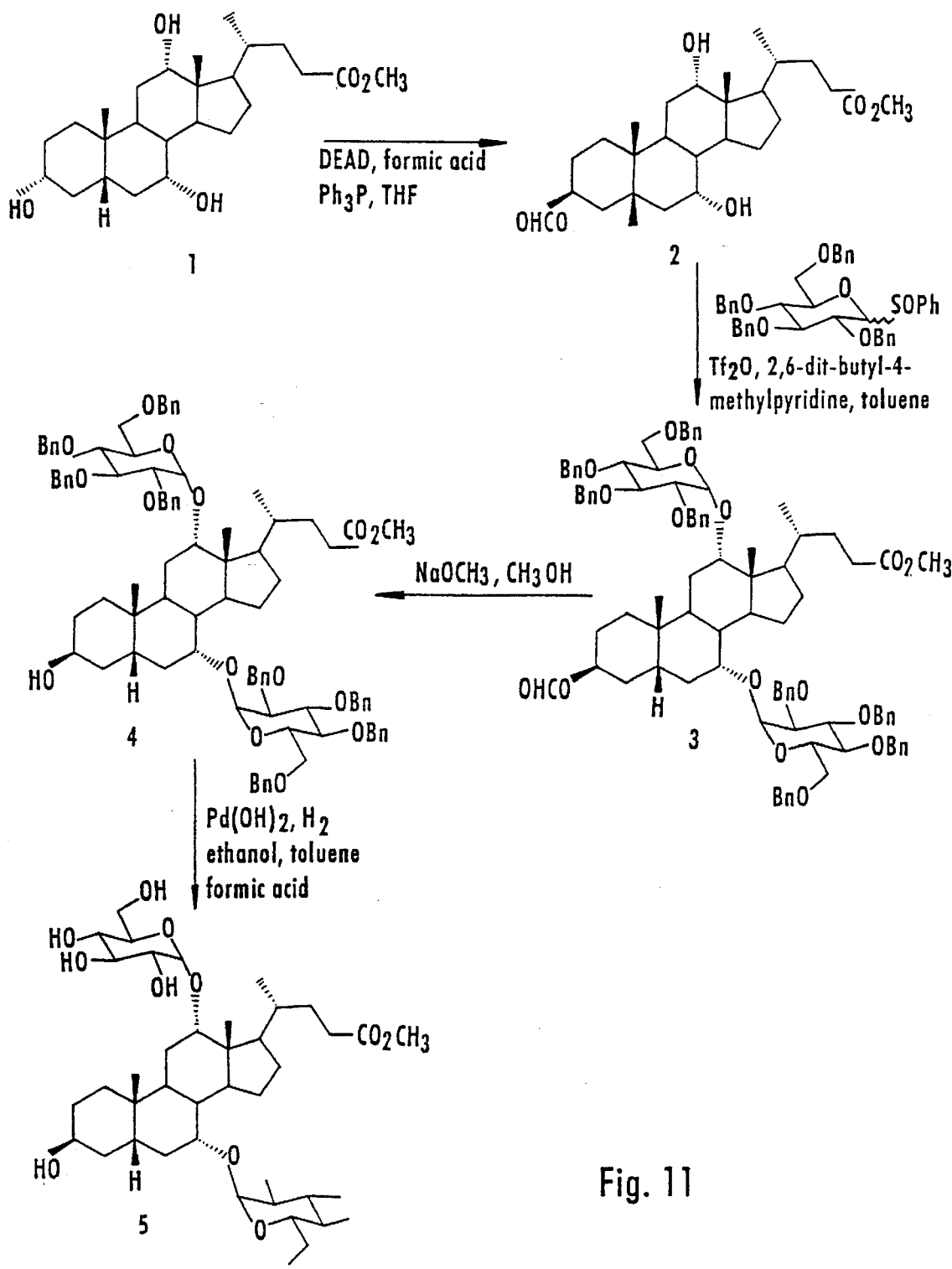
FIG. 11. Synthetic scheme for the preparation of methyl 3β-hydroxy-7α,12α-di(1'α-glucosyl)-5β-cholate.

Synthesis of Methyl 3β-hydroxy-7α,12α-di(1'α-glucosyl)-5β-cholate (5) (See, FIG. 11)

Kiesegel 60 F-254 TLC plate is used for all the TLC work unless otherwise indicated. FT-IR is performed on MIDAC Prospect IR instrument. NMR is performed on Varian VXR300s 300 MHz instrument. Chemical reagents are purchased from Aldrich or Fisher. Dry toluene is distilled from $CaH_2$. All other solvents are used directly from original container without further purification.

25.1. Methyl 3β-O-formylcholate (2)

To a solution of methyl cholate 1 (2.11 g, 5 mmol), formic acid (96%, 350 mg) and triphenyl phosphine (1.57 g, 6.0 mmol) in THF (75 mL) is added diethyl azodicarboxylate (DEAD, 1.05 g, 6.0 mmol) at room temperature (r.t.). The reaction mixture is stirred at r.t. for 16 h. Solvent is removed by evaporation. The residue is purified by use of a flash column (50%–60% ethyl acetate in hexane) to give 1.8 g (80%) of 2 as a thick oil: $R_f$ (60% ethyl acetate in hexane) 0.43; $^1H$ NMR δ ($CDCl_3$) 0.76 (s, 3H), 0.99 (s, 3H), 1.12 (d, 3H), 1.2–2.6 (m, 24H), 3.66 (s, 3H), 3.87 (s, 1H), 3.99 (s, 1H), 5.15 (s, 1H), 8.04 (s, 1H).

25.2. Methyl 3β-O-formyl-7α,12α-O-di(1'α-(2',3',4',6'-O-tetrabenzyl)glucosyl)-5β-cholate (3)

To a solution of phenyl 2,3,4,6,-O-tetrabenzyl-gluco-1-sulfoxide (6.33 g, 9.8 mmol) in 150 mL dry toluene is added triflic anhydride (1.66 mL, 9.8 mmol) at −78° C. After 15 min. stirring at −78° C., 2,6-di-t-butyl-4-methylpyridine (2 g, 9.8 mmol) in a small amount of toluene is added, followed by 2 (2 g, 4.4 mmol) in a small amount of methylene chloride. The dry ice/acetone bath is then replaced with a dry ice/chloroform bath to keep the reaction temperature at about −60° C. with stirring for 2.5 h. Saturated aq. $NaHCO_3$ (100 mL) is then added. The reaction mixture is extracted with ethyl acetate (3×30 mL). The organic layer is dried and purified by flash column chromatography (20% ethyl acetate in hexane) to give 3 g (44%) of 3 as a thick oil: $R_f$ (20% ethyl acetate in hexane) 0.32; IR (neat) 3031, 2922, 1728, 1710, 1454 $cm^{-1}$; $^1H$ NMR δ ($CDCl_3$) 0.72 (s, 3H), 0.96 (s, 3H), 0.97 (d, 3H), 1.2–2.5 (m, 24H) 3.4–5.2 (m, 30H), 3.62 (s), 7.0–7.4 (m, 40H), 8.02 (s, 1H).

25.3. Methyl 3β-hydroxyl-7α,12α-O-di(1'α-(2',3',4',6'-O-tetrabenzyl)glucosyl)-5β-cholate (4)

To a solution of 3 (3 g, 2 mmol) in anhydrous methanol (100 mL) at 0° C. is added sodium methylate (138 mg, 2.6 mmol). The mixture is stirred at r.t. for 2 h. Solvent is evaporated, and the residue is taken in methylene chloride, washed with a small amount of saturated aqueous ammonium chloride, and dried. Flash column chromatography (25% ethyl acetate in hexane) purification gives 750 mg (25%) of 4 as a thick oil: $R_f$ (30% ethyl acetate in hexane) 0.36; $^1H$ NMR δ ($CDCl_3$) 0.73 (s, 3H), 0.97 (s, 3H), 1.02 (d, 3H), 1.2–2.5 (m, 24H), 3.61 (s), 3.4–4.9 (m, 30H), 5.04 (t, 1H), 6.9–7.4 (m, 40H). MS m/e 1489 ($M^+$+Na).

25.4. Methyl 3β-hydroxyl-7α,12α-O-di(1'α-glucosyl)-5β-cholate (5)

To a solution of 4 (750 mg) in toluene (5 mL) and ethanol (15 mL) is added $Pd(OH)_2$ (20% in carbon, 750 mg) and formic acid (95%, 0.7 mL). The mixture is hydrogenated at 50 psi for 18 h, then filtered. The filtrate is then evaporated. The residue is redissolved in methanol, filtered and evaporated again. The residue is then dissolved in a small amount of water, purified by reverse-phase column chromatography (60 mL MCI CHP-20P gel column; 25% $H_2O$ in methanol). Lyophilization gives 260 mg (68%) of 5 as a white solid: $R_f$ (C-18 reverse phase, 30% $H_2O$ in methanol) 0.28; mp. 170° C. (recrystallized with methanol-ethyl acetate, phase transfer); IR (KBr) 3430, 2880, 1722, 1439 $cm^{-1}$; $^1H$ NMR ($D_2O$) δ 0.62 (s, 3H), 0.75 (d, J=6.3 Hz), 0.82 (s, 3H), 1.0–2.4 (m), 3.2–3.8 (m), 3.51 (s), 3.92 (s, 2H), 4.81 (d, J=3.6 Hz, 1H), 5.06 (d, J=3.9 Hz, 1H); MS m/e 769 ($M^+$+Na); Anal. Calc. (MW+$2H_2O$) C, 56.77; H, 7.99; Found C, 56.82; H, 8.22.

Example 26

Figure 12:
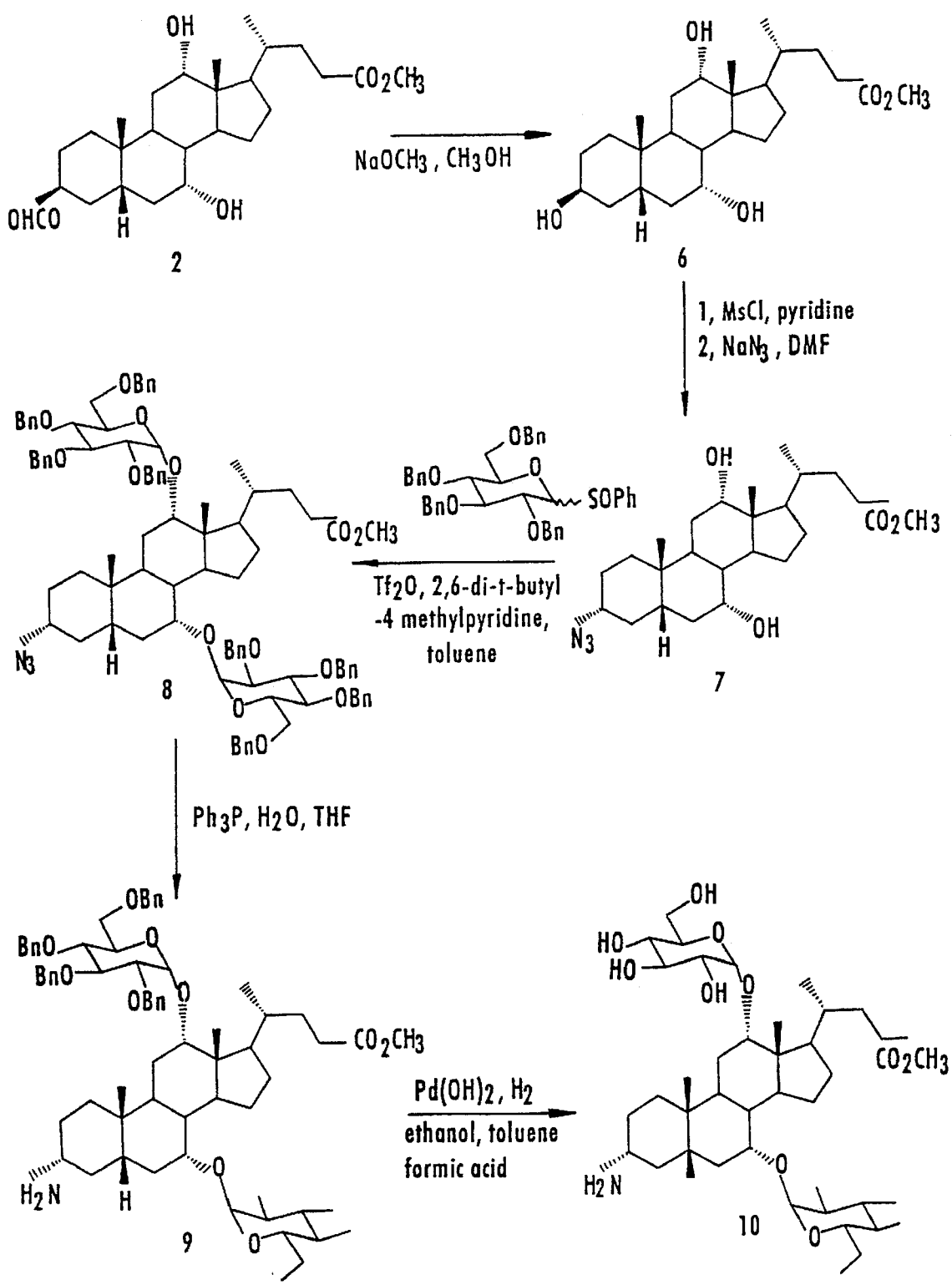
FIG. 12. Synthetic scheme for the preparation of methyl 3α-amino-7α,12α-di(1'α-glucosyl)-5β-cholate.

Synthesis of Methyl 3β-amino-7α,12α-di(1'α-glucosyl)-5β-cholate (10) (See, FIG. 12)

26.1. Methyl 3β-hydroxycholate (6)

Anhydrous methanol (10 mL) is added to a mixture of 2 (225 mg, 0.5 mmol) and sodium methylate (35 mg) at 0° C. The solution is stirred at r.t. for 0.3 h. Solvent is evaporated. The residue is taken up in methylene chloride, washed with conc. ammonium chloride, and dried. Removal of solvent gives 170 mg (84%) of 6 as a white solid: $R_f$ (90% ethyl acetate in hexane) 0.11; $^1H$ NMR ($CDCl_3$) δ0.68 (s, 3H), 0.93 (s, 3H), 0.97 (d, J=6 Hz, 3H); 1.1–2.5 (m, 25H), 3.65 (s, 3H), 3.85 (s, 1H), 3.97 (m, 1H), 4.04 (s, 1H), 6.72 (br.s.).

26.2. Methyl 3α-azidocholate (7)

To a solution of 6 (2.73 g, 6.4 mmol) in dry pyridine at 0° C. is added methanesulfonyl chloride (0.6 mL, 7.7 mmol). The resulting mixture is stirred at 0° C. for 2 h and r.t. for 2 h. Solvent is evaporated; the residue is taken in methylene chloride, washed with conc. ammonium chloride, and dried. The crude mesylate is dissolved in DMF (40 mL) and treated with $NaN_3$ (2 g). The mixture is stirred while heated to 110° C. for 4 h. Solvent is removed. The residue is taken up in methylene chloride, washed with conc. ammonium chloride, and dried. Flash column chromatography (20% ethyl acetate in hexane) gives 1.15 g (40%) of 7 as a white solid: $R_f$ (30% ethyl acetate in hexane) 0.45; IR (KBr) 3477, 2939, 2092, 1732 $cm^{-1}$; $^1H$ NMR ($CDCl_3$) δ0.68 (s, 3H), 0.90 (s, 3H), 0.96 (d, J=6.3 Hz, 3H), 1.1–2.5 (m, 24H), 3.14 (m, 1H), 3.66 (s, 3H), 3.85 (d, J=2.7 Hz, 1H), 3.98 (s, 1H).

26.3. Methyl 3β-azido-7α,12α-O-di(1'α-(2',3',4',6'-O-tetrabenzyl)glucosyl)-5β-cholate (S)

To a solution of phenyl 2,3,4,6-O-tetrabenzyl-gluco-1-sulfoxide (3.7 g, 5.7 mmol) in 120 mL dry toluene is added triflic anhydride (1.05 mL, 9.8 mmol) at −78° C. After 30 min. stirring at −78° C., 2,6-di-t-butyl-4-methylpyridine (1.17 g, 5.7 mmol) in a small amount of toluene is added, followed by 7 (1.15 g, 2.6 mmol) in 10 mL methylene chloride. The reaction mixture is stirred at −78° C. for 0.5 h. The dry ice/acetone bath is replaced with a dry ice/chloroform bath to keep the reaction temperature at about −60° C. for 2.5 h with stirring. 10% aq. $NaHCO_3$ is then added. The reaction mixture is extracted with ethyl acetate (3×50 mL). The organic layer is dried and purified by flash column chromatography (20% ethyl acetate in hexane) to give 1.10 g (28%) of 8 as a thick oil: $R_f$ (25% ethyl acetate in hexane) 0.50; IR (neat) 3030, 2927, 2091, 1736, 1455 $cm^{-1}$; $^1H$ NMR ($CDCl_3$) δ0.72 (s, 3H), 0.94 (s, 3H), 1.0 (d, 3H), 1.1–2.5 (m, 24H), 3.64 (s), 3.1–5.1 (m, 30H), 6.9–7.4 (m, 40H). MS m/e 1515 ($M^+$+Na+H).

26.4. Methyl 3α-amino-7α,12α-O-di(1'α-(2',3',4',6'-O-tetrabenzyl)glucosyl)-5β-cholate (9)

The compound 8 (1.1 g, 0.73 mmol) and triphenyl phosphine (0.62 g, 2.3 mmol) are dissolved in THF (30 mL) and H$_2$O (3 mL). The mixture is heated under reflux for 24 h. Solvent is evaporated. The residue is extracted with methylene chloride (3×20 mL) and dried. Flash column chromatography (2–3% methanol in chloroform) gives 640 mg (60%) of 9 as a thick oil: R$_f$ (10% methanol in chloroform) 0.45 (ninhydrin positive); $^1$H NMR (CDCl$_3$) δ0.71 (s, 3H), 0.92 (S, 3H), 0.98 (d, 3H), 1.1–2.5 (m, 24H), 3.63 (s), 3.3–5.1 (m, 32H), 6.9–7.4 (m, 40H).

26.5. Methyl 3α-amino-7α,12α-O-di(1'α-glucosyl)-5β-cholate (10)

To a solution of 9 (640 mg) in 3 mL toluene and 30 mL ethanol is added Pd(OH)$_2$ (20% on carbon, 640 mg) and formic acid (96%, 0.64 mL). The mixture is hydrogenated at 50 psi for 24 h. Then, 0.64 mL additional 96% formic acid is added and the hydrogenation is continued for another 24 h. The mixture is filtered and evaporated. The residue is redissolved in H$_2$O and the pH of the aqueous solution is titrated to 9 with 10% Na$_2$CO$_3$. The solution is purified by reverse-phase column chromatography (60 mL MCI CHP-20P gel column; 25% H$_2$O in methanol) to give 250 mg (77%) of 10 as white solid: R$_f$ (60% methanol, 20% methylene chloride, 20% Isopropylamine) 0.25; mp. 190° C. (recrystallized with methanol-ethyl acetate, phase transfer); IR (KBr) 3396, 2938, 1736 cm$^{-1}$; $^1$H NMR (D$_2$O) δ0.63 (s, 3H), 0.78 (d, J=6 Hz, 3H), 0.85 (s, 3H), 1.0–2.4 (m, 24H), 2.92 (br. s, 1H), 3.2–3.8 (m), 3.54 (s), 3.94 (s, 2H), 4.84 (d, J=4.2 Hz, 1H), 5.05 (d, J=4.2 Hz, 1H); MS m/e 769 (M$^+$+Na+H); Anal. Calc. (MW+6H$_2$O) C, 52.05; H, 7.44; N, 1.64; Found C, 52.12; H, 7.82; N, 1.64.

Example 27

Figure 13:
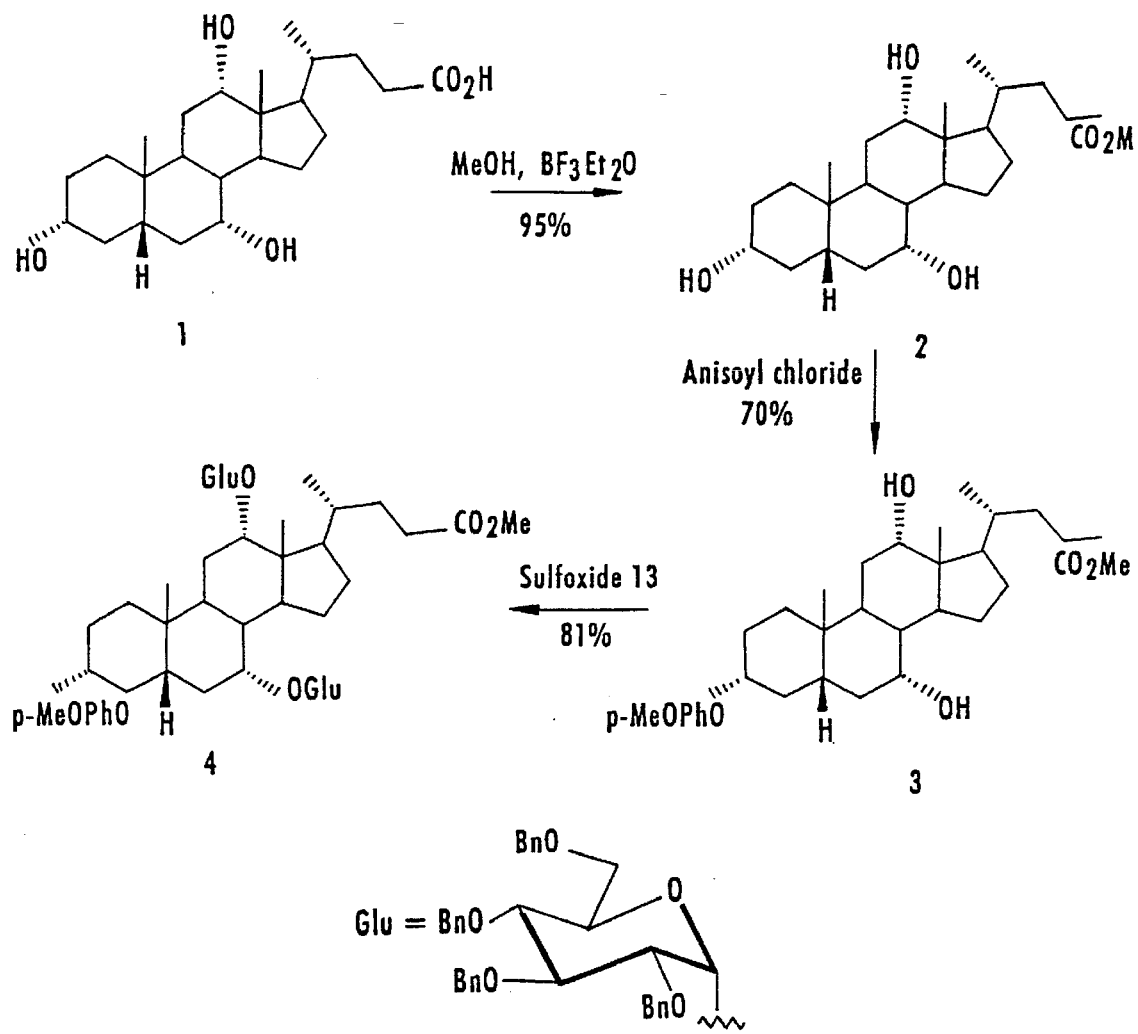
FIG. 13. Synthetic scheme for the preparation of intermediates for the synthesis of 7α,12α-di(1'α-glucosyl)cholic acid and its methyl ester.
Figure 14:
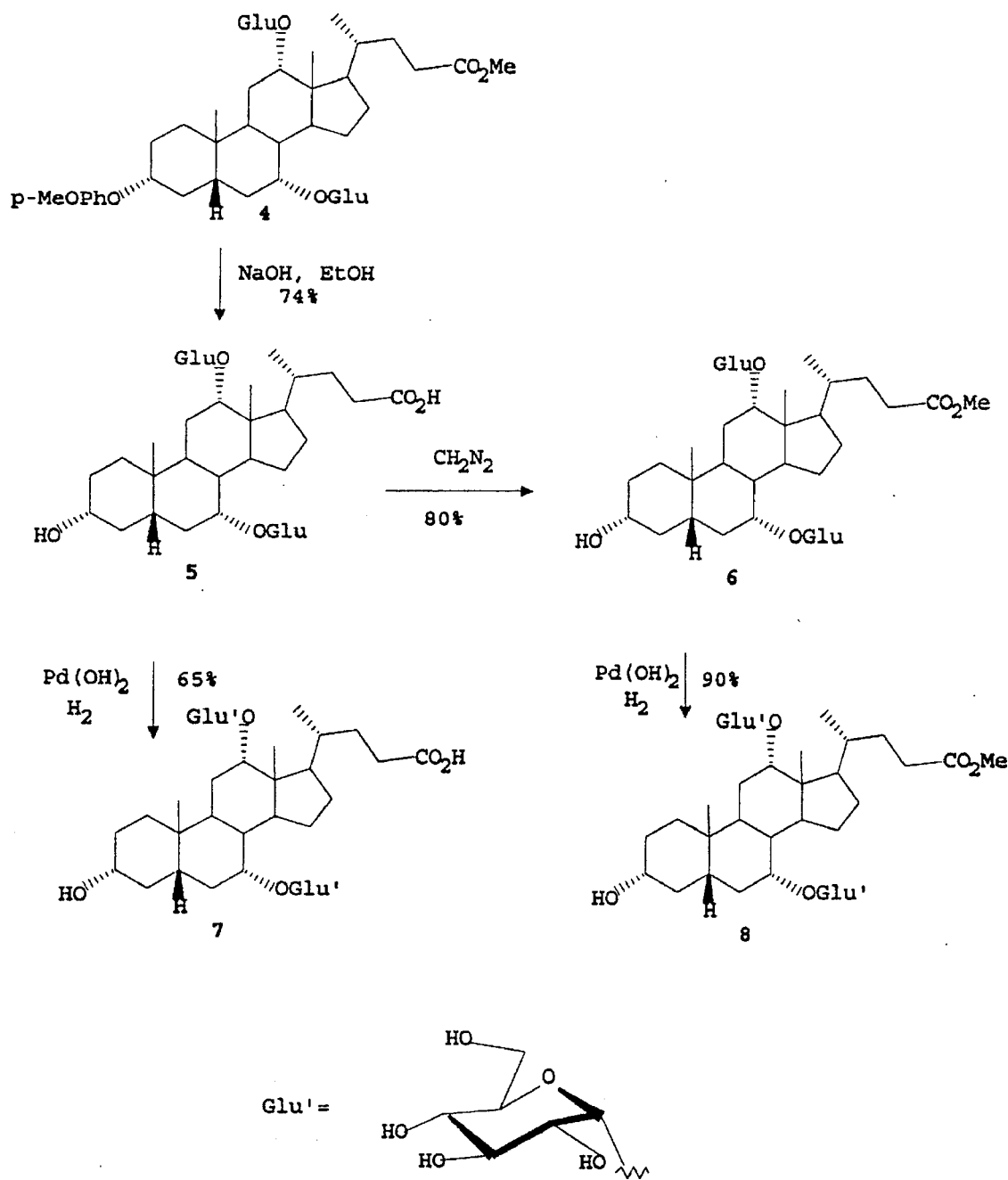
FIG. 14. Continuation of the synthetic scheme for the preparation of 7α,12α-di(1'α-glucosyl)cholic acid and its methyl ester.

Synthesis of 7α,12α-Di(1'α-glucosyl)cholic acid (7) and its methyl ester (S) (See, FIGS. 13–14)

27.1. Methyl Cholate (2)

To a solution of cholic acid (300 g, 0.73 mol) in 1.1 L methanol is added boron trifloride etherate. The mixture is refluxed for 1 h. After cooling, a solid precipitate 2 is collected by filtration. The mother liquor is kept in a refrigerator to give another crop of product. The combined product (295 g, 95%) is dried under vacuum and used for the next reaction without further purification.

27.2. Methyl 3α-O-anisoyl-cholate (3)

A mixture of 2 (58 g, 0.138 mol), p-anisoyl chloride (31.9 mL) and DMAP (60 g) in pyridine is refluxed gently for 16 h. After removal of the solvent, the residue is dissolved in methylene chloride, washed consecutively with 1M aq. HCl, 1M NaHCO$_3$, and dried over Na$_2$SO$_4$. After removal of solvent, compound 3 is isolated by filtration as crystalline solid, which is dried under vacuum to give 53 g (70%): mp 179°–181° C.

27.3. Methyl 3α-O-anisoyl-7α,12α-O-(2,3,4,6-O-tetrabenzylglucosyl)cholate (4)

To a solution of sulfoxide 13 (22.55 g, 34.8 mmol, see, below and FIG. 15) in 150 mL dry toluene is added triflic anhydride (5.9 mL, 35 mmol) at −78° C. After 15 min. stirring at −78° C., 2,5-di-t-butyl-4-methyl pyridine (7.1 g, 35 mmol) in 20 mL toluene is added, followed by the solution of 3 (7.74 g, 14 mmol, above) in 10 mL methylene chloride and 10 mL toluene. The mixture is stirred for 20 min. at −78° C. The dry ice/acetone bath is replaced by a dry ice/acetonitrile bath. The reaction is kept at −60° C. for 1.5 h or until TLC shows no starting material remains. Saturated aq. NaHCO$_3$ (100 mL) is added, followed by 50 mL ether. The organic layer is separated and washed with 10% HCl and saturated aq. NaHCO$_3$ solutions. The organic layer is dried over MgSO$_4$. After removal of the solvent, the residue (37 g) is purified by flash chromatography to give 16 g (70%) of 4 as a thick oil: R$_f$ (30% ethyl acetate in hexane) 0.55; $^1$H NMR δ (CDCl$_3$) 0.76 (s, 3H), 0.99 (s, 3H), 0.9–2.8 (m, 25 H), 3.31 (s, 3H), 3.64 (s, 3H), 3.6–5.1 (m, 32H), 6.0 (d, J=9.0, 1H), 6.8–7.4 (m, 44H), 7.53 (d, J=9, 1H).

27.4. 7α,12α-O-(2,3,4,6-O-tetrabenzylglucosyl)cholic acid (5)

To a solution of 4 (19 g) in 50 mL THF is added 150 mL of 5% NaOH ethanol solution. The resulting mixture is heated under reflux for 24 h. The deep brown suspension is concentrated at a temperature below 40° C. The residue is extracted with 700 mL ethyl acetate, washed with saturated aq. NaCl followed by NaHCO$_3$. The organic layer is dried over MgSO$_4$ and purified by flash chromatography (30–50% ethyl acetate in hexane) to give 12 g (74%) of 5: R$_f$ (40% ethyl acetate in hexane) 0.38.

27.5. 7α,12α-O-Glucosyl-cholic acid (7)

To a solution of 2.5 g of 5 in 20 mL toluene is added 50 mL ethanol followed by 2.5 g Pd(OH)$_2$ (25% on carbon) and 2.5 mL 96% formic acid. The mixture is subjected to hydrogenation at 50 psi for 24 h. The mixture is filtered through filter paper, and the solvent is evaporated. The residue is dissolved in methanol, filtered through a pad of MgSO$_4$, evaporated again leaving 1.6 g of a white solid. The solid is purified by reverse-phase column chromatography (50 mL MCI CHP-20P gel column; 40%–30% H$_2$O in methanol) to give 0.8 g (65%) of 7 as a white powder, which can be recrystallized from methanol/ethylacetate: R$_f$ (silica gel, 60% methanol in chloroform) 0.23; R$_f$ (C-18 reverse phase, 40% H$_2$O in methanol) 0.46; mp. 195° C. (phase transfer); IR (KBr) 3348, 2932, 1705, 1648 cm$^{-1}$; $^1$H NMR (CD$_3$OD) δ0.77 (s, 3H), 0.95 (s, 3H), 1.2–2.5 (m), 3.2–3.5 (m), 3.65–3.9 (m), 4.84 (s). UV λ$_{max}$ (H$_2$O) less than 190 nm; MS m/e 750 (M$^+$+NH$_4^+$); Anal. Calc. C, 59.02; H, 8.26; Found C, 56.25; H, 8.38 (Calc. MW+2 mol. H$_2$O, C, 56.25, H, 8.40).

27.6. Methyl 7α,12α-O-(2,3,4,6-O-tetrabenzylglucosyl)-cholate (6)

Without further purification, 21 g of 5 in 200 mL ether is treated with diazomethane generated from diazald (8.6 g) and NaOH (2 g) for 1 h. The crude product is purified by flash chromatography (22% ethyl acetate in hexane) to give 16.5 g (80%) of 6: R$_f$ (40% ethyl acetate in hexane) 0.43.

27.7. Methyl 7α, 12α-O-glucosyl-cholate (8)

The compound 6 (16.6 g) is hydrogenated in the same manner as the experiment above. Crude product is purified by reverse-phase column chromatography (280 mL MCI CHP-20P gel; 25% H$_2$O in methanol) to give 7.5 g (91%) of 8 as a white powder, which can be recrystallized from methanol/ethyl acetate: R$_f$ (silica gel, 30% methanol in chloroform) 0.25; R$_f$ (C-18 reverse phase, 15% H$_2$O in methanol) 0.48; mp. 173° C. (phase transfer); IR (KBr) 3400, 2934, 1731, 1446 cm$^{-1}$; $^1$H NMR (CD$_3$OD) δ0.90 (s, 3H), 1.08 (s, 3H), 1.2–2.8 (m), 3.77 (s, 3H), 3.4–4.0 (m), 4.99 (s), 5.25 (d, 1H); UV λ$_{max}$ (H$_2$O) 195 nm; MS m/e 764 (M$^+$+NH$_4$$^+$); Anal. Calc. C, 59.47; H, 8.37; Found C, 58.49; H, 8.39; Calc. MW+1 mol. H$_2$O: C, 58.11; H, 8.39.

Example 28

Figure 15:
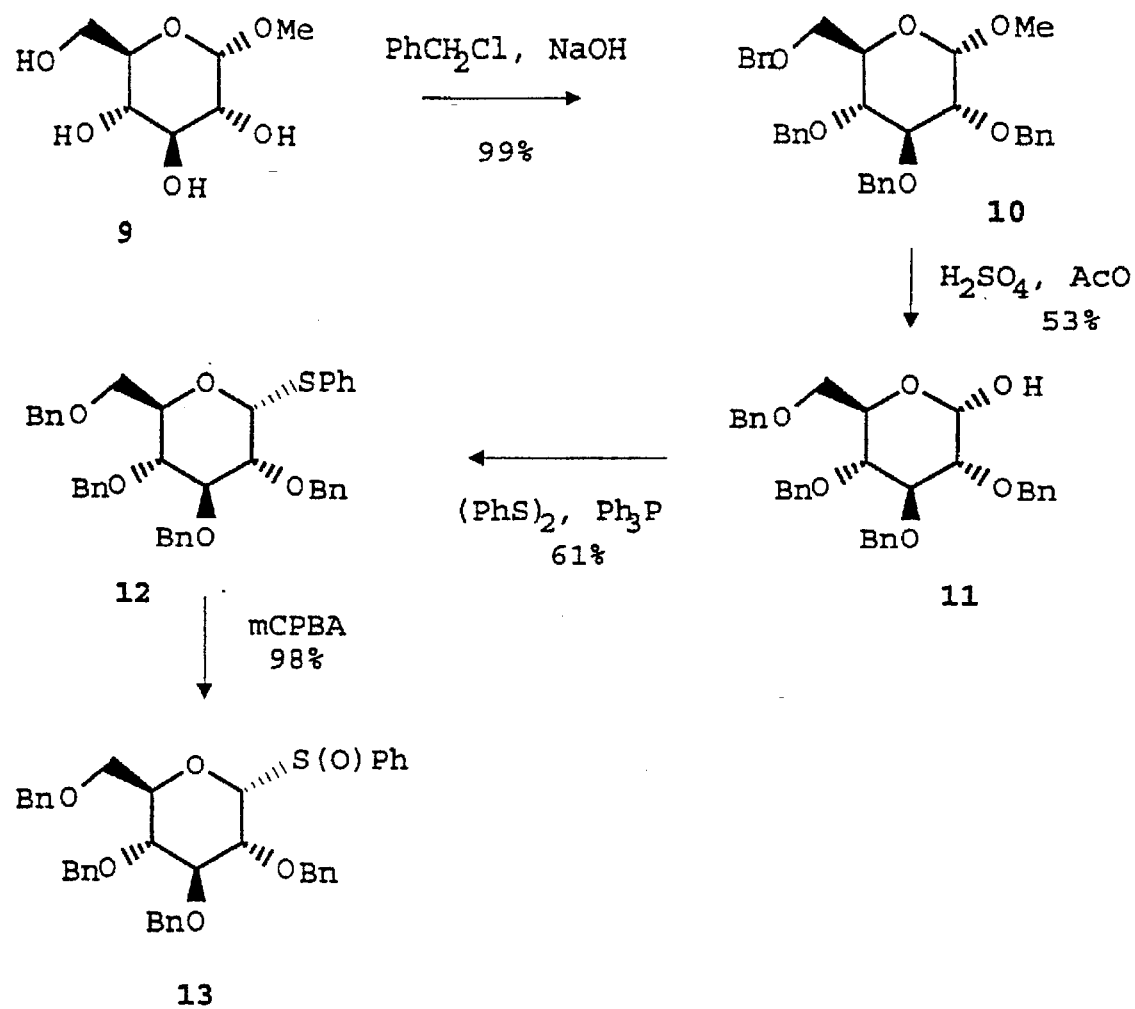
FIG. 15. Synthetic scheme for the preparation of sulfoxide 13 used in the synthetic scheme of FIG. 13.

Preparation of Sulfoxide 13 (See, FIG. 15)

28.1. Methyl 2,3,4,6-tetra-O-benzyl-α-D-glucopyranoside (10)

Methyl-α-D-glucopyranoside 9 (75 g) is dissolved in benzyl chloride (400 mL). To this solution is added potassium hydroxide (250 g). The resulting suspension is heated at 100° C. (water bath temp.) with stirring (mechanical) for 4 h, then cooled to r.t. The mixture is washed with saturated NaCl in ether (500 mL) and dried with MgSO$_4$. The ether is evaporated. The residue is distilled under vacuum (~0.1 mm Hg) at a temperature of 120° C. until no more distillate is collected or the temperature at the distilling head begins to fall. The pot residue is used for the next reaction without further purification.

28.2. 2,3,4,6-Tetra-O-benzyl-α-D-glucopyranose (11)

The crude methyl 2,3,4,6-tetra-O-benzyl-D-glucopyranoside 10 (210 g) is dissolved in glacial acetic acid (500 mL) and the solution is heated to nearly boiling. Hot sulfuric acid solution (3N, 130 mL) is added slowly. Heat is periodically increased and more acetic acid (20 mL) is added to dissolve any precipitate. The final cloudy solution is heated at 100°–110° C. for 2 h. After cooling, crude crystalline product is isolated by filtration and washed several times with methanol to yield product 11 as white crystals (109 g, 53%): mp. 168°–170° C. (Lit. 169°–171° C.).

28.3. Phenyl 2,3,4,6-tetra-O-benzyl-1-thio-D-glucopyranoside (12)

To a solution of 11 (136 g, 0.252 mol) and phenyl disulfide (82.5 g, 0.378 mol) in 600 mL methylene chloride at ice/water bath temperature is added 103 mL tributyl phosphine. The mixture is stirred for 1.2 h, washed with saturated NaHCO$_3$, and dried over MgSO$_4$. After removal of solvent, the residue is crystallized in ethanol to give 100 g (63%) of 12: R$_f$ (20% ethylacetate in hexane) 0.59, mp. 85°–87° C.

28.4. Tetrabenzylglucosyl-1-phenylsulfoxide (Sulfoxide 13)

To a solution of 60 g of 12 in 400 mL methylene chloride at ice-salt bath temperature is added dropwise mCPBA (~50%, 28 g) in 200 mL methylene chloride. The mixture is stirred for 1 h until TLC shows no starting material remains. The mixture is washed with 10% Na$_2$CO$_3$ and dried over MgSO$_4$. The crude product is then purified by flash column chromatography (30% ethyl acetate in chloroform) to give 60 g (98%) of 13: R$_f$ (30% ethyl acetate in chloroform) 0.33; mp. 95°–97° C. Anal. Calc. C, 74.04; H, 6.22; S, 4.93; Found. C, 74.33; H, 6.28; S, 4.70.

Example 29

Figure 16:
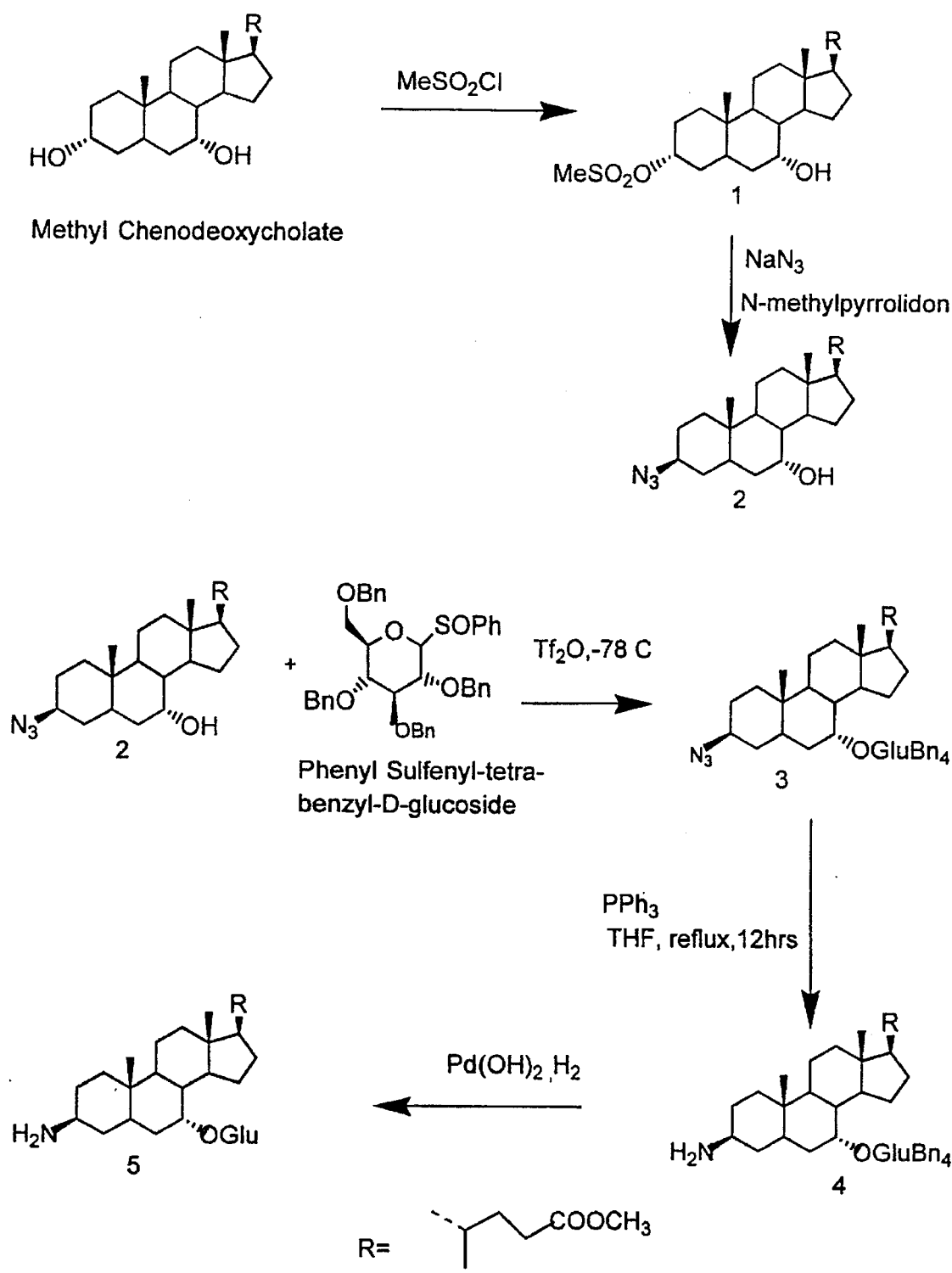
FIG. 16. Synthetic scheme for the preparation of methyl 3β-amino-7α-(1'α-glucosyl)chenodeoxycholate.

Synthesis of the methyl 3β-amino-7α-(1'α-glucosyl)chenodeoxycholate (5) (See, FIG. 16)

29.1. Methyl 3-O-methanesulfonyl-chenodeoxycholate (1)

Methyl chenodeoxycholate (27 g, 61.5 mmol) is dissolved in 100 mL dichloromethane (DCM), pyridine (20 mL). Dimethylaminopyridine (DMAP) (1.22 g, 10 mmol) is then added. The reaction mixture is chilled to 0° C., and methanesul-fonyl chloride (7.5 mL, 11.0 g, 96.7 mmol) is added dropwise. The reaction mixture is heated at 60° C. for 3 h, cooled to r.t., washed with 5% HCl, water, sodium bicarbonate, brine, and dried over sodium sulfate. The solvent is evaporated under reduced pressure (1 mm Hg, 80° C. in a bath) to give mesylate 1 as a thick oil, weight 27 g (90%). This material is used in the next step without further purification.

29.2. Methyl 3β-azido-chenodeoxycholate (2)

Methyl 3-O-methanesulfonyl-chenodeoxycholate (25 g, 51 mmol) and sodium azide (12 g, 185 mmol) are dissolved in 80 mL of N-methylpyrrolidone and heated at 110° C. (in an oil bath) for 3 h. The reaction mixture is cooled to r.t. and poured onto 300 g of ice to give an oil. The oil is extracted with toluene and purified by flash column chromatography (EA-Hexane from 0% to 40% of EA) to give substance 2, which crystallized from hexane. Weight 13 g (60%), m.p. 112°–113° C. (methanol). IR: 3380 (υOH), 2098 (υN$_3$), 1738 cm$^{-1}$ (υCOOMe). $^1$H NMR (CDCL$_3$) δ3.62 (s, 3H), 2.4–1.3 (26H), 0.983 (d, 3H), 0.955 (s, 3H), 0.685 (s, 3H).

29.3. Methyl 3β-azido-7α-O-(tetra-O-benzyl-α-D-glucosyl-1')chenodeoxycholate (3)

Phenyl sulfenyl-tetra-benzyl-D-glucoside (4.05 g, 6.25 mmol) in toluene (150 mL) is treated dropwise at –78° C. with triflic anhydride (1.06 mL, 6.25 mmol) in toluene (10 mL). 2,6-Diisopropyl-4-methyl-pyridine (1.3 g, 6.25 mmol) in toluene (10 mL) is added dropwise. Methyl 3-azido-deoxycholate 2 (2.16 g, 5 mmol) in toluene/dichloromethane (10 mL/10 mL) is added dropwise to the reaction mixture. The procedures are carried out at –78° C. under Ar. After the addition, the stirring is continued 1 h, followed by addition of a saturated solution of sodium bicarbonate (50 mL). The organic layer is washed with 5% HCl, water, brine, and dried over sodium sulfate. Evaporation of the solvent and purification by flash chromatography on silica gel with Ethylacetate (EA)/Hexane (gradient: from 0% to 25% of EA) affords 3.50 g (3.66 mmol, 73% yield) of 3. R$_f$=0.7 (silica, EA/Hexane 2/5). IR (neat) 2108, 1734 cm$^{-1}$; $^1$H NMR (CDCL$_3$) δ7.2–7.44 (m, 20H), 4.31–4.45 (m, 15H), 3.62 (s, 3H), 0.850 (d,3H), 0.671 (s, 3H), 0.649 (s, 3H).

29.4. Methyl 3β-amino-7α-O-(tetra-benzyl-α-D-glucosyl-1')chenodeoxycholate (4)

The azido derivate 3 (2.8 g, 3 mmol) and triphenylphosphine (1.85 g, 7.0 mmol) are dissolved in THF/water (99 mL/1 mL) and the reaction mixture is heated under reflux with stirring for 24 h. The solvent is removed at reduced pressure; the oil residue is dissolved in EA (50 mL), washed with sodium bicarbonate, then brine, then purified by flash chromatography in DCM/EtOH (gradient from 0% to 20% of EtOH) to give 1.5 g (50% yield) of 4, as a semi-solid: R$_f$=0.10 (silica, EA/Hexane 2/5). IR (neat) 3380, 1740 cm$^{-1}$; $^1$H NMR (CDCL$_3$), δ7.15–7.8 (m, 20H), 4.40–5.1 (m, 15H), 3.65 (s, 3H), 0.888 (d, 3H), 0.670 (s, 3H), 0.630 (s, 3H).

29.5. Methyl 3β-amino-7α-O-(α-D-glucosyl-1') chenode-oxycholate (5)

The aminoderivative 4 (1.2 g, 1.3 mmol) is dissolved in 40 mL of EtOH, and a catalyst (10% Pd(OH)$_2$/C, 0.2 g) and formic acid (1 mL) are added. The reaction mixture is hydrogenated in a 0.5 L Parr® vessel at 50 psig for 48 h. The catalyst is filtered off, and the solvent is evaporated under reduced pressure to give a solid residue. Ethyl acetate (5 mL) is added to crystallize out the product. It is filtered and washed with hexane. Weight 0.27 g (yield 37%), m.p. 260° C. (decomposition). The substance is dissolved in water (5 mL) and freeze-dried. $R_f$=0.7 (silica, MeOH/DCM/isopropylamine 60/20/20); IR (KBr) $\upsilon_{COOMe}$1734, $\upsilon_{OH, NH}$3280–3440 cm$^{-1}$; $^1$H NMR (D$_2$O) δ4.88 (s, 1H), 3.2–3.75 (m, 6H), 3.52 (s, 3H), 0.849 (s, 3H), 0.778 (d, 3H), 0.505 (s, 3H). Anal. Calcd. for C$_{31}$H$_{52}$NO$_8$·HCOOH: C,62.5; H, 8.89; N, 2.28%. Found: C,59.0; H, 8.80; N, 2.25%. MS: M+Na$^+$. Calcd. 590. Found 590.

Example 30

Figure 17:
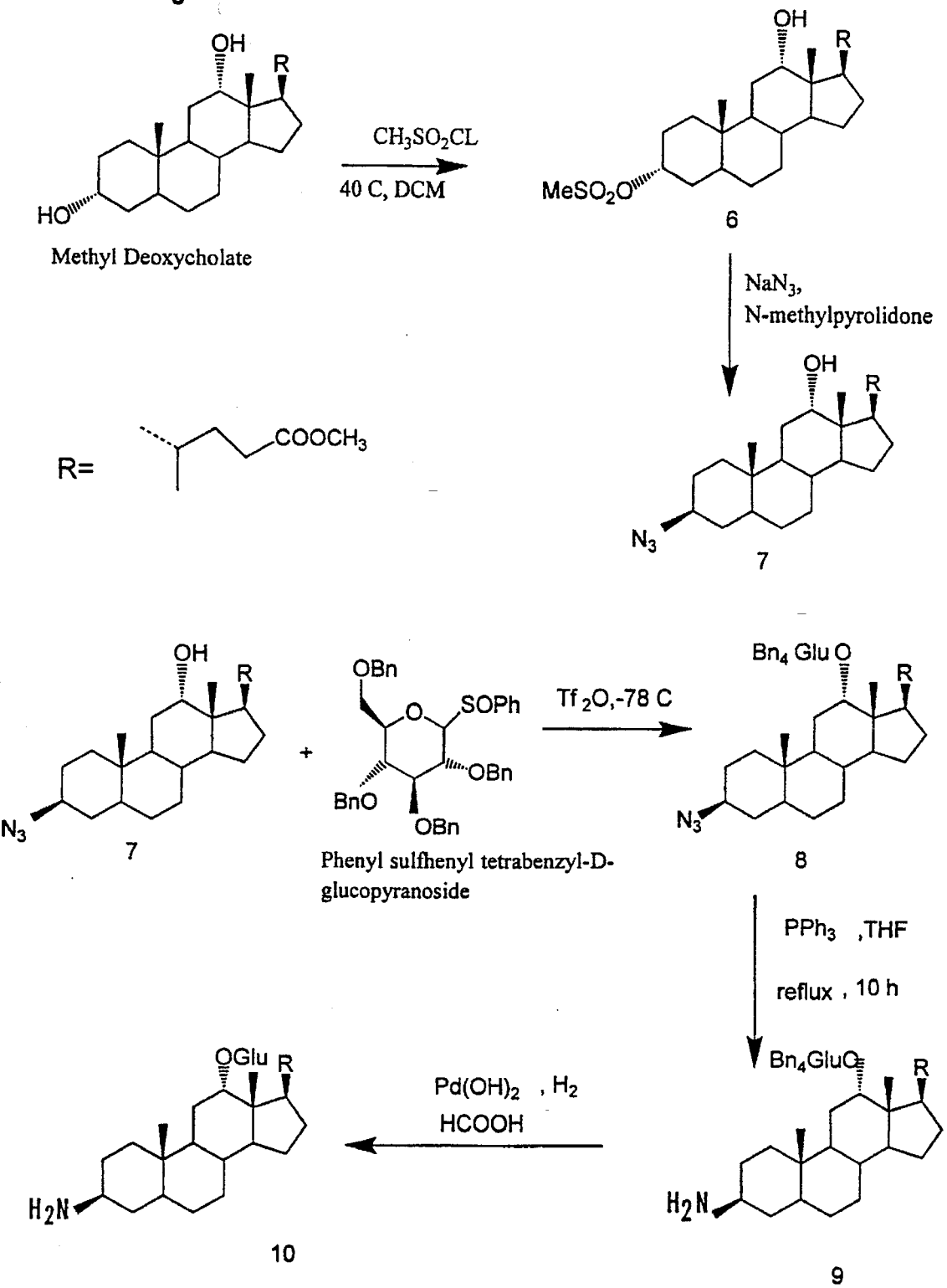
FIG. 17. Synthetic scheme for the preparation of methyl β-amino-12α-(1'α-glucosyl)deoxycholate.

Synthesis of 3-amino-12-O-glucosyl-deoxycholate (10) (See, FIG. 17)

30.1. 3α-O-Methanesulfonyl-deoxycholic acid, methyl ester (6)

The title compound is prepared in the same manner as the methyl 3-O-methanesulfonyl-chenodeoxycholate (1, FIG. 16). It is obtained as an oil and is used in the next step without further purification.

30.2. 3β-Azido-deoxycholic acid, methyl ester (7)

The title compound is prepared in the same manner as the methyl 3-azido-chenodeoxycholate (2, FIG. 16). Yield is 45%, m.p. 128° C. (from methanol). $R_f$=0.6 (silica, EA/Hexane 2/5). IR (KBr) $\upsilon_{OH}$3380, $\upsilon_{N3}$2089, $\upsilon_{COOMe}$1734 cm$^{-1}$. $^1$H NMR (CDCL$_3$) δ3.62 (s, 3H), 2.4–1.3 (m, 26H), 0.986 (d, 3H), 0.942 (s, 3H), 0.691 (s, 3H).

30.3. Methyl 3β-azido-12α-O-(tetra-O-henzyl-α-D-glucosyl-1')-deoxycholate (8)

The title compound is prepared in the same manner as substance 3 of FIG. 16. The yield is 40%. $R_f$=0.75 (silica, EA/Hexane 2/5). IR (neat) 2103, 1742 cm$^{-1}$. $^1$H NMR (CDCL$_3$) δ7.23–7.32 (m, 20H), 4.44–4.97 (m, 15H), 3.67 (s, 3H), 0.854 (d, 3H), 0.688 (s, 3H), 0.643 (s, 3H).

30.4. Methyl 3β-amino-12α-O-(tetra-benzyl-α-D-glucosyl-1')-deoxycholate (9)

The title compound is prepared in the same manner as substance 4 of FIG. 16. The yield is 48%. $R_f$=0.12 (silica, EA/hexane); IR (neat) 1734, 3382 cm$^{-1}$. $^1$H NMR (CDCL$_3$), δ7.1–7.9 (m, 20H), 4.40–4.95 (m, 15H), 3.642 (s, 3H), 0.867 (d, 3H), 0.676 (s, 3H), 0.628 (s, 3H).

30.5. Methyl 3β-amino-12α-O-(α-D-glucopyranosyl-1')-deoxycholate (10)

The title compound is prepared in the same manner as a substance 5 of FIG. 16. The yield is 71%, m.p. 250° C. (decomposition). $R_f$=0.7 (silica, DCM/MeOH/i-propylamine 60/20/20). IR (KBr) 3200–3428 $\upsilon_{OH,NH}$, 1734 $\upsilon_{COOMe}$ cm$^{-1}$; $^1$H NMR (D$_2$O) δ4.95 (d, 1H), 3.85 (s, 1H), 3.69 (s, 1H), 3.62 (s, 1H), 3.38 (d, 2H), 3.53 (s, 3H), 0.85 (s, 3H), 0.78 (d, 3H), 0.51 (s, 3H). Anal. Calcd. for C$_{31}$H$_{52}$NO$_8$·HCOOH; C, 62.5; H, 8.89; N, 2.28%. Found: C,61.5; H, 9.06; N, 2.22%. Mass-spectr: M+Na$^+$. Calcd. 590, found 590.

Example 31

Figure 18:
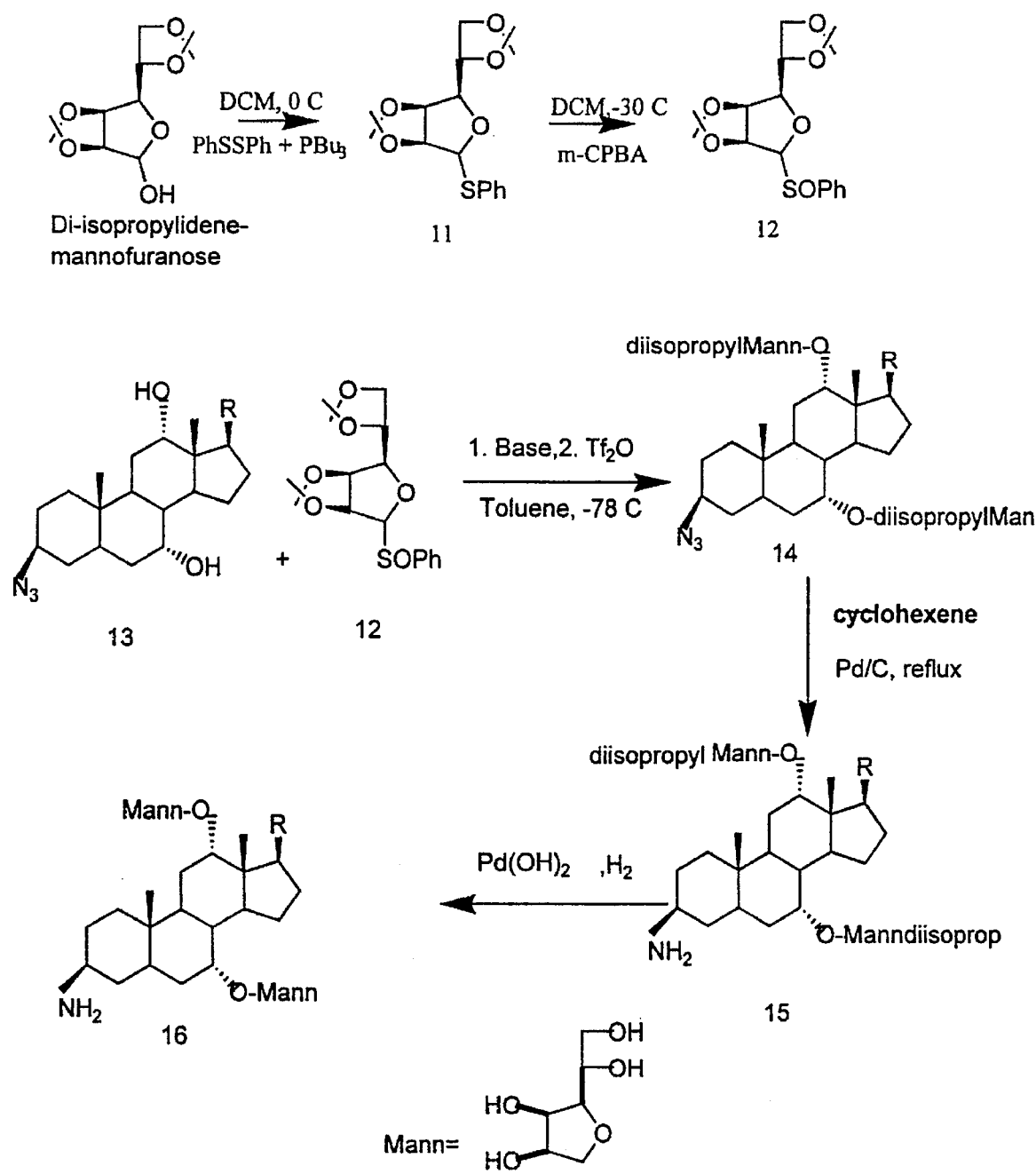
FIG. 18. Synthetic scheme for the preparation of methyl 3α-amino-7α,12α-bis(O-D-mannofuranosyl-1')cholate.

Synthesis of the methyl 3β-amino-7α,12α-bis(O-D-mannofuranosyl-1') cholate (16) (See, FIG. 18.)

31.1. Phenyl 2:3,5:6-diisopropylidene-1-thio-mannofuranoside (11)

A mixture of diisopropylidene-mannose (25 g, 96 mmol), phenyldisulfide (25 g, 115 mmol), and tributyl-phosphine (24.2 g, 20 mL, 120 mmol) in DCM (200 mL) is stirred at 0° C. for 4 h. The solvent and excess of tributylphosphine are then evaporated. Petroleum ether is added and a seed crystal, if available, is added to the stirred solution. The crystals are filtered after 10 h. Weight 22.6 g (yield 80%); m.p. 110° C. (from hexane). $R_f$=0.65 (silica, EA/Hexane 2/5). IR (KBr) 3060, 3030, 1585, 1490, 1453, 1360, 1125, 1090, 1070 cm$^{-1}$. $^1$H NMR (CDCL$_3$), δ7.7–7.0 (m, 5H), 3.95–5.1 (m, 7H), 1.25–150 (q, 12H).

31.2. Phenyl sulfenyl 2:3,5:6-diisopropylidene-mannofuranoside (12)

Mannosylsulfide 11 (22 g, 62 mmol) is dissolved in DCM (150 mL) and chilled to –78° C. Then, m-CPBA (17 g, 70 mmol) in EA (100 mL) is added dropwise over 1 h. When TLC shows the spot of the product 12 only, a saturated solution of sodium bisulfite (100 mL) is poured into the reaction mixture. The organic layer is washed with sodium bicarbonate, brine, dried and evaporated to give an oil, which is purified by flash chromatography (EA/Hexane, gradient from 0% to 50% of EA). Two fractions are collected. The first one $R_f$=0.15 (EA/Hexane 2/5), weight 5.0 g, does not work in the coupling reaction and may be discarded. The second one ($R_f$=0.10, weight 15 g, 65% yield) works in the coupling reaction. Melting point 110° C. IR (KBr) 3060, 3030, 2900, 2870, 1490, 1370, 1230, 1130, 1090 cm$^{-1}$. $^1$H NMR (CDCL$_3$) δ7.7–7.1 (m, 5H), 5.1–4.4 (m, 7H), 1.5–1.25 (m, 12H).

31.3. Methyl 3β-azido-7α,12α-bis(O-2:3,5:6-diisopropylidene-D-mannofuranosyl-1') cholate (14)

The sulfoxide 12 (0.96 g, 2.5 mmol), the methyl 3β-azido-cholate 13 (2.5 mmol), and 2,6-diisopropyl-4-methyl-pyridine (0.63 g, 3.3 mmol) are dissolved in 100 mL of toluene and chilled to –78° C. under Ar. Triflic anhydride (0.56 mL, 3.3 mmol is then added). After the addition, stirring is continued for 1 h at –78° C. The reaction mixture is then allowed to warm to –25° C. during 1 h. The reaction is quenched with a saturated solution of the sodium bicarbonate (50 mL) and the organic layer is washed with water, brine, dried over sodium sulfate and evaporated under reduced pressure. The residue is dissolved in hexane (25 mL), the insoluble part being filtered off. The clear filtrate is purified by flash chromatography (silica, EA/Hexane, gradient from 0% to 25% of EA). The pure substance 14 is isolated as a thick oil: weight 0.45 g (60% yield). $R_f$=0.65 (silica, EA/Hexane 2/5). IR (neat) 2108, 1734 cm$^{-1}$. $^1$H NMR (CDCL$_3$) δ5.18–3.95 (m, 14H), 3.68 (s, 3H), 1.4–1.2 (m, 24H), 0.96 (d, 3H), 0.88 (s, 3H), 0.59 (s, 3H).

31.4. Methyl 3β-amino-7α,12β-bis(O-D-mannofuranosyl-1')cholate (16)

The purified azidoderivative 14 (0.4 g, 04 mmol) is dissolved in methanol/hexene (10 mL/15 mL) and 10% Pd/C (100 mg) is added. The reaction mixture is refluxed under Ar with stirring for 24 h. TLC (silica, EA/Hexane 2/5) shows the disappearance of the starting material and the appearance of a new spot on the base line. The catalyst is filtered off, and the filtrate is evaporated under reduced pressure to give the amino derivate 15 as a thick oil. $R_f$=0.8 (silica, DCM/EtOH 10/1), IR (neat) 3400 ($\upsilon_{NH}$), 1742 ($\upsilon_{COOMe}$). The isopropylidene protecting groups of 15 are hydrolyzed and isolated without further purification as shown in FIG. 18. The crude oil is dissolved in 80% acetic acid (10 mL) and heated under reflux for 6 h. The reaction mixture is diluted with water (20 mL), and a slight precipitate is filtered off. The clear filtrate is evaporated under reduced pressure to give a semi-solid residue of 16. This solid is rinsed with ethyl acetate (5 mL), filtered, dried in a dessicator, dissolved in water, and purified by reverse-phase column chromatography (CHP-20P column; 0–50% methanol-water). Any chromatography solvent is removed under reduced pressure. Freeze-drying affords the substance 16 as a white powder (0.155 g, 50% yield). $R_f$=0.8 (silica DCM/MeOH/iso-Propylamine 6/2/2); IR (neat) $\upsilon_{OH,NH}$3400, $\upsilon_{COOMe}$1734 cm$^{-1}$; $^1$H NMR (CD$_2$OD) $\delta$5.13 (d, 2H), 4.1–3.2 (m, 14H), 3.53 (s, 3H), 1.0–1.2 (m, 25H), 0.817 (d, 3H), 0.744 (s, 3H), 0.465 (s, 3H). Anal. Calcd. for C$_{37}$H$_{63}$NO$_{14}$: C, 59.6; H, 8.44; N, 1.87%. Found: C, 58.8; H, 8.33; N, 2.37%. MS: M-OH+Na$^+$=750. Found 750.

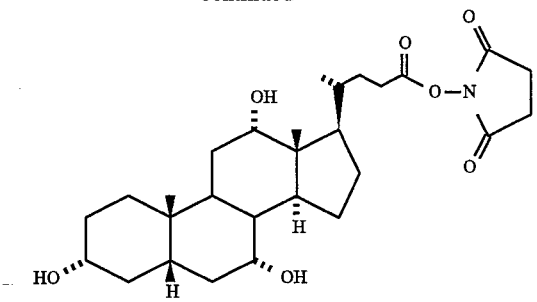

To cholic acid (2 gm, 4.9 mmol) in anhydrous DMF (20 mL), under argon at room temperature, are added DCC (1 gm, 4.9 mmol) and N-hydroxysuccinimide (0.56 gm, 4.9 mmol). The reaction mixture is stirred at room temperature. Dicyclohexylurea starts forming after about 45 min. After 3.5 hours, the dicyclohexylurea is filtered, and the reaction mixture is concentrated under vacuum (using a vacuum pump) overnight to remove DMF. The residue is triturated with Et$_2$O, and the precipitate is filtered. The precipitate is taken up in CH$_3$CN, and the precipitate (left over dicyclohexylurea) is again filtered. Quantitative yield of product is obtained (2.5 gm). TLC (5% MeOH/EtOAc) $R_f$ 0.26. $^1$HNMR (MeOH-d$_4$): $\delta$(ppm)=0.65 (s, 3H, 10axial CH$_3$); 0.84 (s, 3H, 13axial CH$_3$); 0.97 (d, 3H, CH$_3$ on side chain); 2.78 (s, 4H, NHS protons).

32.2. Synthesis of 5'-aminolinked splice acceptor sequence (SEQ. ID NO:1) (ASAS)

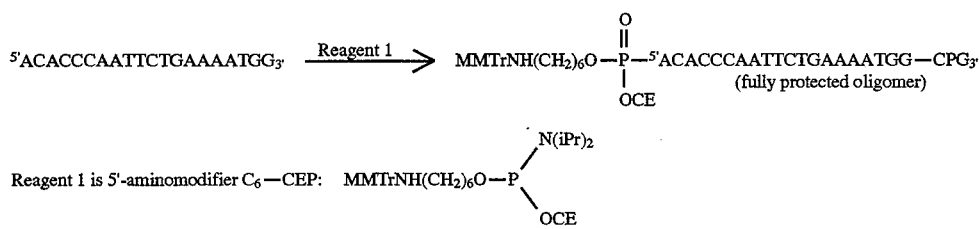

Example 32

Synthesis of cholic acid-ASAS (SEQ. ID NO:1) conjugate

32.1. Synthesis of N-hydroxysuccinimide cholate.

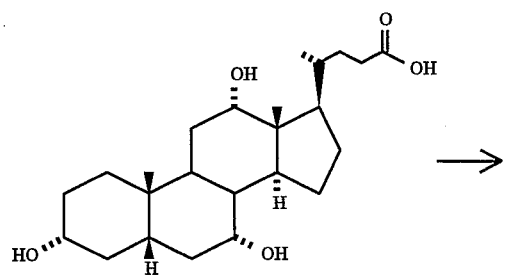

The 5'-aminolinked splice acceptor sequence (SEQ. ID NO:1) oligonucleotide is synthesized on an ABI 392 DNA synthesizer (2-column instrument) using the solid-phase cyanoethylphosphoramidite triester coupling approach. The amino linker is introduced using the 5'-amino modifier C$_6$-CEP reagent from Peninsula Labs. The oligonucleotide is synthesized on scales of 0.2, 1.0 or 10 µmole.

32.3. Conjugation of NHS-cholate to 5'-aminolinked splice acceptor sequence (SEQ. ID NO:1)

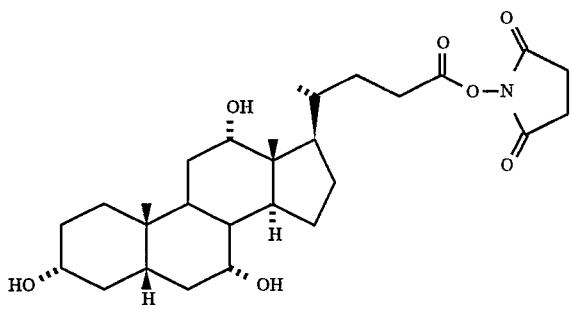 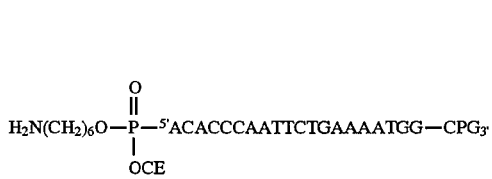

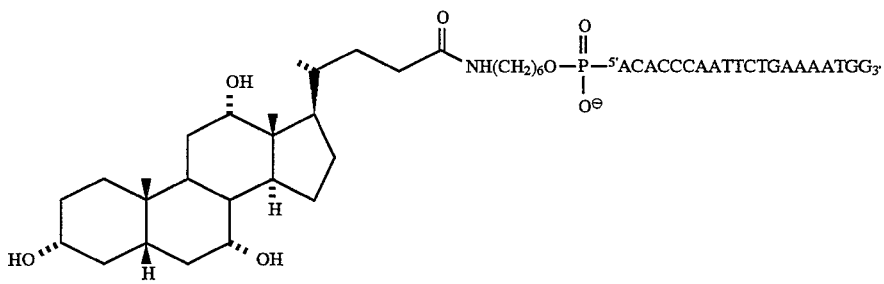

Using solid-phase chemistry

The 5'-aminolinked splice acceptor sequence (SEQ. ID NO:1) synthesized on a 1.0 µmole scale using the $C_6$-CEP reagent is detritylated on an ABI DNA synthesizer using TCA. The top portion of the column is removed and the CPG support is poured into a reaction vessel. A 0.2M solution of NHS-cholate (250 eq, 1 mL) in acetonitrile:water:diisopropylethylamine (8:1:1,v:v:v) is added to the reaction flask. The reaction is gently stirred for one hour at room temperature. The support is filtered and washed three times with acetonitrile:water (8:1,v:v) followed by acetonitrile (3 times). The cholic acid-ASAS (SEQ. ID NO:2) conjugate is removed from the polymer support and fully deprotected by treatment with ammonium hydroxide at room temperature for 1 hour followed by stirring at 55° C. overnight. The reaction mixture is concentrated under vacuum in a speed vac, and the residue is taken up in sterile $H_2O$.

The conjugate is purified by reverse-phase HPLC using a Bondapak $HC_{18}$ HA cartridge (8×100 mm) from Waters. HPLC is carried out on a Waters system fitted with a Waters manual loop injector, a Waters™ 600 Controller, and Waters 490E programmable multiwavelength detector. The Millenium software is used to operate the system and store data. The purification is carried out using a flow rate of 1 mL/min. Buffer A is 0.1M TEAA (pH 7)/$CH_3CN$ (98:2) and buffer B is 0.1M TEAA (pH 7)/$CH_3CN$ (60:40). The following gradient is used: 0% to 37.5% B in 24 min (linear), 37.5% to 100% B in 10 min (linear), 100% B for 11 min (isocratic). Two wavelengths, 254 and 280 nm, are monitored during each injection. For a 1 µmole synthesis, 49 O.D.U. of pure conjugate is obtained with a retention time of 38.2 min on HPLC (RP). $T_m$ of 59.9° C. is recorded at 260 nm in 10 mM Tris-HCl (pH 7), 75 mM NaCl.

Example 33

Synthesis of Cholic Acid-APBS (SEQ. ID NO:2) Conjugate

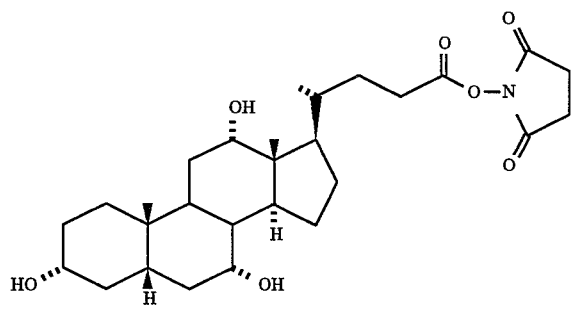 

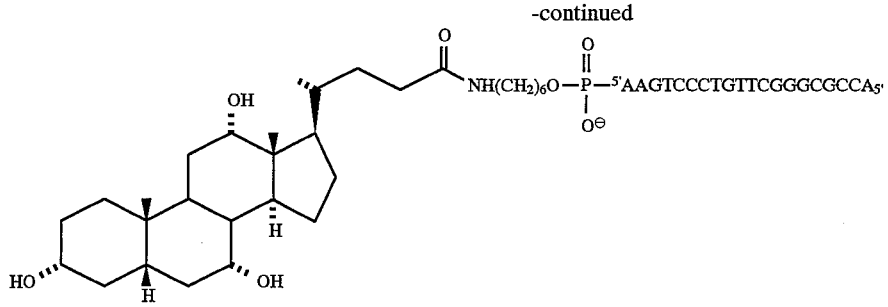

33.1. Synthesis of 5'-aminolinked primer binding site sequence (SEQ. ID NO:2) (APBS)

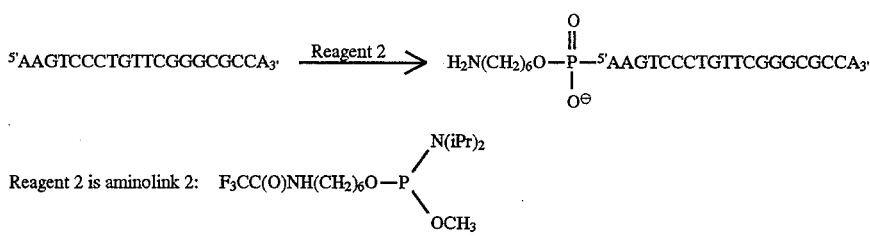

The 5'-aminolinked primer binding site sequence (SEQ. ID NO:2) is synthesized on an ABI 392 DNA synthesizer (2-column instrument) using the solid-phase cyanoethylphosphoramidite triester coupling approach. The amino linker is introduced using the aminolink 2 reagent from ABI. The oligonucleotide is synthesized on scales of 0.2, 1.0 and 10 µmole. It is deprotected by treatment with ammonium hydroxide at room temperature for one hour followed by overnight incubation at 55° C. The reaction mixture is concentrated under vacuum in a speed vac, and the residue is dissolved in sterile $H_2O$. UV ($H_2O$): $\lambda_{max}$=258 nm; $\lambda_{min}$=243 nm.

33.2. Conjugation of NHS-cholate to 5'-aminolinked primer binding site sequence (SEQ. ID NO:2)

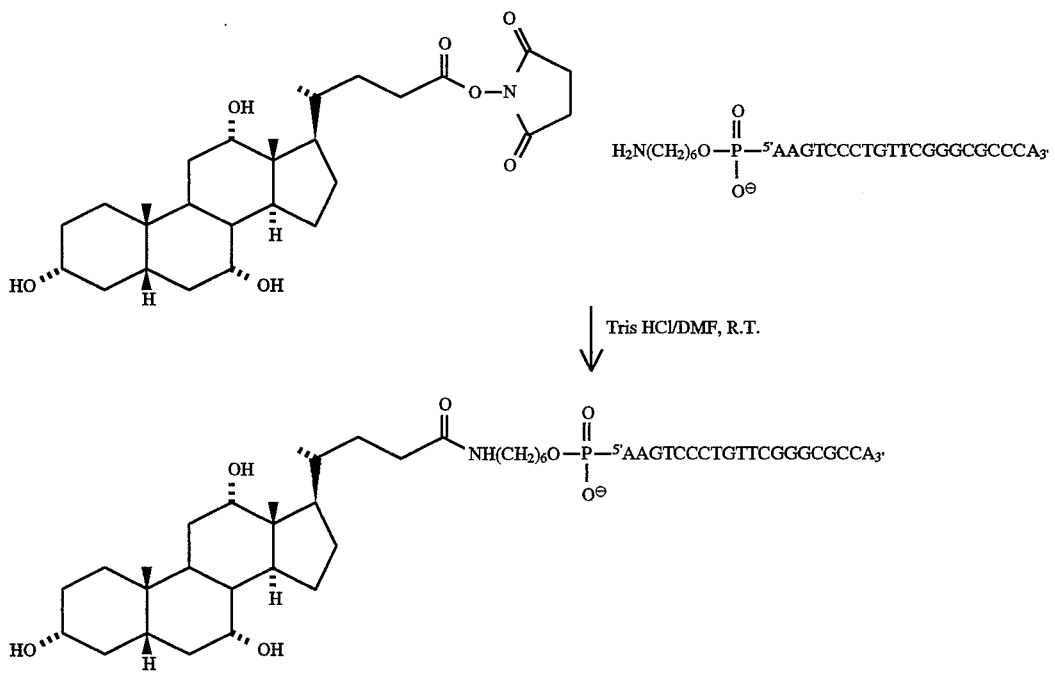

Using solution-phase chemistry 118 O.D.U. of APBS sequence (SEQ. ID NO:2) (0.62 µmole, reaction mixture) is taken up in 2 mL of 0.125M Tris-HCl, pH 7.4. To this solution is added 2 mL of a 15 mM solution of NHS-cholate (31 µmole, 50 eq excess) in CH₃CN. The reaction mixture is kept at room temperature for 4 hours. The reaction mixture is concentrated under vacuum in a speed vac. The residue is taken up in 280 μL of H₂O/CH₃CN (3/1). The extent of reaction is checked by HPLC using a Bondapak HC₁₈ HA cartridge and the gradient and solvent systems elaborated previously. A product peak is observed at 38.05 min retention time (37%) along with some unreacted APBS (SEQ. NO ID:2) and failure sequences from APBS (SEQ. ID NO:2) synthesis at 19.1 min (56%).

Example 34

Synthesis of 7,12-bisglycosylcholic acid ASAS (SEQ. ID NO:2) conjugate

To methyl 7,12-bisglycosylcholate (0.5 gm, 0.67 mmol), dissolved in methanol (5 mL), is added a solution of 5%

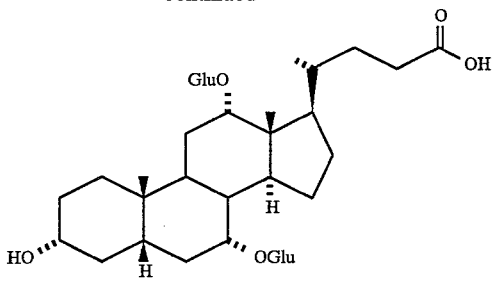

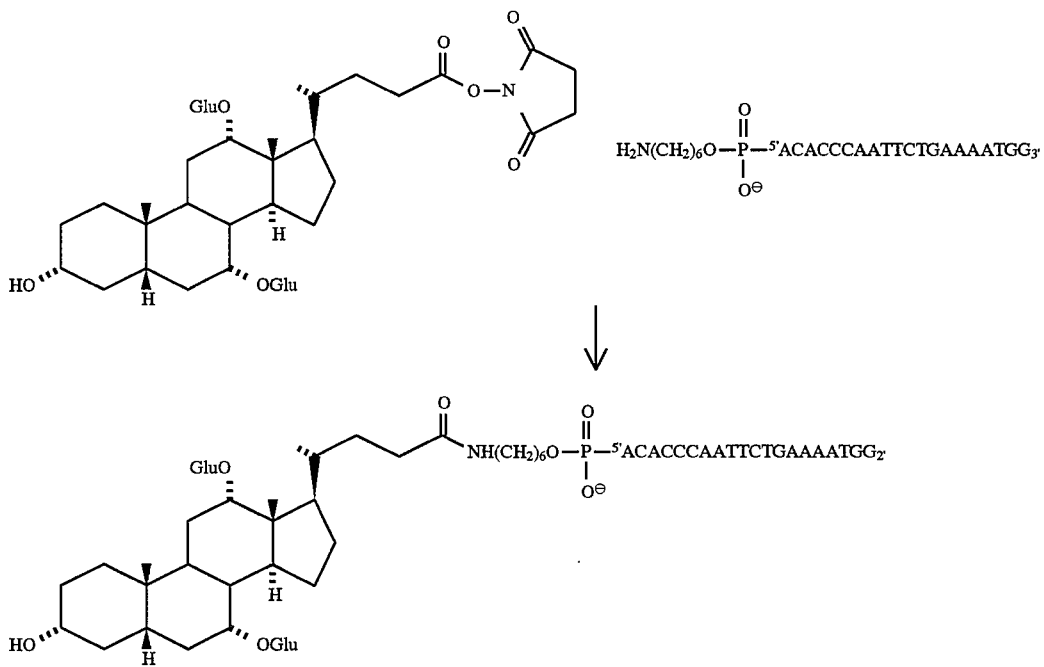

34.1. Synthesis of 7,12-bisglycosylcholic acid

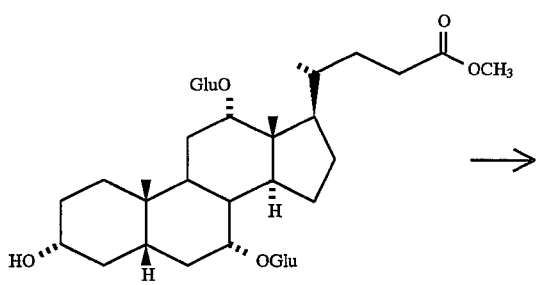

NaOH/MeOH (5.36 gm, 6.7 mmol). The reaction mixture is kept under reflux for one hour. The reaction mixture is then cooled to room temperature and water is added (5 mL). It is neutralized with Dowex 50WX8 H⁺ resin. The resin is filtered, washed with methanol, and the reaction mixture concentrated under vacuum on a rotary evaporator. The reaction mixture is then freeze-dried to remove the water. The product is isolated (without further purification) as a fluffy white crystal (0.48 gm, 98% yield). TLC (C₁₈, EtOH:NH₄OH (80:20)) R_f 0.55; ¹HNMR (MeOH-d₄): δ(ppm) 0.69 (s, 3H, 10axial CH₃); 0.86 (s, 3H, 13axial CH₃); 0.91 (d, 3H, CH₃ on side chain); 4.0 (s, 1H, anomeric proton).

34.2. Synthesis of N-hydroxysuccinimide derivative of 7,12-bisglycosylcholic acid (NHS-BGCA)

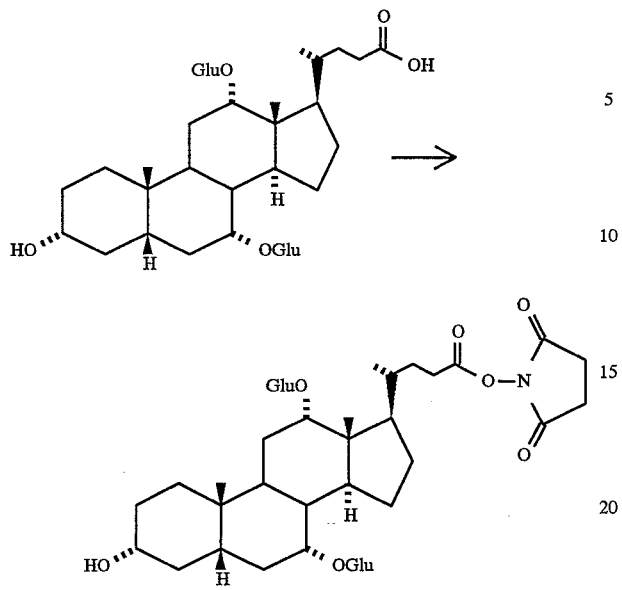

Prior to reaction, the acid prepared above is azeotroped in anhydrous DMF/toluene twice to remove water. To a solution of the acid (0.48 gm, 0.68 mmol) in anhydrous DMF (20 mL) is added DCC (0.168 gm, 0.75 mmol) and N-hydroxysuccinimide (0.079 gm, 0.68 mmol). The reaction

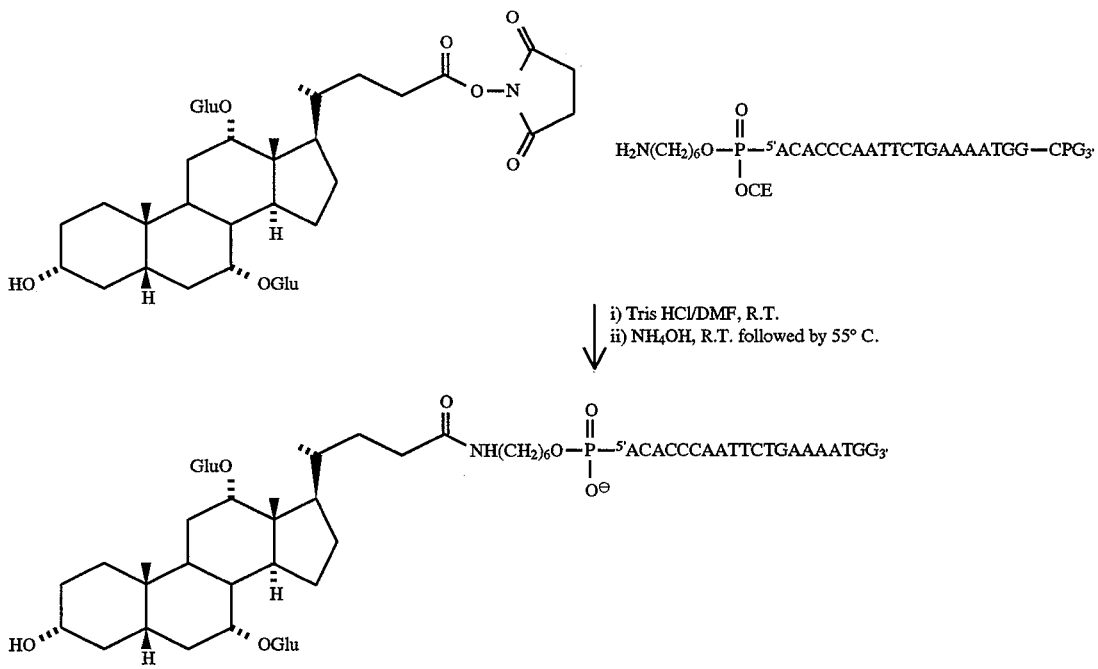

mixture is kept under argon at room temperature overnight. Dicyclohexylurea is filtered off, and the reaction mixture is concentrated under vacuum (using a vacuum pump) to remove DMF. The white crystals obtained are washed with Et$_2$O, and the precipitate is filtered. The product (NHS-BGCA) is isolated (without further purification) as a fluffy white crystal (0.62 gm, quantitative yield). TLC (C$_{18}$, EtOH:NH$_4$OH, 80:20) R$_f$ 0.55; $^1$H NMR (MeOH-d$_4$): δ (ppm) 0.70 (s, 3H, 10axial CH$_3$); 0.87 (s, 3H, 13axial CH$_3$); 2.7 (s, 4H, NHS protons); 4.0 (s, 1H, anomeric proton).

34.3. Conjugation of NHS-BGCA to 5'-aminolinked splice acceptor sequence (SEQ ID NO:1)

Using solid-phase chemistry

The 5'-aminolinked splice acceptor sequence (SEQ. ID NO:1) synthesized on a 0.2 μmole scale using the Peninsula Labs reagent is detritylated on an ABI DNA synthesizer using TCA. The top portion of the column is removed, and the CPG support is poured into a reaction vessel. A 0.2M solution of NHS-BGCA (250 eq, 350 μL) in DMF: 0.125M Tris-HCl (pH 7.4) (5:2) is added to the reaction flask. The reaction mixture is gently 5 stirred at room temperature for two hours. The support is filtered and washed three times with acetonitrile:water (8:1,v:v) followed by acetonitrile (3 times). The BGCA-ASAS (SEQ. ID NO:1) conjugate is removed from the polymer support and fully deprotected by treatment with ammonium hydroxide at room temperature for one hour, followed by stirring at 55° C. overnight.

The conjugate is purified by reverse-phase HPLC using a Bondapak $HC_{18}$ HA cartridge (8×100 mm) from Waters as described earlier for the cholic acid conjugate. For a 0.2 µmole synthesis, 15 O.D.U. of pure conjugate is obtained with a retention time of 37.9 min on HPLC (RP). A $T_m$ of 59.9° C. is recorded at 260 nm in 10 mM Tris HCl, pH 7, 75 mM NaCl.

Example 35

Synthesis of 3-beta-amino-BGCA-ASAS (SEQ. ID NO:1) conjugate

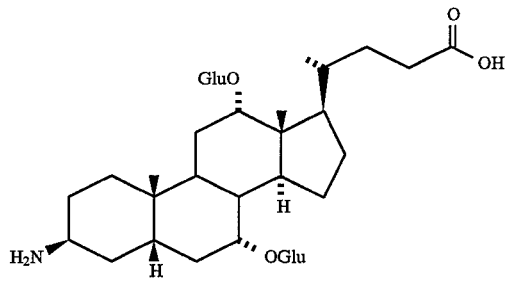

To the methyl 3-beta-amino-7,12-bisglycosylcholate depicted above (210 mg, 0.282 mmol) is added 10 mL of 5% NaOH/MeOH. The reaction mixture is stirred at room temperature for 17 hours followed by an additional 6 hours under reflux. Water is then added and the reaction mixture

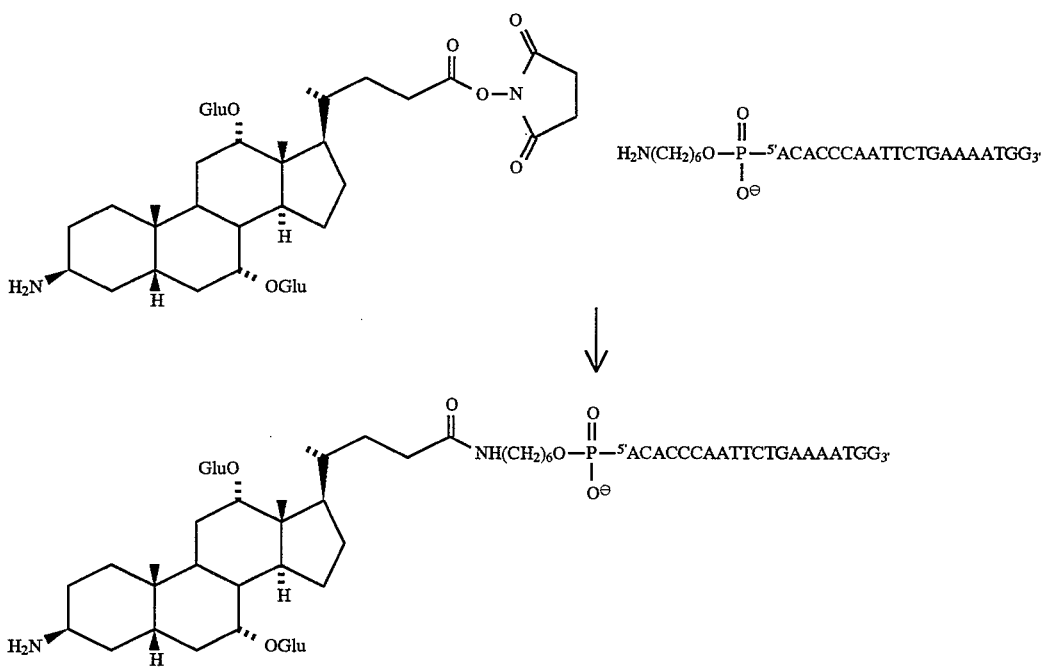

35.1. Synthesis of 3-beta-amino-BGCA from the correspon-ding methyl cholate

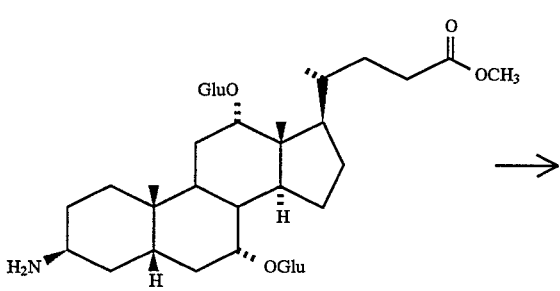

neutralized with Dowex 50WX8 H⁺ resin. The resin is filtered, washed with MeOH, followed by $H_2O$. Methanol is removed under vacuum on a rotary evaporator and the aqueous solution freeze-dried. TLC ($C_{18}$, EtOH:$NH_4OH$, 80:20) $R_f$ 0.48. $^1H$ NMR (MeOH-$d_4$): δ (ppm)=0.68 (s, 3H, 10axial$CH_3$); 0.87 (d, 3H, $CH_3$ on side chain); 0.93 (s, 3H, 13axial$CH_3$); 4.00 (s, 1H, CH—$NH_2$); 4.97 (d, 1H, anomeric proton).

35.2. Synthesis of N-hydroxysuccinimide derivative of 3-beta-amino-BGCA

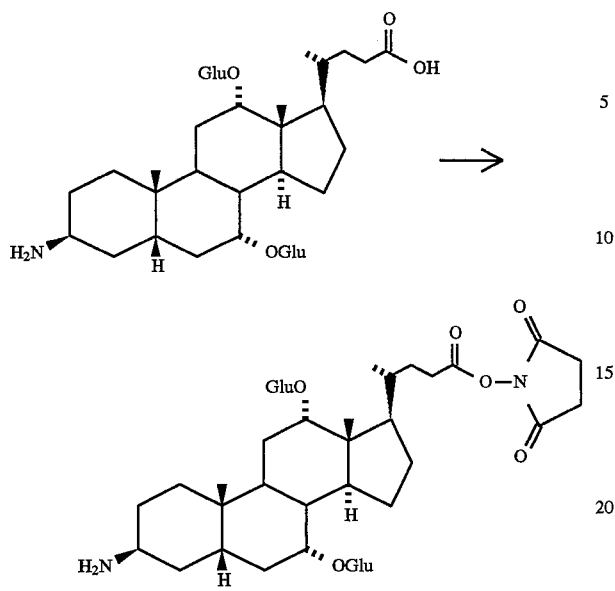

Prior to reaction, 3-beta-amino-BGCA (100 mg, 0.137 mmol) is azeotroped in anhydrous DMF/toluene once to remove water. The residue is taken up in anhydrous DMF (1 mL). To this solution is added N-hydroxysuccinimide (16 mg, 0.137 mmol) and DCC (28 mg, 0.137 mmol). The

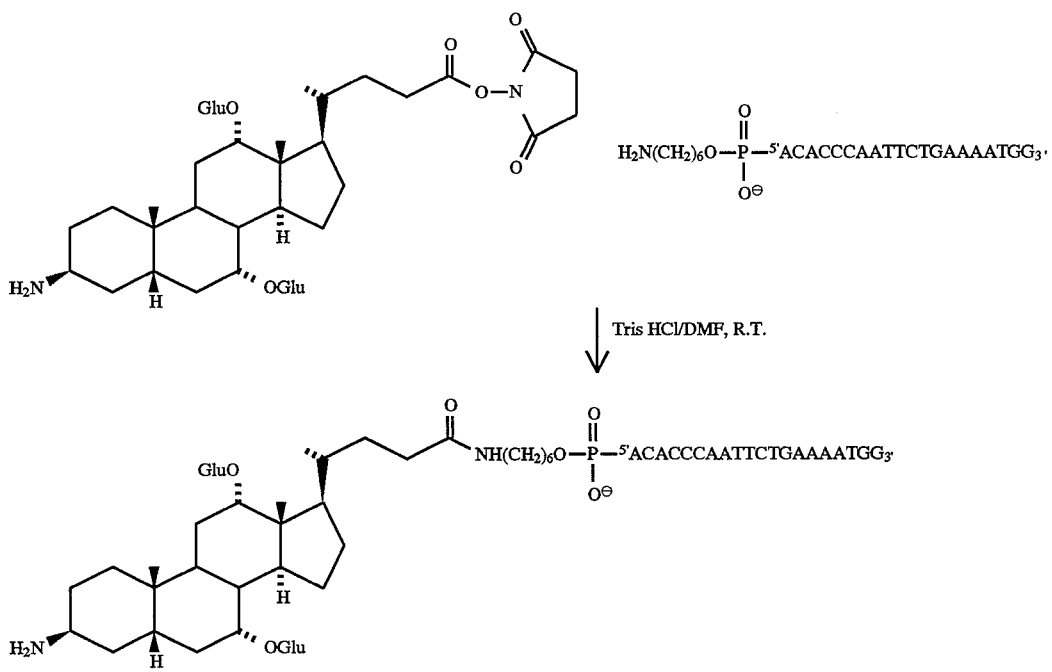

reaction mixture is stirred under argon at room temperature overnight. After about 45 min of stirring, dicyclohexylurea starts precipitating out. After 17 hours, dicyclohexylurea is filtered and washed with methanol. The filtrate is concentrated under vacuum on a rotary evaporator using a vacuum pump. The residue is triturated with Et20. The precipitated product (NHS-3-beta-amino-BGCA) is then filtered and dried under vacuum. TLC ($C_{18}$, EtOH:$NH_4$OH, 80:20) $R_f$ 0.34. $^1$H NMR (MeOH-$d_4$): δ (ppm)=0.68 (s, 3H, 10axial$CH_3$); 0.92 (s+d, 6H, $CH_3$ on side chain+13axial $CH_3$); 2.7 (s, 4H, NHS group); 4.00 (s, 1H, CH—$NH_2$); 4.97 (d, 1H, anomeric proton).

35.3. Conjugation of NHS-3-beta-amino-BGCA to 5'-aminolinked splice acceptor sequence (SEQ. ID NO:1)

Using solution-phase chemistry 1.25 O.D.U. of ASAS sequence (SEQ. ID NO:1) (0.0064 μmole) is taken up in 10 μL of 0.125M Tris-HCl, pH 7.4. To this solution is added 10 μL of a 15 mM solution of NHS-3-beta-amino-BGCA (0.15 μmole, 25 eq excess) in DMF. The reaction mixture is kept at room temperature for 4 hours. Subsequently, the reaction mixture is concentrated under vacuum in a speed vac. The reaction mixture is desalted on an OPC cartridge using the ABI protocol. The residue is taken up in 20 μL of H₂O/CH₃CN (3:1). The extent of reaction is checked by HPLC using a Bondapak HC₁₈ HA cartridge and the gradient and solvent systems elaborated earlier. The product peak is observed at 37.8 min retention time (61%) along with unreacted ASAS (SEQ. ID NO:1) at 19.7 min (27%).

Additional Discussion and Comments Regarding the Preparation and Biological Activity of the Foregoing Oligonucleotide Conjugates For further details of methods of attaching non-radioactive labels to the 5' ends of synthetic oligonucleotides, the interested reader is referred to Agrawal, S. et al., in *Nucleic Acids Res.* (1986) 14:6227–6245 and Gildes, B. D. et al., in *Tet. Lett.* (1990) 31:7095–7098, the dislcosures of which are incorporated by reference herein. Moreover, it has been shown that the affinity of the above-mentioned oligonucleotide sequences (SEQ. ID NOS:1 and 2) for their respective nucleic acid target regions is unaffected by their conjugation to the bisglycosylated bile acids of the present invention. Likewise, it is believed that the inhibitory activity of the above-described oligonucleotide-bisglycosylated bile acid conjugates against viral replication, such as HIV replication, is considerably enhanced relative to the unconjugated oligonucleotides. A variety of biological assays relevant to such activity is known. For example, the following workers have described such assays or other relevant oligonucleotide sequences in the following publications, the disclosures of which are incorporated by reference herein: Marshall, W. S. and Caruthers, M. H., in *Science* (1993) 259:1564–1570; Caruthers, M. H. et al., in *Nucleosides and Nucleotides* (1991) 10:47–59; Stein, C. A. et al., in *Biochem.* (1991) 30:2439–2444; Letsinger, R. L. et al., in *Proc. Nat'l. Acad. Sci. USA* (1989) 86:6553–6556; Goodchild, J. et al. in *Ibid.* (1988) 85:5507–5511. Another antisense sequence that can be used in the instant conjugate is that known as GEM 91, presently being developed by Hybridon as a drug against AIDS.

Example 36

Preparation of Additional Conjugates or Admixtures

The compound of the formula (I) of the present invention is conveniently conjugated to any number of different therpeutically-significant agents including, but not limited to, antitumor, antiinfective, hormone or antihypercholesterolemics, through the substituents attached to carbons C3, C7, C12 or C17 of the steroid nucleus. Preferably, the therpeutically-significant agent is covalently attached to the substituent $R^5$ of the compound of the formula (I). In a specific embodiment, the amine group of the aminosugar moiety of the antitumor agent doxorubicin can be attached via a linker group to the group $R^5$ (e.g., when $R^5$=OH) of the compound of the formula (I) by the methods described in U.S. Pat. No. 4,260,736, the complete disclosure of which is incorporated by reference herein. In a similar manner, various other therpeutically-significant agents are attached covalently to the compound of the invention, as taught, for example, by the methods of the above-referenced '736 patent. For instance, other antitumor agents include, but are not limited to, alkylating agents and antimetabolites (see, e.g., col. 4 of the above-referenced '736 patent for an extensive list of such agents). In addition, other antitumor agents advantageously include mitomycine C, Bleomycin A2, Daunorubicin, Doxorubicin, Sarkomycin, Rubidazone, Vincristine, Vinblastine, mytansine, VP-16, VM-26, and the like. Preferably, the antitumor agent has low oral bioavailability. Still another compound that can be used in the above conjugate is that known as BetaKine being developed by Cetrix Pharmaceuticals, Inc. as an agent against multiple sclerosis and a variety of diseases related to aging or autoimmune disease.

It is understood, however, that the present invention is not limited to the conjugates of the particular therapeutically-significant agent and the compound of the formula (I) but extend to admixtures of the various agents and the compound of the formula (I) or the admixtures of the compound and the conjugates thereof, as previously described. Thus, the present invention is particularly useful for enhancing the biological activity of certain antiinfective agents (such as gentamycin, vancomycin, and other antimicrobial agents), for increasing the bioavailability of certain hormones (such as pituitary mammalian growth hormone, insulin and calcitonin) or for enhancing the effectiveness of certain antihypercholesterolemic agents (such as Mevacor, Zocor, and Pravacol). Indeed, by the enhanced transmucosal availability provided by the compounds of the present invention, a wide range of compounds can be delivered to the subject systemically by routes that do not necessarily require an intravenous or intramuscular route (e.g., intranasal, oral or buccal, gastrointestinal (including jejunal, ileal, and colonic), vaginal or rectal).

Use

The compounds of the invention have been shown to interact with, and permeabilize, biological membranes and to enhance the efficacy of antibiotics and antifungal agents in living cells. Since the compounds of the invention have been shown to permeabilize membranes, and the compounds themselves have no effect on cell growth at the concentrations used, it is presumed that the enhanced efficacy is related to increased delivery of the therapeutically-significant-compounds to the cells.

The utility of the compounds for permeabilizing membranes was demonstrated using an assay (Hoyt, D. W., et al. *Biochemistry* (1991) 30:10155) in which a fluorescein derivative is encapsulated at self-quenching concentrations inside vesicles. An increase in fluorescent intensity upon addition of a test compound indicates leakage of the fluorescein derivative out of the vesicle and therefore implies a disruption or perturbation of the membrane. The compounds of the present invention induced a rapid and significant increase in fluorescent intensity at very low concentrations (0.05 mM–0.5 mM), indicating phospholipid membrane permeabilization.

In addition, both light scattering and turbidity measurements on vesicles treated with selected glycosylated steroid derivatives (at concentrations which induce 100% leakage of carboxyfluorescein) showed that the average size of the vesicles was not significantly different from that of untreated vesicles. Moreover, electron micrographs of vesicles treated with selected glycosylated steroid derivatives (at concentrations which induce 100% leakage of carboxyfluorescein) did not show significant changes in morphology relative to untreated vesicles. The glycosylated steroid derivatives of the present invention, therefore, permeabilize membranes without destroying the vesicles or inducing extensive fusion.

The inventors believe, based on NMR studies of aggregates in solution and also on crystallographic evidence, that the glycosylated steroids of the present invention self-associate and insert into membranes in an associated form, and that membrane permeabilization is related to this process. Although the pure phospholipid vesicles used in this assay do not have the complexity of biological membranes, the inventors have shown that compounds which work well in this assay also enhance the action of therapeutically-significant-compounds (e.g., antibacterial agents and antifungal agents) on living cells. This finding supports the proposition that the ability of the glycosylated steroid derivatives to interact with phospholipid bilayers is related to the ability of the derivatives to enhance the therapeutic efficacy of therapeutically-significant-compounds. It further indicates that the carboxyfluorescein assay is a reasonable initial model system for identifying potential candidates for the permeabilization of biological membranes.

A variation of the above-mentioned assay (Carmichael, V. E. et al. *J. Am. Chem. Soc.* (1989) Vol. 111(2):767–769) was employed to determine whether the compounds make the membranes permeable to protons at extremely low concentrations (0.01 mM–0.005 mM). For this assay, the fluorescein derivative was encapsulated inside vesicles at nonquenching concentrations in a solution of pH 6.5. The vesicles were then diluted into a second solution buffered at a lower pH of 5.5. A compound of Formula (I) was then added at a concentration lower than the concentration required to make the membranes permeable to the fluorescein derivative. After addition of compounds of the Formula (I), the fluorescent intensity within the vesicles decreased, indicating a lower pH resulting from the infiltration of protons from the bulk solution through the vesicles (i.e., the compounds of the present invention resulted in the permeabilization of the vesicles at very low concentrations).

The utility of the glycosylated steroid derivatives of the invention for permeabilizing phospholipid membranes suggested the usefulness of the derivatives for enhancing the permeability of cell membranes, which are composed in large part of phospholipids and other lipids, to therapeutically-significant-molecules. This use was demonstrated in assays testing the efficacy of two different antifungal agents for killing *Crithidia fasciculate*. The use further was demonstrated in assays testing the efficacy of erythromycin for killing *E. coli* ATCC 25922 cells.

ASSAY I

Leakage of Carboxyfluorescein from Vesicles

To a 25 mL round bottom flask 20.5 mg egg yolk (Sigma, average MW 770.4) dissolved in $CHCl_3$/MeOH, 5.0 mg phosphatidyl glycerol (Sigma, MW 772) dissolved in $CHCl_3$/MeOH, and 12.7 mg repurified cholesterol (Aldrich, MW 386.66) were added. The molar ratio of egg yolk; phosphatidyl glycerol:cholesterol was 4:1:5 (66 μmoles total lipid). The solvent was removed on a rotary evaporator. The dried lipid mixture was then put under argon and 3 mL freshly distilled diethyl ether was added. After the lipid had redissolved, 1 mL of carboxyfluorescein dissolved in water (pH adjusted to 7.4) was added to a concentration of 180 mM (the concentration of carboxyfluorescein was determined by UV; the extinction coefficient at pH 7.4 is $5.6 \times 10^4$; $\lambda_{max}$=492). The lipid mixture containing carboxyfluorescein was sonicated under argon in a bath type sonicator at 5°–15° C. for 15–30 minutes. The mixture was then placed on the rotary evaporator and the organic solvent was removed. To separate the carboxyfluoresceinloaded vesicles from unencapsulated carboxyfluorescein, the remaining aqueous vesicle mixture was loaded on a Sephadex G-25 column equilibrated with 145 mM NaCl/10 mM Hepes at pH 7.4. The carboxyfluorescein-loaded vesicles eluted in the first fraction after the void volume while the unencapsulated carboxyfluorescein remained on the column. The purified vesicles were diluted with 145 mM NaCl/10 mM Hepes buffer (pH 7.4) until the fluorescent intensity of the vesicle mixture measured approximately 10.

Because the carboxyfluorescein is encapsulated at self-quenching concentrations in the vesicles, an increase in fluorescent intensity over time indicates that the fluorophore is leaking out of the vesicles into the buffer. 5% Triton-X 100 was added in 50 μL MeOH to a sample of the vesicle solution to determine the maximum possible fluorescent increase (Triton-X 100 is a nonionic detergent that at the high concentration used breaks vesicles by solubilizing the lipids). The ability of each glycosylated steroid to induce the release of carboxyfluorescein from the vesicles was determined by monitoring the increase in fluorescent intensity upon addition of glycosteroid. For each experiment, 50 μL of glycosteroid in methanol (initial concentrations ranged from 0.6145 to 2.458 mM) was added to the cuvette and the fluorescent intensity followed over 10 minutes. A control in which 50 μL pure methanol was added showed that methanol alone does not cause a significant increase in fluorescent intensity. However, several of the glycosteroids efficiently permeabilized vesicle membranes at very low concentrations, permitting the carboxyfluorescein to leak out into the buffer. The results are summarized in Table II.

If the concentrations required to induce significant (i.e., >50%) leakage are taken as a measure of efficacy, then compounds 7, 8, and 11, are the most effective glycosylated steroids tested for permeabilizing phospholipid membranes in this assay. (The numbers of the compounds listed in Table II and III correspond to the compound entries of Table I. For example, compound 8 of Table II corresponds to Entry 8 of Table I.) Compounds 7 and 8 have a cis A/B ring junction and two α-linked glucose sugars attached to the hydrophilic face of the molecule. Compound 11 also has two linked glucose sugars attached to the hydrophilic face of the molecule. Cholic acid, deoxycholic acid, and chenodeoxycholic acid, compounds known to permeabilize biological membranes in other uses (Gordon G. S. et al. *Proc. Nat'l. Acad. Sci. USA* (1985) 82:7419–7423) also permeabilize membranes in this assay, although at much higher concentrations than many of the compounds of the present invention. From these observations, it may be concluded that glycosylation changes the chemical properties of the steroids, making them more efficient at permeabilizing membranes.

TABLE II

| EX | CONCENTRATION (mM)* | % increase in Fluorescence |
| --- | --- | --- |
| Cholic Acid | 0.117 | 0 |
| | 2.341 | 59.1 |
| Methyl Cholate | 0.117 | 25.4 |
| Chenodeoxycholic acid | 0.117 | 17.7 |
| | 1.17 | 80.9 |
| Triton-X 100 | 4.04 | 100 |
| | 1.17 | 46.4 |
| | 0.117 | 18.6 |
| Deoxycholic Acid | 0.117 | 0 |
| | 1.17 | 82.7 |
| 1 | 0.117 | 0 |
| 2 | 0.117 | 10 |
| 3 | 2.34 | 0 |
| 4 | 0.117 | 0 |
| 5 | 0.117 | 57.3 |
| 7 | 0.117 | 89.1 |
| 8 | 0.117 | 89.1 |
| 9 | 0.117 | 24.5 |
| 10 | 0.117 | 0 |

TABLE II-continued

| EX | CONCENTRATION (mM)* | % increase in Fluorescence |
|---|---|---|
| 11 | 0.117 | 98 |
| 13 | 0.117 | 0 |

*Final concentration after dilution.

ASSAY II

Proton Transport across Lipid Membranes

This assay was used to judge the ability of protons to pass across vesicle membranes treated with glycosteroids. Vesicles loaded with carboxyfluorescein at non-self-quenching concentrations were prepared exactly as described above except that the carboxyfluorescein was added to the lipid mixture in 1 mL water (pH 6.5) at a concentration of 1 mM. After sonication under argon and rotary evaporation to remove the diethyl ether, the carboxyfluorescein-loaded vesicles were purified on a Sephadex-G25 column as described above. The concentration of the vesicle solution after purification on the G-25 column was adjusted until the fluorescent intensity equaled 100 after 100-fold dilution into 80 mM NaCl/5 mM Hepes buffer at pH 5.5.

A 100-fold dilution of the vesicle stock into pH 5.5 buffer was made immediately before each experiment and 1 mL of the diluted solution was put in a cuvette. To evaluate the ability of the glycosteroids to facilitate transport of protons across the lipid bilayer, 50 µL of a 0.245M solution of each glycosteroid in methanol was added to the 1 mL vesicle solution in a fluorescence cuvette and the change in fluorescent intensity was monitored over a period of 10 minutes. A significant decrease in fluorescence indicates that the glycosteroid in question facilitates the transport of protons across the membrane. This assay is based on the fact that the fluorescent intensity of carboxyfluorescein is much greater at pH 6.5 than at pH 5.5. If vesicles prepared at pH 6.5 are diluted into a buffer at pH 5.5, the fluorescent intensity will drop over time as the pH gradient across the membrane collapses.

As a control, 50 µL pure MeOH was added and the fluorescent intensity was found not to change significantly. Addition of MeOH at low concentrations therefore does not make the vesicles permeable to protons. The results are summarized in Table III.

TABLE III

| EX | Concentration (mM)* | % Decrease in Fluorescence |
|---|---|---|
| Triton-X 100 | 4.04 | 100 |
|  | 0.0116 | 2.43 |
| Gramicidin | 0.00579 | 87.2 |
|  | 0.000579 | 81.6 |
| Cholic Acid | 0.0116 | 1.0 |
| Methyl Cholate | 0.0116 | 5.4 |
| Chenodeoxycholic Acid | 0.0116 | 8.2 |
| Deoxycholic Acid | 0.0116 | 5.39 |
| 1 | 0.0116 | 7.6 |
|  | 0.00579 | 4.3 |
| 2 | 0.0116 | 8.6 |
|  | 0.00579 | 1.7 |
| 3 | 0.0116 | 35.4 |
|  | 0.00579 | 21.0 |

TABLE III-continued

| EX | Concentration (mM)* | % Decrease in Fluorescence |
|---|---|---|
| 4 | 0.0116 | 12.3 |
|  | 0.00579 | 7.89 |
| 5 | 0.0116 | 26.1 |
|  | 0.00579 | 19.4 |
| 7 | 0.0116 | 19.8 |
|  | 0.00579 | 15.2 |
| 8 | 0.0116 | 32.2 |
|  | 0.00579 | 20.6 |
| 9 | 0.0116 | 43.0 |
|  | 0.00579 | 27.4 |
| 11 | 0.0116 | 22.0 |
|  | 0.00585 | 14.7 |
| 13 | 0.0116 | 70.6 |
|  | 0.00579 | 35.2 |
|  | 0.000579 | 2.8 |

*Final concentration after dilution.

ASSAY III

The Antibiotic Efficacy of Erythromycin With and Without Enhancers

Erythromycin is an antibiotic whose efficacy is known to be increased by compounds that permeabilize cell membranes (Kubesch P. et al. *Biochemistry* (1987) 26:2139–2149). The efficacy of erythromycin, in the presence of novel glycosylated steroid derivatives of the present invention, was evaluated in a plate assay. Briefly, DH2 cells (a mutant strain of *E. coli* K-12, developed at Cold Spring Harbor Laboratories) grown in culture broth to an optical density (O.D.) of about 0.5 were mixed with 2.5 mL melted top agar (Top agar preparation: 10 grams tryptone (DIFCO), 5 grams yeast extract (DIFCO), 10 grams NaCl, 7 grams agar (DIFCO) and 1 mL 1M NaOH dissolved in one liter of pure water and autoclaved for 25 minutes) and then poured onto agar plates (agar plate preparation: 10 grams tryprone, 5 grams yeast, 10 grams NaCl, 15 grams agar, and 1 mL 1M NaOH dissolved in one liter pure water, autoclaved and cooled). After cooling for 15–30 minutes, each plate was divided into a grid and 4 µl of a test solution containing erythromycin (0.5 mM or 1.0 mM) in methanol, or erythromycin plus test compound (20 mM) in methanol, was spotted on each section of the grid. The plates were incubated for sixteen (16) hours at 37° C. and then examined for zones of inhibition (i.e., clear areas in sections of the grid where the test solution inhibited bacterial cell growth). Each section of the grid was scored. The section of the grid containing erythromycin alone at 1.0 mM concentration was used as a standard for evaluating efficacy, with the other sections scored relative to this. The results, summarized in Table IV below show that 3α-O-p-methoxybenzoyl-cis-5, 10-bis-α,α-7,12-glucosyl cholic acid methyl ester (referred to elsewhere herein as "CME") is the best "enhancer" in this assay. Of the non-glycosylated, bile acid derivatives used in this assay, only deoxycholic acid and its sodium salt showed any effect. Chenodeoxycholic acid and cholic acid and its salts did not have a detectable effect on the antibiotic efficacy of erythromycin in this assay. Interestingly, deoxycholic acid salts also have been shown to be more effective than chenodeoxycholic acid salts and cholic acid salts in enhancing the uptake of insulin through nasal membranes (Gordon G. S. et al. *Proc. Nat'l. Acad. Sci. USA* (1985) 82:7419–7423).

TABLE IV

| COMPOUND (20 mM) | ERYTHROMYCIN (mM) | EFFECT |
|---|---|---|
| Cholic Acid | 1.0 mM | — |
| Cholic Acid | 0.5 mM | — |
| Sodium Cholate | 1.0 mM | — |
| Sodium Cholate | 0.5 mM | — |
| Methyl Cholate | 1.0 mM | — |
| Methyl Cholate | 0.5 mM | — |
| Chenodeoxycholic Acid | 1.0 mM | — |
| Chenodeoxycholic Acid | 0.5 mM | — |
| Deoxycholic Acid | 1.0 mM | + |
| Deoxycholic Acid | 0.5 mM | + |
| Sodium Deoxycholate | 1.0 mM | + |
| Sodium Deoxycholate | 0.5 mM | + |
| CME | 1.0 mM | +++ |
| CME | 0.5 mM | +++ |
| 3α-O-benzoyl-trans-5,10-bis-α,α-7,12-glucosyl cholic acid methyl ester [BTME] | 1.0 mM | + |
| BTME | 0.5 mM | + |
| 3α-OH-cis-5,10-bis-α,α-glucosyl cholic acid K⁺ | 1.0 mM | + |
| 3α-OH-cis-5,10-bis-α,α-glucosyl cholic acid K⁺ | 0.5 mM | + |

—: erythromycin alone at 1.0 mM (baseline) and all lesser effects
+: enhancement relative to baseline
+++: significant enhancement relative to baseline The above plate assay was repeated using lower concentrations of CME and comparing its efficacy as an enhancer to that of the non-glycosylated parent, 3α-O-p-methoxybenzoyl-cis- 5,10-cholic acid methyl ester (the non-glycosylated form of CME and referred to elsewhere herein as "CDE"). The results, summarized in Table V below, show that while CME acts as an enhancer at very low concentrations, the non-glycosylated parent compound does not function as an enhancer. This demonstrates that the sugars are critical for enhancing effect.

TABLE V

| COMPOUND (mM) | ERYTHROMYCIN (mM) | EFFECT |
|---|---|---|
| 1.0 mM CDE | 0.1 mM | — |
| 0.1 mM CDE | 0.1 mM | — |
| 0.1 mM CME | 0.1 mM | + |
| 0.1 mM CME | 0.01 mM | + |
| 0.01 mM CME | 0.01 mM | + |
| 0.001 mM CME | 0.01 mM | + |
| 0.001 mM CME | 0.001 mM | — |

—: no detectable clearing (zone of inhibition)
+: visible clearing

ASSAY IV

Efficacy of Antifungal Agents on Protozoa with and without Added Glycosylated Steroid Derivatives CME, identified in both Assay I described above (compound 8 in the carboxyfluorescein assay) and in Assays II and III described above, as a good membrane permeabilizing agent, was tested for its ability to enhance the efficacy of two different antifungal agents on the protozoan *Crithidia fasciculate*. The ability of the non-glycosylated parent steroid to enhance efficacy was also studied. The studies were carried out as described in Pascal R. A. et al. *Biochemistry* (1983) 22:171–178 and Rahman M. D. et al. *J. Med. Chem.* (1988) 31:1656–1659. Briefly, flasks containing 25 mL of growth medium (Preparation: 1.5 grams sucrose, 0.5 grams yeast extract, 0.4 grams tryptone and 0.25 mL triethanolamine dissolved in 100 mL water and pH adjusted to 8.0 with 10M HCl. Autoclave. After cooling, add 100 μL hemin (SIGMA) (2 mg hemin/1 mL 0.1N NaOH) and 20 mg. streptomycin sulfate (SIGMA)) and the antifungal agent and/or the glycosylated or nonglycosylated steroid derivatives were inoculated with aliquots of *C. fasciculate* (250 μL of culture containing approximately $1 \times 10^6 - 1 \times 10^7$ cells) (Preparation of culture: *C. fasciculate* in glycerol added to culture medium and grown, with shaking, for three (3) days at 26° C.; then stored at 0° to 4° C.). The cultures were incubated, with shaking, at 25° C. and growth was monitored by changes in absorbance at 535 nm (relative to the uninoculated medium).

Figure 2:
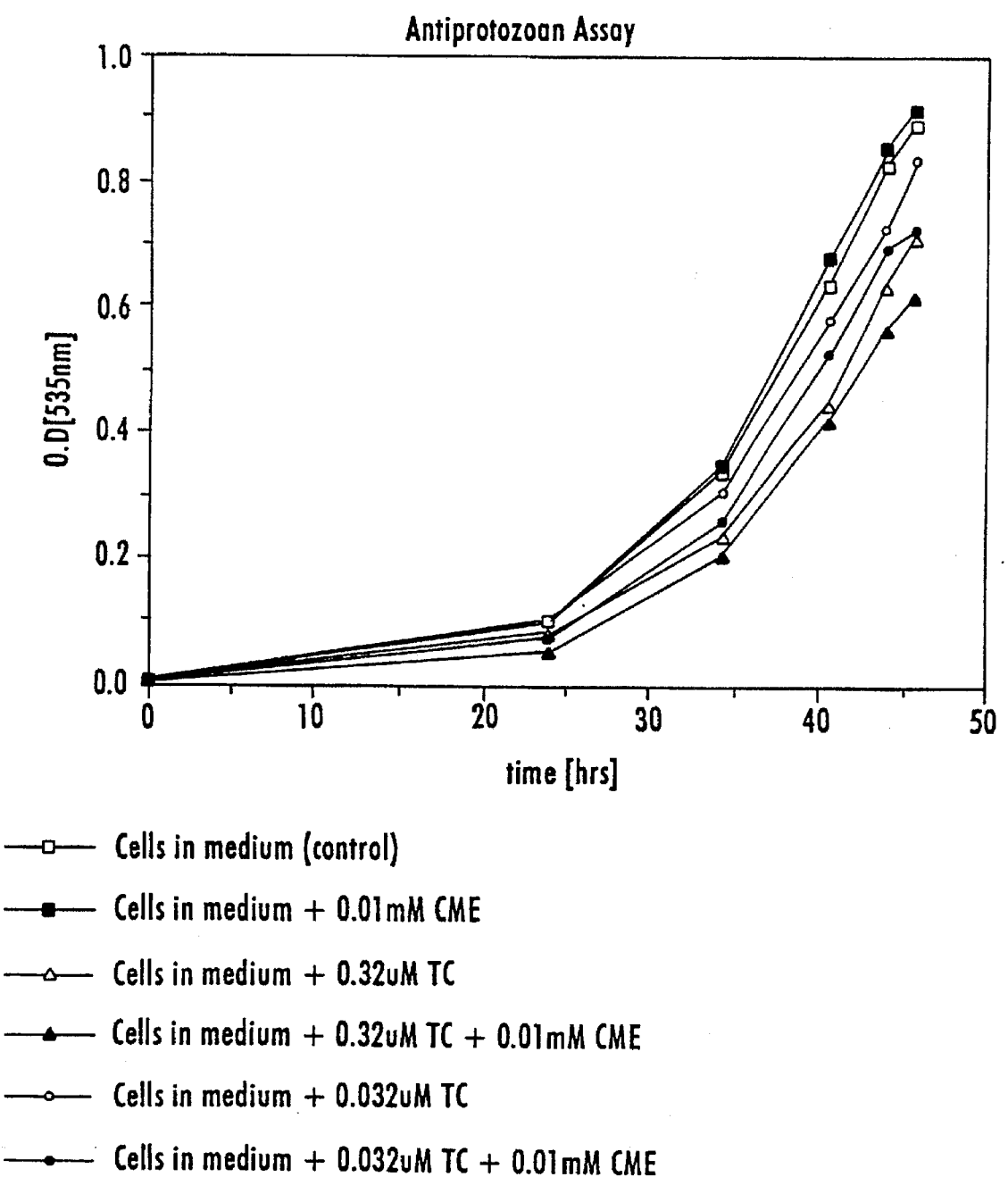
FIG. 2. A graph depicting the enhancing effect of CME, a novel glycosylated steroid derivative of the present invention, on the efficacy of thiacholestanol (TC), an antifungal agent.
Figure 3:
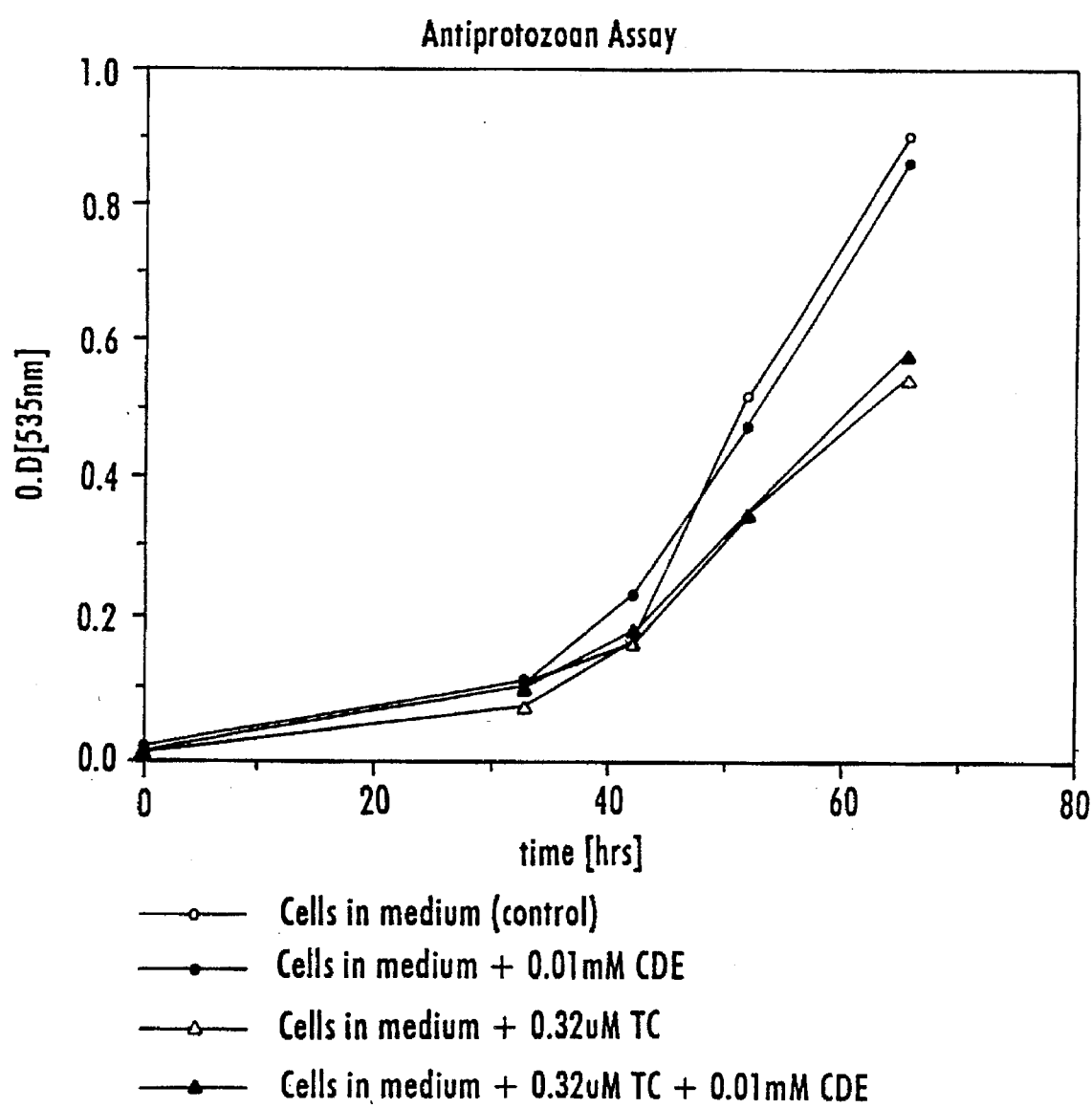
FIG. 3. A graph depicting the lack of an enhancing effect of CDE, the non-glycosylated version of CME, on the efficacy of thiacholestanol (TC), an antifungal agent.
Figure 4:
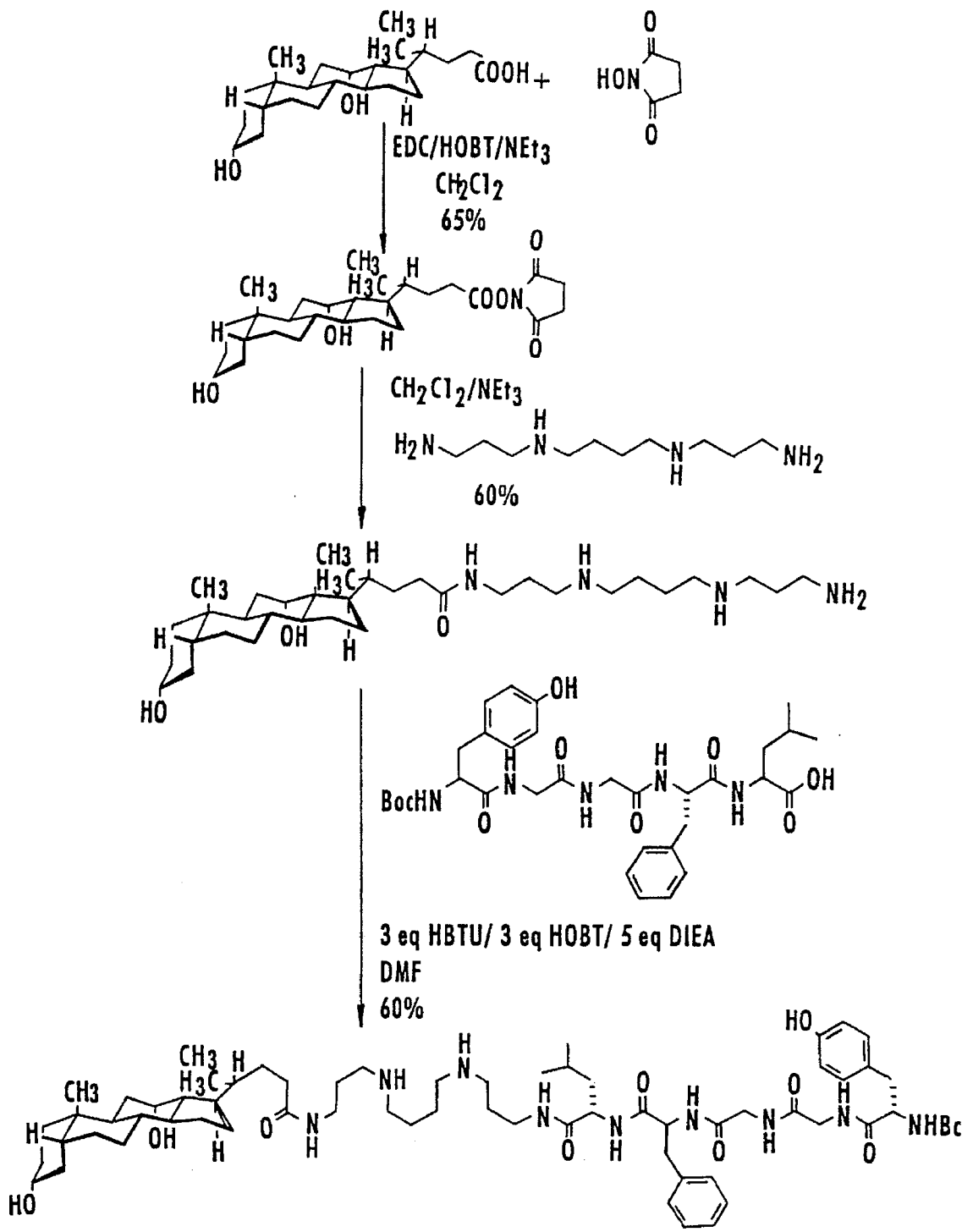
FIG. 4. Illustrates the synthetic scheme for the "synthetic" endorphins of the present invention.
Figure 5:
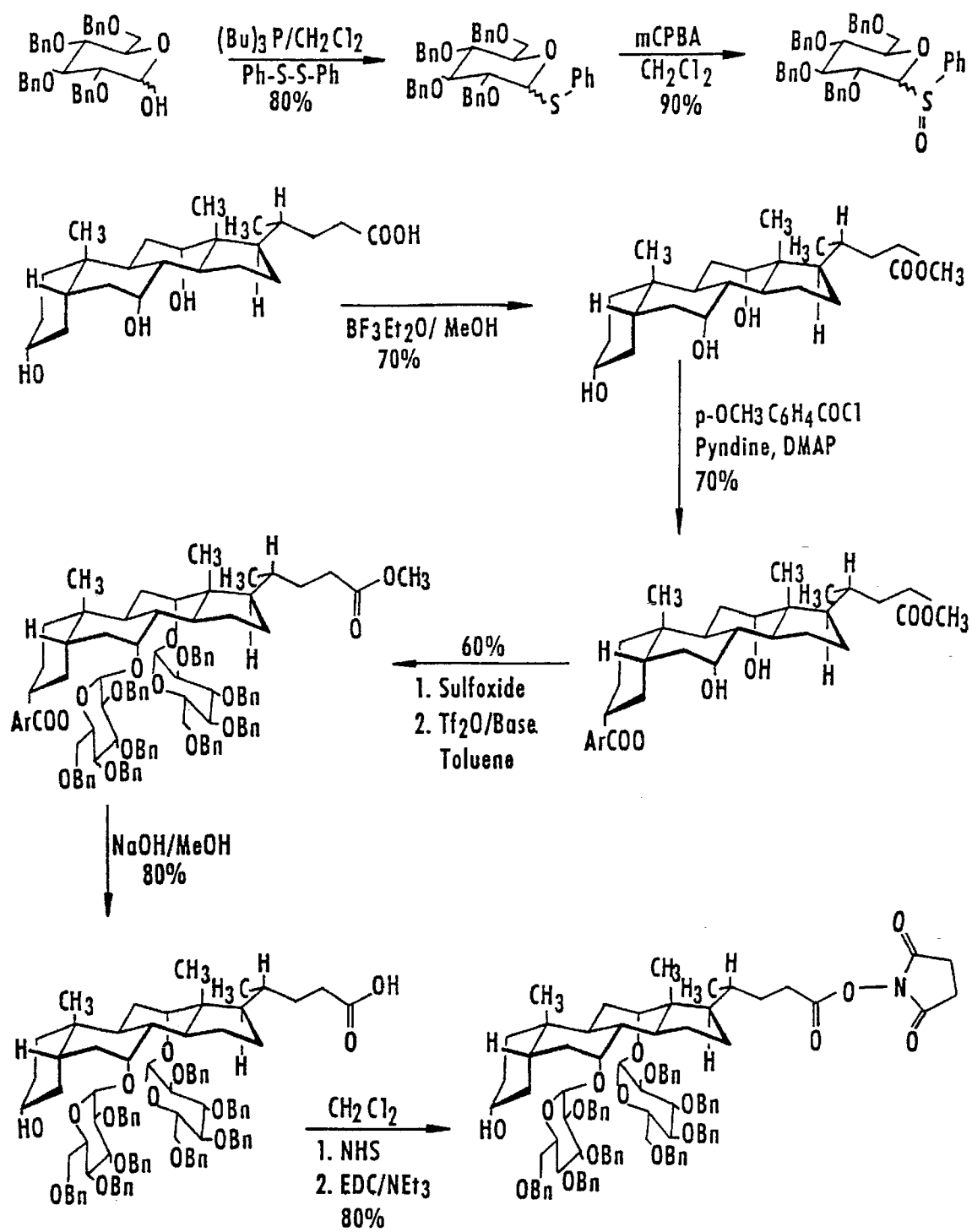
FIG. 5. Illustrates synthetic aspects of an endorphin mimic.
Figure 6:
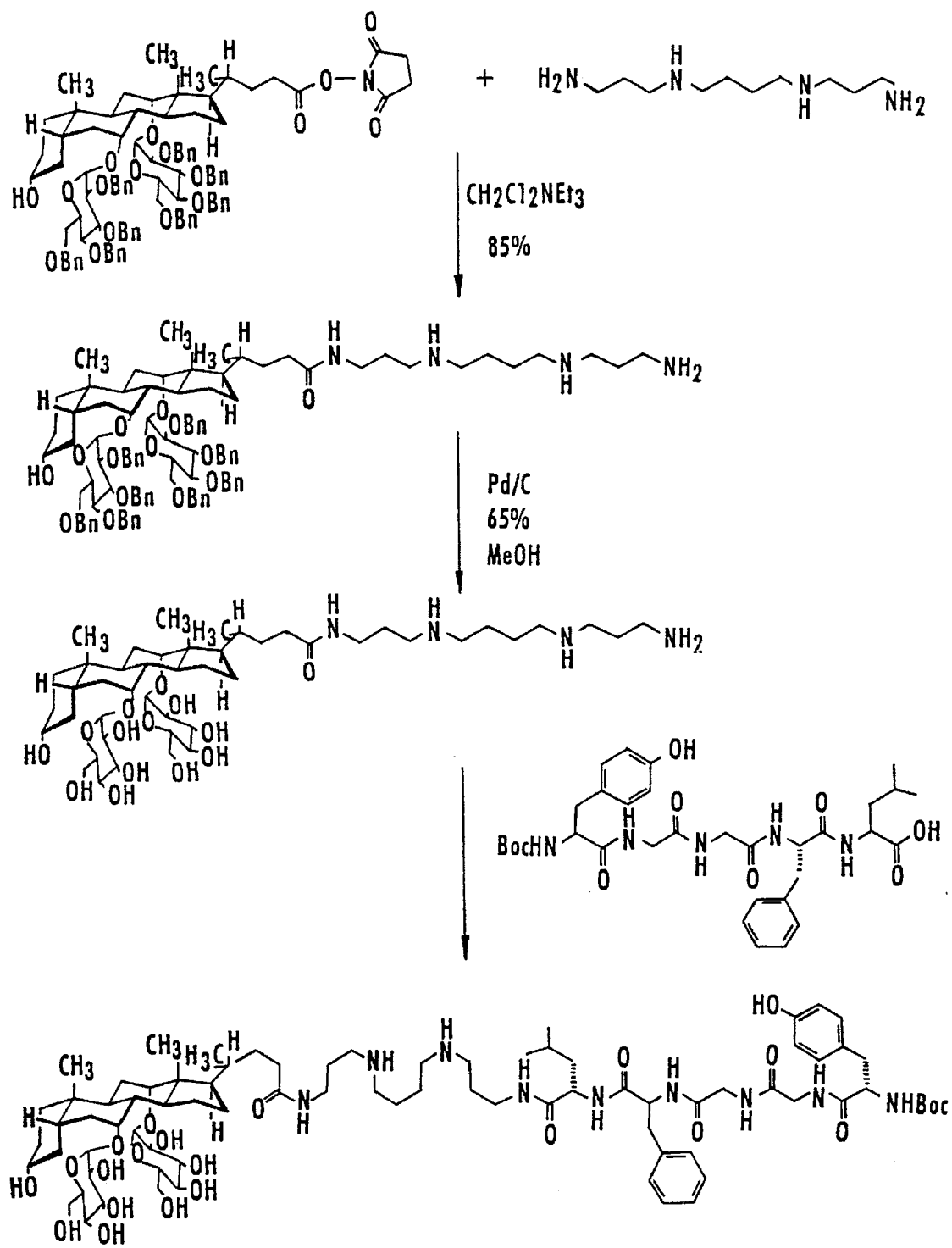
FIG. 6. Illustrates the continuation of the synthetic scheme for the preparation of an endorphin mimic.

Two different antifungal agents were used in the assays. The first was 10-thiastearic acid (10-TSA; see Rahman M.D. et al. *J. Med. Chem.* (1988) 31:1656–1659), which has an $IC_{50}$ of 10 μM; the second was 24thiacholestanol (24-TC; see Rahman M.D. et al. *J. Lipid Research* (1988) 29:1543–1548; Rahman M.D. and Pascal R. A., *J. Biol. Chem.* (1990) 265:4989–4996), which has an $IC_{50}$ of 0.32 μM. The results, depicted in FIGS. 1, 2, and 3, demonstrate that the presence of CME enhances the efficacy of 10-TSA dramatically, allowing it to be used in 10- to 100-fold lower concentrations than otherwise necessary to achieve 50% inhibition of growth (FIG. 1). The presence of CME also was shown to enhance the efficacy of 24-TC (FIG. 2). The non-glycosylated parent steroid (CDE) was not observed to act as an enhancer in this assay (FIG. 3).

ASSAY V

Efficacy of Derivative-Compound Conjugate on the Protozoa *Crithidia fasciculate*

A novel glycosylated steroid derivative of Formula (I) is conjugated to a therapeutically-significant-compound by methods known in the art for coupling an acid group to an amine (i.e, to form an amide). The ability of the derivative-compound-conjugate to inhibit the growth of *Crithidia fasciculate* is evaluated as described in Pascal R. A. et al. *Biochemistry* (1983) 22:171–178 and Rahman M.D. et al. *J. Med. Chem.* (1988) 31:1656–1659. Briefly, flasks containing 25 mL growth medium alone, growth medium plus 24-TC at 0.32 μM concentration (the $IC_{50}$ level), and growth medium plus the derivative-compound-conjugate at 0.32 μM concentration are inoculated with aliquots of *C. fasciculate* (250 μL of culture containing approximately $1 \times 10^6 - 1 \times 10^7$ cells). The cultures are incubated with shaking at 25° C. and growth is monitored by changes in absorbance at 535 nm (relative to the uninoculated medium). Enhanced efficacy of the derivative-compound conjugate relative to the non-conjugated therapeutically-significant-compound would be reflected in a lower rate of growth (i.e., lower absorbance over time). The $IC_{50}$ level of the derivative-compound-conjugate can be measured by repeating the experiments with different concentrations of derivative-compound-conjugate to define the concentration that causes a 50% inhibition of growth relative to the culture containing *C. fasciculate* alone.

In another set of experiments, the flasks of growth medium contain derivative-compound-conjugate at its $IC_{50}$ value, as defined in the above experiments, plus a glycosylated steroid of the present invention, such as CME, which is known to increase the efficacy of 24-TC when not conjugated (hereinafter referred to as "the enhancer"). The enhancer is present at the following ratios relative to the derivative-compound conjugate: 0:1, 0.1:1, 1:1, 10:1, 100:1, 1000:1, or any concentration in between. The medium is inoculated with aliquots of *C. fasciculate* as described above and growth is monitored by changes in the absorbance at 535 nm relative to the uninoculated medium. Increased efficacy of the derivative-compound-conjugate in the presence of the enhancer is reflected in a lower rate of growth relative to the derivative-compound-conjugate alone. The optimum ratio of enhancer: derivative-compound conjugate is defined as that ratio which gives the lowest rate of growth.

ASSAY VI

Animal Experiments

Figure 20:
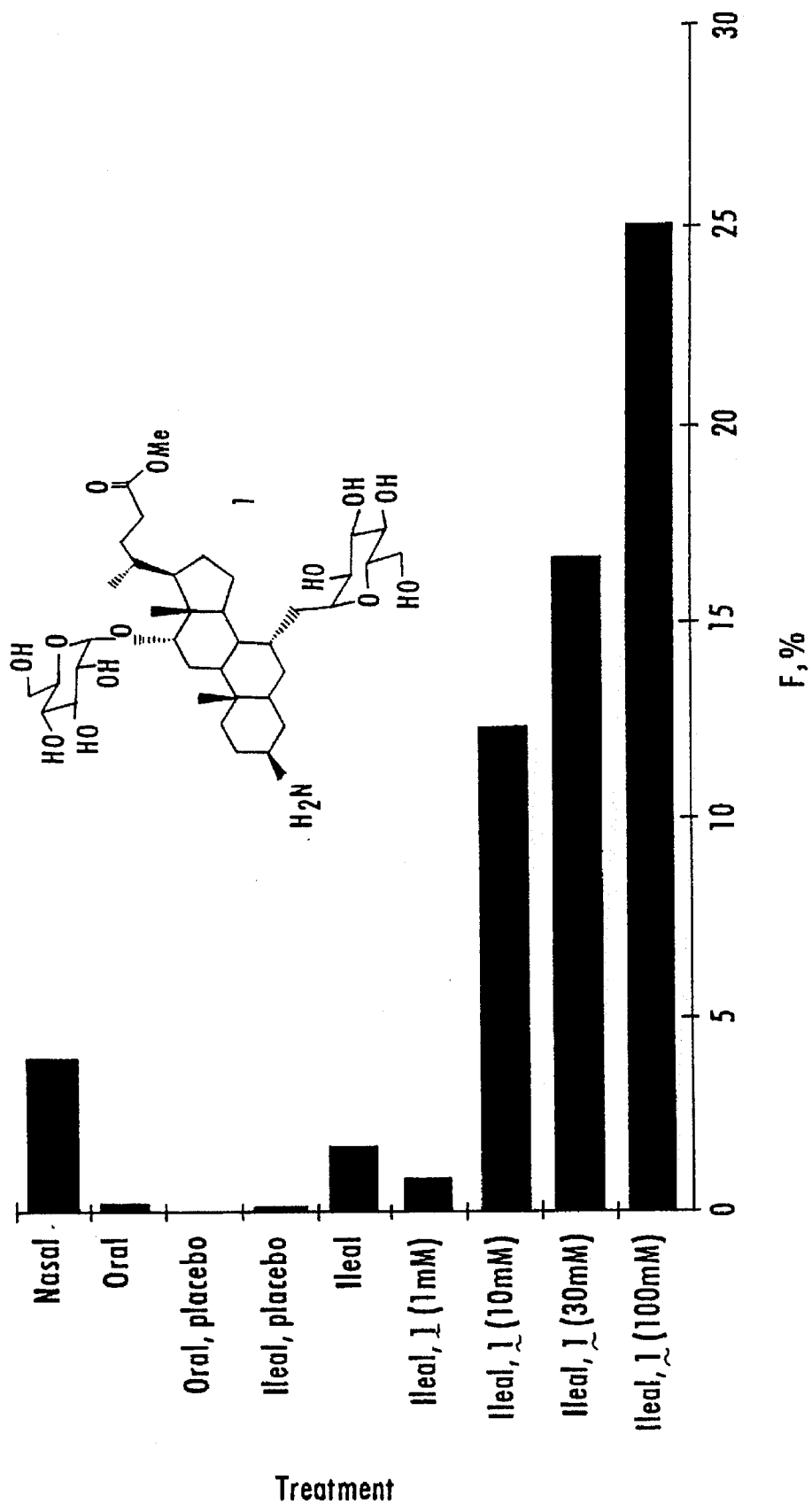
FIG. 20. Histograms illustrating the bioavailability of salmon calcitonin in rats as a function of mode of treatment.

A variety of animal experiments have been carried out which demonstrate the efficacy with which the compounds and conjugates of the present inv Results The results of the rat ileum experiments using calcitonin co-administered with various concentrations of 1 are presented graphically in FIG. 19. As indicated in this Figure, the plasma calcitonin levels rise with increasing amounts of 1. In the absence of 1 or at 1 mM 1, no appreciable amounts of calcitonin are found in the blood. In FIG. 20, the bioavailability of calcitonin is shown following various modes of treatment, including nasal, oral, and intraileal routes. As shown, significant amounts of calcitonin are made available with co-administration of 1 relative to a nasal, oral or ileal dose in the absence of 1.

Gentamicin and Vancomycin

The effectiveness of 1 in transporting gentamicin and vancomycin across the small intestine in the rat was also investigated. The single pass-perfusion model was utilized as described for calcitonin absorption studies and the drug/1 combination was administered into the ileum. The dosing solution consisted of 5 mg of antibiotic (approximately 10 mg/kg) with either 0, 10, 30 or 100 mM 1 in a 0.5 mL volume. Plasma samples were analyzed for the antibiotic concentration using an Emit immunoassay kit (Syva Co.).

Figure 21:
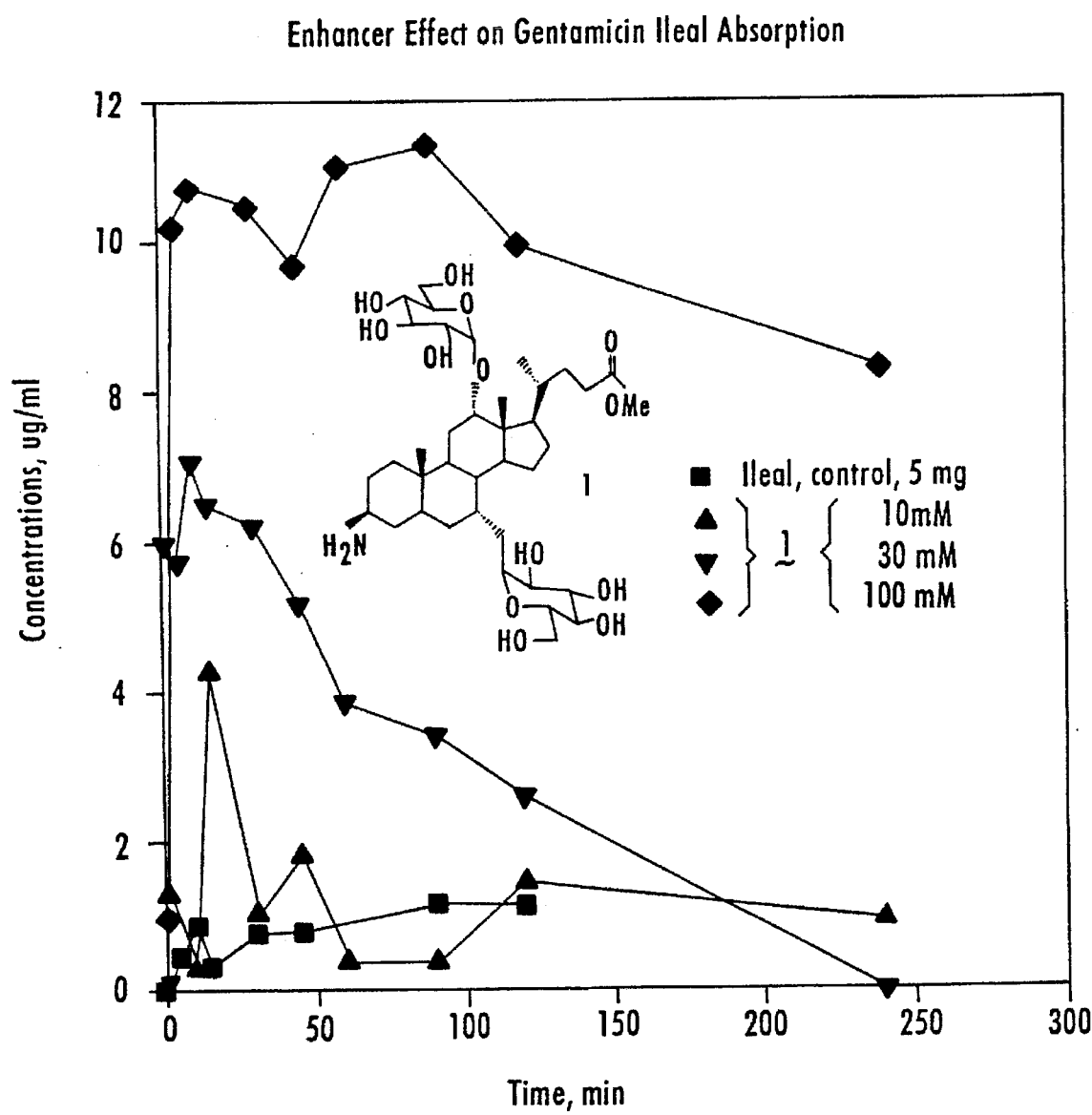
FIG. 21. Plot of gentamicin plasma concentration over time taken from rats that had been treated with gentamicin in the presence of varying amounts of compound 1 via ileal administration. Note the sustained, extended release characteristics of the ileal administration with 100 mM 1.
Figure 22:
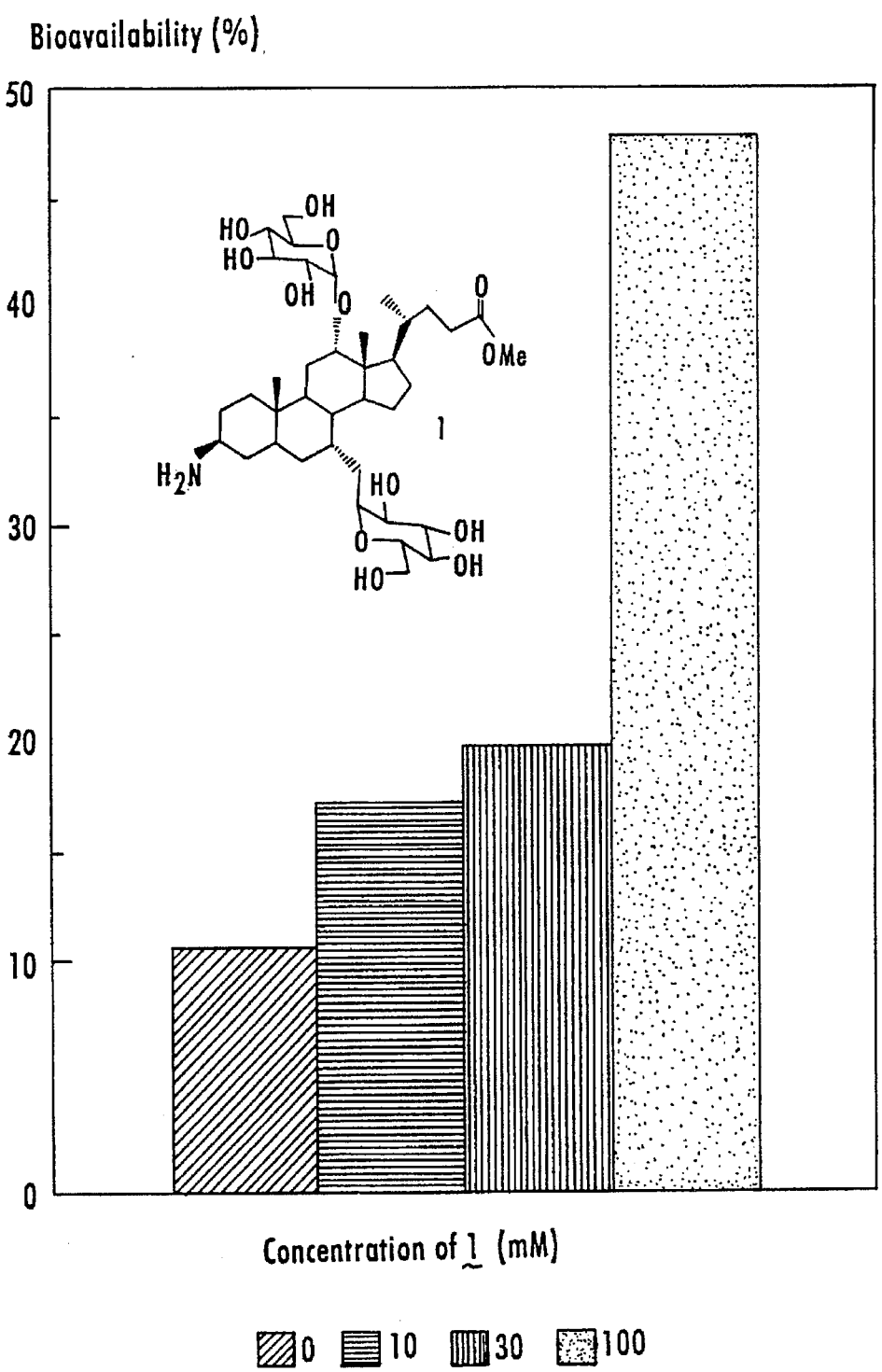
FIG. 22. Histograms illustrating the bioavailability of gentamicin in rats as a function of the concentration of 1.

Compound 1 mediated the uptake of gentamicin into the circulation in a dose dependent fashion and peak plasma levels of 7–11 µg/mL were achieved (FIG. 21). The highest plasma levels and the longest retention times were observed at the highest doses. The kinetics of uptake into plasma were rapid, reaching almost peak levels within 5 min at the 30 and 100 mM 1 concentrations and 10 min at the 10 mM concentration. Gentamicin levels returned to baseline within 240 min with mixtures containing 10 and 30 mM 1, but remained high with 100 mM 1 (exhibiting sustained, extended release characteristics). Plasma concentrations of gentamicin in the absence of 1 only reached 1–7 µg/mL. The pattern of absorption obtained by administration through the ileal route was very similar to colonic absorption. Bioavailability histograms are presented in FIG. 22. In the absence of 1, the ileal bioavailability was 10.7%, whereas with 10, 30, and 100 mM 1, the bioavailability rose to 17.3, 19.8, and 47.8%, respectively.

Vancomycin was also effectively absorbed following ileal administration in the presence of 1. The kinetics of uptake were very rapid, reaching peak plasma levels within 1–30 min. Peak plasma levels of 15–47 µg/mL were achieved with 100 mM 1, in contrast to 5–10 µg/mL in its absence. Vancomycin cleared more slowly from the circulation when administered via the ileum than via IV. The bioavailability of vancomycin is doubled in the presence of 1 relative to its ileal bioavailability in the absence of 1.

The above-described examples serve merely to illustrate certain aspects of the present invention and should not be construed to limit the invention in any way. Other embodiments of the present invention should be apparent to those of ordinary skill having considered the descriptions provided herein. Such other embodiments, including their equivalents, are considered to fall within the scope and spirit of the present invention, which is limited solely by the following claims.

What is claimed is:

1. A compound having the formula (III):

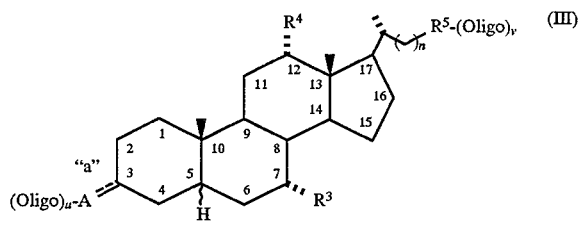

wherein

A is H, O, OH, $OR^6$, $NR^7R^8$, $N_3$, $NHCOR^7$, $OCOAr$, $O{-}CO{-}OR^9$, $O{-}CO{-}R^9$, $NCH_2C_6H_5$, and in which Ar is phenyl or phenyl substituted with 1-3 groups selected from the group consisting of halogen, $C_1$-$C_{12}$ alkyl or $C_1$-$C_3$ alkoxy;

"a" is a single bond in the alpha or beta configuration with the proviso that when A=O, "a" is a double bond;

$R^3$ is H, OH or $OR^6$;

$R^4$ is H, OH or $OR^6$;

$R^5$ is $CO_2R^{10}$, $CH_2OR^9$, $CONH_2$, $CONHR^7$, $CONR^7R^8$, $CO{-}S{-}R^{10}$, $CH_2S(O)_p{-}S{-}R^{10}$, $CH_2NH_2$, $CH_2NHR^7$, $CH_2NR^7R^8$, $CH_2{-}S(O)_p{-}S{-}R^{10}$;

$R^6$ is glycosyl moiety comprising 1-10 monosaccharide units in which the glycosidic linkage at the anomeric carbon atom of each monosaccharide unit is independently alpha or beta;

$R^7$ and $R^8$, independently are H, $C_1$-$C_4$ alkyl, $C_3$-$C_7$ cycloalkyl, $C_4$-$C_{10}$ alkylcycloalkyl, phenyl, benzyl, or, taken together are $(CH_2)_f$, where f=3-6;

$R^9$ is H or $C_1$-$C_3$ alkyl;

$R^{10}$ is H, $C_1$-$C_{10}$ alkyl, $C_1$-$C_{10}$ alkenyl, $C_1$-$C_{10}$ alkynyl, $C_6H_5$ or $CH_2C_6H_5$;

p is 0, 1 or 2;

n is 0, 1 or 2;

u is 0, 1, 2, 3, 4 or 5;

v is 0, 1, 2, 3, 4 or 5, so long as u and v are not both 0;

Oligo represents an oligonucleotide covalently attached to the group A or $R^5$ either directly or via a linker group; or a salt thereof.

2. A process for the preparation of a compound of the formula (I), with "a", A, n, and the R groups as defined previously in claim 1, which comprises:

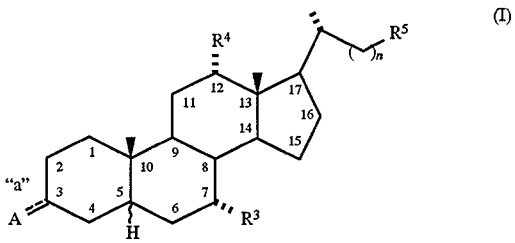

(a) reacting a protected glycoside, where the oxygen atoms at all positions of the sugar except the anomeric position are protected with the same or different groups selected from the group including esters and ethers such as alkyl, silyl, phenyl, or benzyl, with (b) an S—R entity under standard conditions where R is $C_1$-$C_{10}$ alkyl, pyridyl, furyl, thienyl, phenyl substituted with 1-3 groups selected from the group comprising halogen, $C_1$-$C_3$ alkyl, $NO_2$, $C_1$-$C_3$ alkoxy, to yield a protected thio-glycoside which is further reacted with (c) meta-chloroperoxybenzoic acid to yield the corresponding sulfoxide derivative and (d) converted to an activated glycosylating agent intermediate with a triflate-containing compound, such as triflic anhydride, methyl triflate, or trimethylsilyltriflate at −78° C. and contacting said activated glycosylating agent with (e) a steroid (in which any oxygens which are not to be glycosylated have been protected by standard methods) in the presence of 2,6-di-tert-butyl-4-methylpyridine in toluene, for formation of α,α glycoside linkages, or in propionitrile, for the formation of β,β linkages which is then (f) deprotected to yield glycosylated steroids of the formula (I).

3. The conjugate of claim 1 in which said oligonucleotide is an antisense oligonucleotide.

4. The conjugate of claim 1 in which said oligonucleotide has a sequence corresponding to a splice acceptor site or its complement.

5. The conjugate of claim 4 in which said oligonucleotide has the sequence 5' ACA CCC AAT TCT GAA AAT GG 3' (SEQ ID NO:1) or its complement.

6. The conjugate of claim 1 in which said oligonucleotide has a sequence corresponding to a primer binding site or its complement.

7. The conjugate of claim 6 in which said oligonucleotide has the sequence 5' AAG TCC CTG TTC GGG CGC CA 3' (SEQ ID NO:2) or its complement.

* * * * *